(12) United States Patent
Jacobson et al.

(10) Patent No.: US 11,584,736 B2
(45) Date of Patent: Feb. 21, 2023

(54) HETEROCYCLIC P2Y$_{14}$ RECEPTOR ANTAGONISTS

(71) Applicant: The United States of America, as represented by the Secretary, Department of Health and Human Services, Bethesda, MD (US)

(72) Inventors: Kenneth A. Jacobson, Silver Spring, MD (US); Jinha Yu, Gaithersburg, MD (US); Antonella Ciancetta, Belfast (IE); Zhiwei Wen, Rockville, MD (US); Young-Hwan Jung, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/967,177

(22) PCT Filed: Feb. 11, 2019

(86) PCT No.: PCT/US2019/017422
§ 371 (c)(1),
(2) Date: Aug. 4, 2020

(87) PCT Pub. No.: WO2019/157417
PCT Pub. Date: Aug. 15, 2019

(65) Prior Publication Data
US 2021/0047293 A1 Feb. 18, 2021

Related U.S. Application Data

(60) Provisional application No. 62/628,699, filed on Feb. 9, 2018.

(51) Int. Cl.
*C07D 401/14* (2006.01)
*A61P 11/06* (2006.01)
(Continued)

(52) U.S. Cl.
CPC ............ *C07D 401/14* (2013.01); *A61P 11/06* (2018.01); *C07C 235/84* (2013.01); *C07D 209/20* (2013.01); *C07D 211/34* (2013.01); *C07D 211/70* (2013.01); *C07D 249/06* (2013.01); *C07D 401/10* (2013.01); *C07D 409/10* (2013.01); *C07D 471/08* (2013.01)

(58) Field of Classification Search
None
See application file for complete search history.

(56) References Cited

U.S. PATENT DOCUMENTS

2013/0018189 A1 1/2013 Chi et al.

FOREIGN PATENT DOCUMENTS

CN 109096177 A 12/2018
EP 0064385 A1 11/1982
(Continued)

OTHER PUBLICATIONS

Database Registry Chemical Abstracts Service, Columbus, Ohio, Accession No. RN 1418184-38-9, Entered STN: Feb. 5, 2013.*
(Continued)

*Primary Examiner* — Samantha L Shterengarts
(74) *Attorney, Agent, or Firm* — Leydig, Voit & Mayer, Ltd.

(57) ABSTRACT

Disclosed are compounds of formulas (I)-(IX) for treating or preventing a disease or disorder responsive to antagonism of a P2Y$_{14}$R receptor agonist in a mammal in need thereof, wherein R$^1$-R$^8$, X, Y, Z, X', Y', Z', and A are as defined herein, that are useful in treating an inflammatory such as asthma, cystic fibrosis, and sterile inflammation of the kidney.

(Continued)

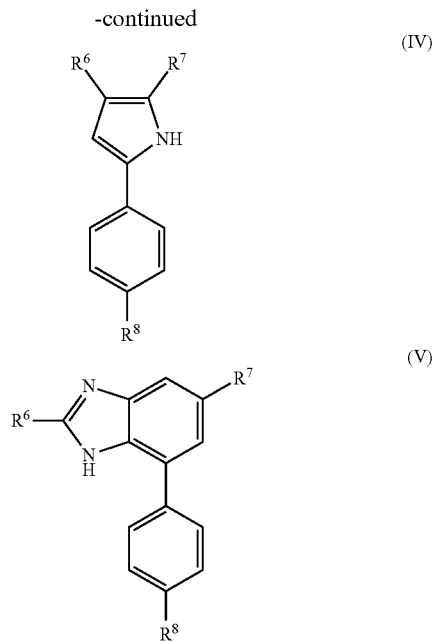

25 Claims, 3 Drawing Sheets

Figure 1A:
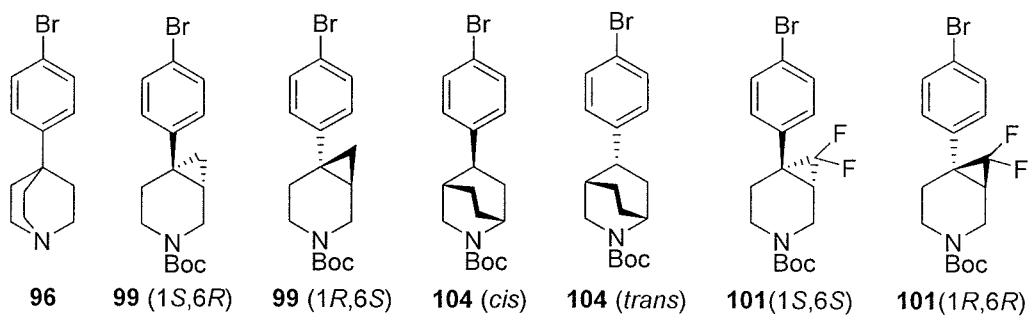

(51) Int. Cl.
C07C 235/84 (2006.01)
C07D 209/20 (2006.01)
C07D 211/34 (2006.01)
C07D 211/70 (2006.01)
C07D 249/06 (2006.01)
C07D 401/10 (2006.01)
C07D 409/10 (2006.01)
C07D 471/08 (2006.01)

(56) References Cited

FOREIGN PATENT DOCUMENTS

| WO | WO 2007/025575 A1 | 3/2007 |
|---|---|---|
| WO | WO 2012/087872 A1 | 6/2012 |
| WO | WO 2013/018189 A1 | 2/2013 |
| WO | WO 2014/135617 A1 | 9/2014 |
| WO | WO 2017/023905 A1 | 2/2017 |
| WO | WO 2017/053769 A1 | 3/2017 |
| WO | WO 2017/087608 A1 | 5/2017 |
| WO | WO 2018/165614 A1 | 9/2018 |

OTHER PUBLICATIONS

Database Registry Chemical Abstracts Service, Columbus, Ohio, Accession No. RN 80029-25-0, Entered STN: Nov. 16, 1984.*
Abbracchio et al., "International Union of Pharmacology LVIII: Update on the P2Y G Protein-Coupled Nucleotide Receptors: From Molecular Mechanisms and Pathophysiology to Therapy," Pharmacol. Rev. 58(3):281-341 (2006).
Azroyan et al., "Renal Intercalated Cells Sense and Mediate Inflammation via the P2Y$_{14}$ Receptor," PLoS ONE 10(3):e0121419 (2015).
Barrett et al., "A Selective High-Affinity Antagonist of the P2Y$_{14}$ Receptor Inhibits UDP-Glucose-Stimulated Chemotaxis of Human Neutrophils," Mol. Pharmacol., 84:41-49 (2013).
Berge et al., "Pharmaceutical Salts," Review Article from Journal of Pharmaceutical Sciences, 66(1):1-19 (1977).
Burnstock et al., "Purinergic signaling: from discovery to current developments," Exp. Physiol., 99.1:16-34 (2014).
Cekic et al., "Purinergic regulation of the immune system," Nature Rev. Immunol., 16:177-192 (2016).
Chemical Abstracts Online, Database Registry, Accession No. 1159980-68-3 (Jun. 25, 2009).
Chemical Abstracts Online, Database Registry, Accession No. 1159980-69-4 (Jun. 25, 2009).
Chemical Abstracts Online, Database Registry, Accession No. 1159980-70-7 (Jun. 25, 2009).
Deluca et al., "Parenteral Drug-Delivery Systems," Pharmaceutics and Pharmacy Practice, Chapter 8, p. 238-250 (J. B. Lippincott Co., Philadelphia, PA, 1982).
European Patent Office, Invitation to Pay Additional Fees in International Patent Application No. PCT/US2019,017422, dated Apr. 2, 2019.
European Patent Office, International Search Report in International Patent Application No. PCT/US2019/017422, dated Jul. 19, 2019.
European Patent Office, Written Opinion in International Patent Application No. PCT/US2019/017422, dated Jul. 19, 2019.
Fejes et al., "A New Synthesis of 3,5-Diaryl-pyrrole-2-carboxylic Acids and Esters," Tetrahedron, 56:8545-8553 (2000).
Gao et al., "UDP-glucose acting at P2Y$_{14}$ receptors is a mediator of mast cell degranulation," Biochem. Pharmacol, 79(6):873-879 (2010).
Gao et al., "The role of P2Y$_{14}$ and other P2Y receptors in degranulation of human LAD2 mast cells," Purinergic Signalling, 9:31-40 (2013).
Gauthier et al., "The Identification of 4,7-disubstituted naphthoic acid derivatives as UDP-competitive Antagonists of P2Y$_{14}$," Bioorganic & Medicinal Chemistry Letters, 21:2836-2839 (2011).
Idzko et al., "Nucleotide signalling during inflammation," Nature 509(7500):310-317 (2014) doi:10.1038/nature13085.
Kawamura et al., "Diphenylpyridines—A New Class of Herbicides," ACS Symposium Series, Chapter 11, 504:103-108 (1992).
Kim et al., "2,3-Dichloro-5,6-dicyano-para-benzoquinone (DDQ)/Methanesulfonic Acid (MsOH)-Mediated Intramolecular Arene-Alkene Oxidative Coupling," Adv. Synth. Catal. 356:697-704 (2014).
Kinoshita et al., "Secretion of Matrix Metalloproteinase-9 from Astrocytes by Inhibition of Tonic P2Y$_{14}$-Receptor-Mediated Signal(s)," Cell. Mol. Neurobiol. 33:47-58 (2013).
Kiselev et al., "Exploring a 2-Naphthoic Acid Template forthe Structure-Based Design of P2Y$_{14}$ Receptor Antagonist Molecular Probes," ACS Chem. Biol., 9:2833-2842 (2014).
Kobayashi et al., "Multiple P2Y Subtypes in Spinal Microglia are Involved in Neuropathic Pain After Peripheral Nerve Injury," GLIA, 60:1529-1539 (2012).
Lazarowski et al., "UDP-Sugars as Extracellular Signaling Molecules: Cellular and Physiologic Consequences of P2Y14 Receptor Activation," Mol. Pharmacol., 88:151-160 (2015).
Pak et al., "A New Synthesis of Pyrrole-2-Carboxylic Acids," Synlett, 8:1271-1273 (1999).
Remingtons' Pharmaceutical Sciences, 18$^{th}$ Edition, p. 1445 (1990).
Sesma et al., "The UDP-sugar-sensing P2Y$_{14}$ receptor promotes Rho-mediated signaling and chemotaxis in human neutrophils," Am. J. Physiol. Cell Physiol., 303:C490-C498 (2012).
Sesma et al., "UDP-glucose promotes neutrophil recruitment in the lung," Purinergic Signalling, 12:627-635 (2016).
Stachon et al., "Extracellular ATP Induces Vascular Inflammation and Atherosclerosis via Purinergic Receptor Y$_2$ in Mice," Arterioscler. Thromb. Vase. Biol., 36:1577-1586 (2016).
Trissel, "Intravenous Infusion Solutions," ASHP Handbook on Injectable Drugs, Fourth Edition, p. 622-630, American Society of Hospital Pharmacists, Inc., Bethesda, MD (1986).
Xu et al., "GPR105 Ablation Prevents Inflammation and Improves Insulin Sensitivity in Mice with Diet-Induced Obesity," J. Immunol, 189:1992-1999 (2012).
Yu et al., "Structure-Guided Modification of Heterocyclic Antagonists of the P2Y14 Receptor," J. Med. Chem., 61:4860-4882 (2018).
Junker et al., "Structure-Based Design of 3-(4-Aryl-1H-1,2,3-triazol-1-yl)-Biphenyl Derivatives as P2Y14 Receptor Antagonists," J. Med. Chem., 59: 6149-5168(2016).

* cited by examiner

HETEROCYCLIC P2Y$_{14}$ RECEPTOR ANTAGONISTS

CROSS-REFERENCE TO A RELATED APPLICATION

This patent application is the U.S. national phase of International Patent Application No. PCT/US2019/017422, filed Feb. 11, 2019, which claims the benefit of U.S. Provisional Patent Application No. 62/628,699 filed Feb. 9, 2018, the disclosures of which are incorporated herein by reference in their entirety for all purposes.

STATEMENT REGARDING FEDERALLY SPONSORED RESEARCH OR DEVELOPMENT

This invention was made with Government support under Grant Numbers ZIA DK031116-29 awarded by the NIDDK Intramural Research Program and Contract #HHSN-271-2008-00025-C awarded by the Psychoactive Drug Screening Program of the National Institute of Mental Health. The Government has certain rights in this invention.

BACKGROUND OF THE INVENTION

Extracellular nucleotides released by tissue and organs during stress or injury activate a class of cell-surface receptors (P2Rs) to boost the innate and adaptive immune responses (1-3). This mechanism acts as a time-dependent component of the signaling purinome, along with the anti-inflammatory adenosine receptors (ARs, also termed P1 receptors), to protect the organism in various challenged circumstances. The P2Y$_{14}$ receptor (P2Y$_{14}$R) responds to endogenous agonists uridine-5'-diphosphoglucose and uridine-5'-diphosphate to mediate inflammatory activity, in part by activating neutrophil motility (4-6). Structurally, the P2Y$_{14}$R belongs to the 6-branch of rhodoposin-like G protein-coupled receptors (GPCRs). Three subtypes of the P2YRs are preferentially coupled to inhibition of adenylate cyclase through guanine nucleotide inhibitory (G$_i$) protein: P2Y$_{12}$R, P2Y$_{13}$R and P2Y$_{14}$R. Selective P2Y$_{14}$R antagonists are sought as potential agents for treating asthma, sterile inflammation of the kidney, diabetes and neurodegeneration (7-12). However, only a few classes of antagonists are known, so there is a clear need for more diverse competitive P2Y$_{14}$R antagonists. Other subtypes of the P2YR family in general, e.g. P2Y$_2$R and P2Y$_6$R, are also associated with proinflammatory effects, and their antagonists are desired for their anti-inflammatory activity (13, 14).

Antagonists of the P2Y$_{14}$R were first reported by Black and colleagues (19), and of the two classes reported, naphthoic acids and pyrido[4,3-d]pyrimidines, only the former appeared to be competitive antagonists. Thus, there is an unmet need for diverse competitive P2Y$_{14}$R antagonists.

BRIEF SUMMARY OF THE INVENTION

The invention provides a compound of formula (I):

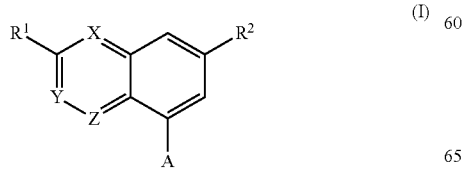

(I)

wherein (i) X is N, Y is CH, and Z is CH, (ii) X is CH, Y is N, and Z is CH, or (iii) X is CH, Y is CH, and Z is N, R$^1$ is halo or trifluoromethyl, R$^2$ is COOH, CN, CONH$_2$, or

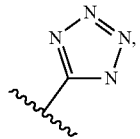 [SMILES: *c1nnn[nH]1]

A is selected from the group consisting of

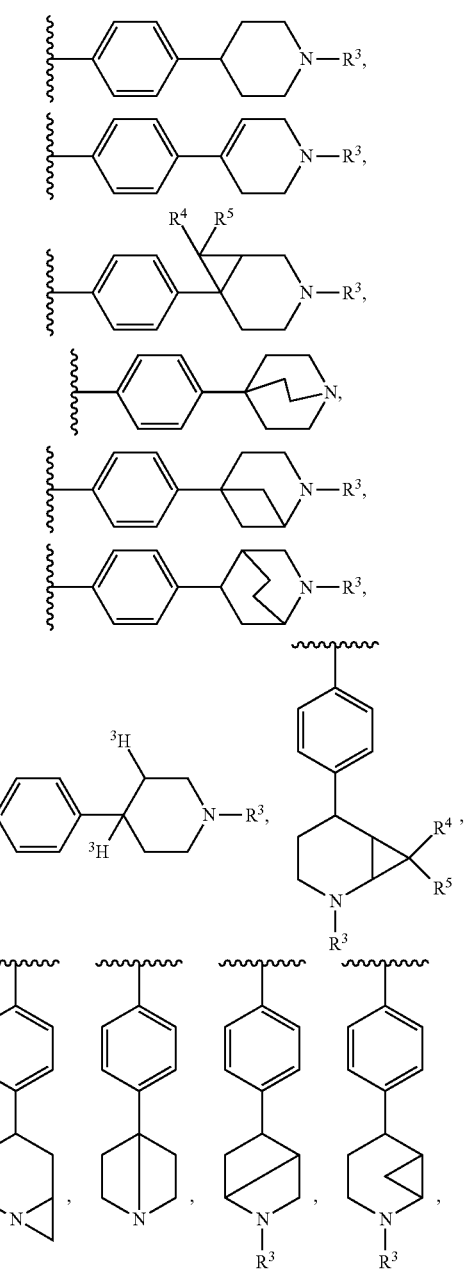

-continued
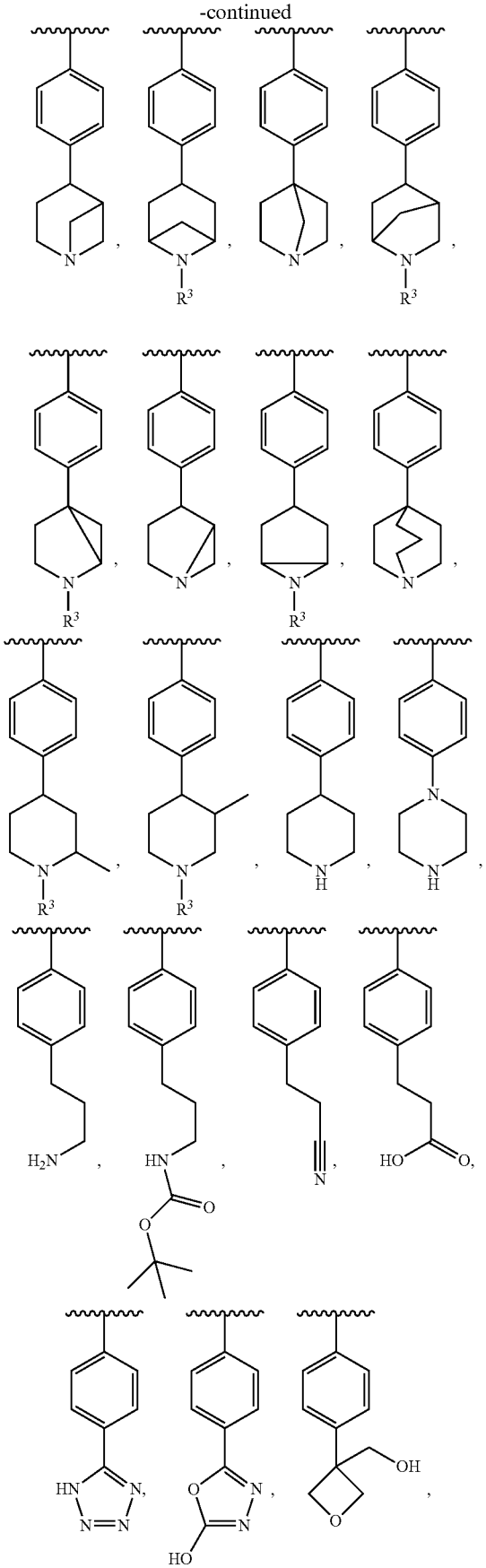
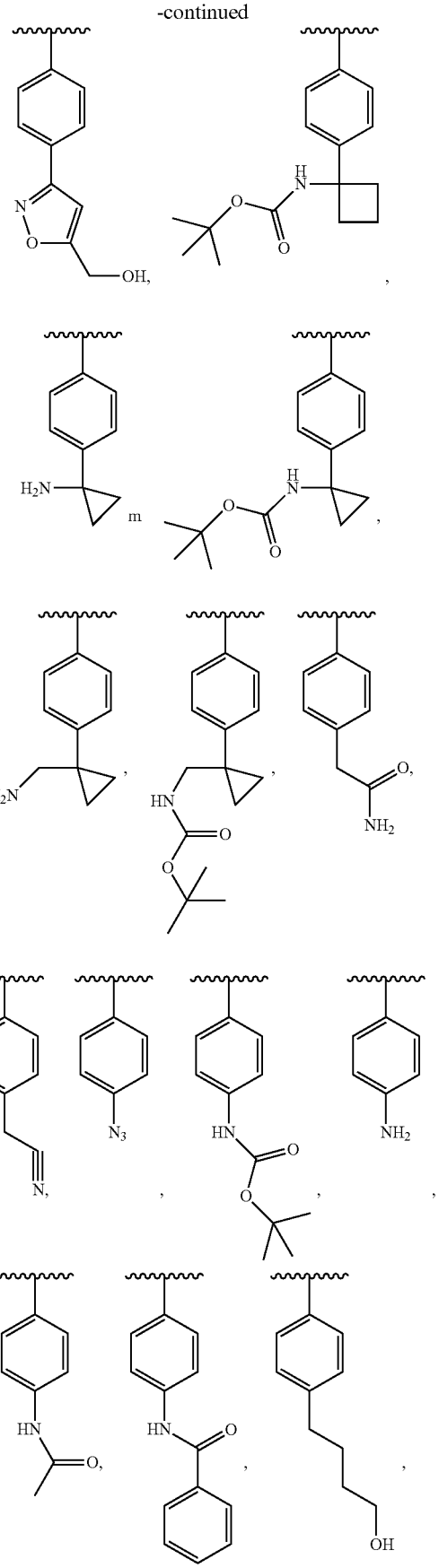

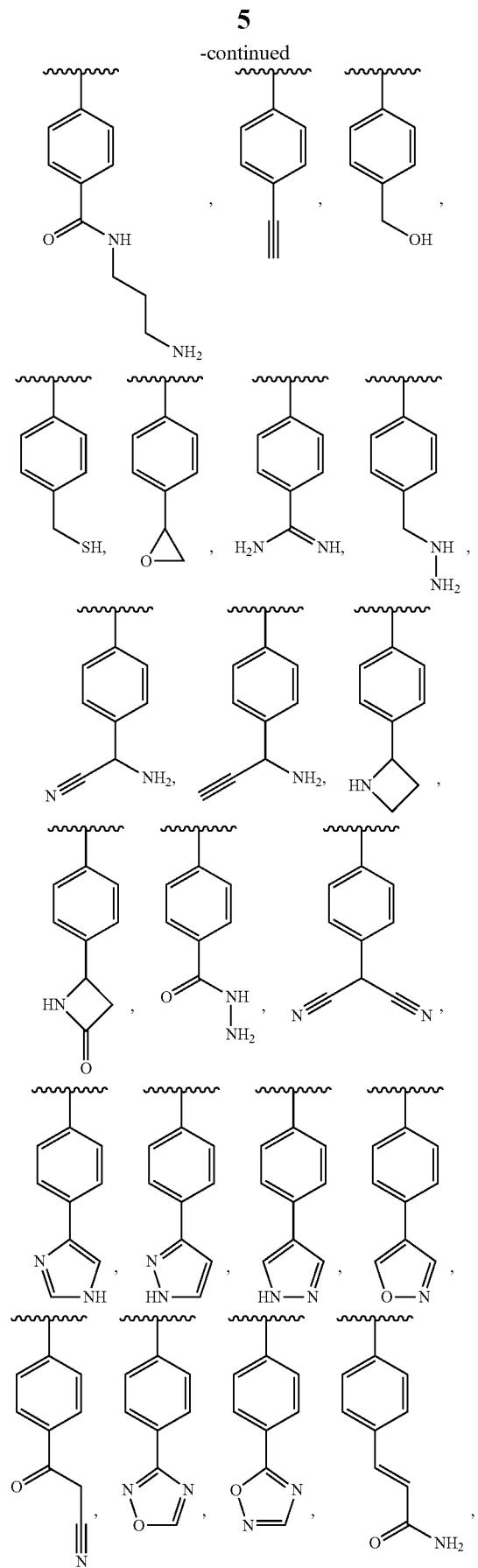

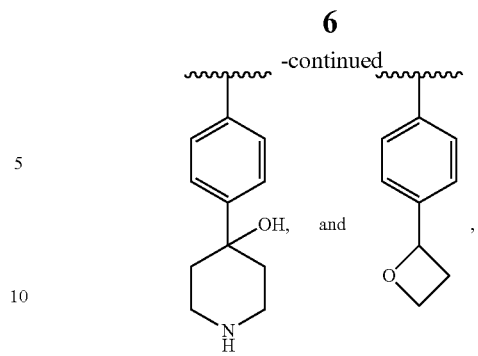

wherein R³ is at each occurrence H, $C_1$-$C_{10}$ alkyl, $C_3$-$C_{10}$ alkynyl, benzyl, $C_1$-$C_6$ alkoxycarbonyl, —CO(CH$_2$)$_2$O)$_o$(CH$_2$)$_p$Q, or —(CH$_2$)$_q$(CH$_2$)$_2$O)$_o$(CH$_2$)$_p$Q wherein Q is H, $C_1$-$C_6$ alkyl, or NR$^{28}$R$^{29}$, wherein R$^{27}$ and R$^{28}$ are independently H, $C_1$-$C_6$ alkyl, $C_1$-$C_6$ alkylcarbonyl, or $C_1$-$C_6$ alkoxycarbonyl, and wherein R⁴ and R⁵ are each H or F, or a pharmacologically acceptable salt thereof.

The invention also provides a compound of formula (II), (III), (IV), or (V):

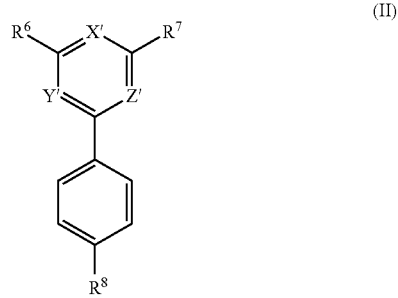

(II)

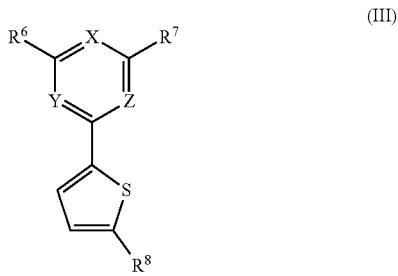

(III)

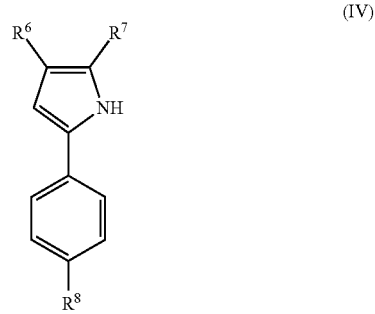

(IV)

(V)
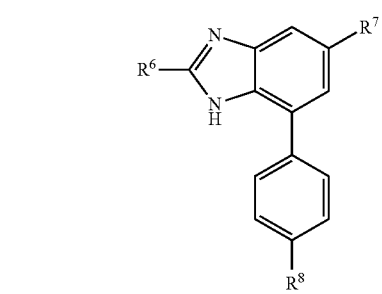
wherein R⁶ is selected from the group consisting of
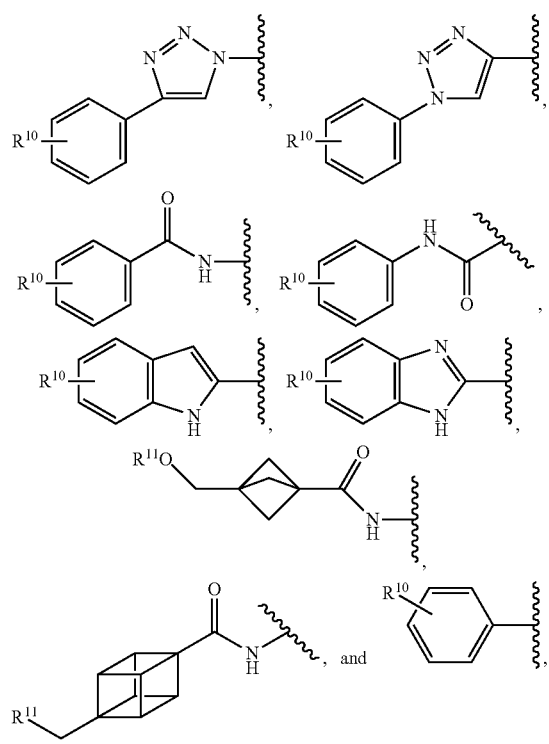
R⁷ is COOH, CONH₂, CN,
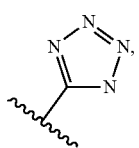 [SMILES: *c1nnn[nH]1]
or COCH₂NMe₂,
R⁸ is selected from the group consisting of $C_1$-$C_{10}$alkyl, —CONHR₁₂R₁₃, —CONH(CH₂)$_m$—NHR₁₄R₁₅,
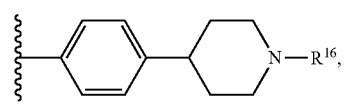
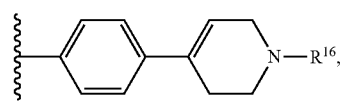
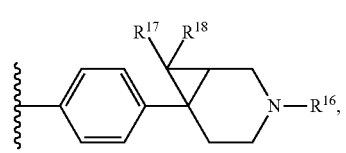
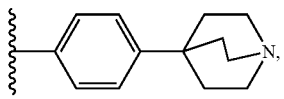
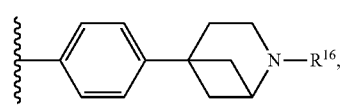
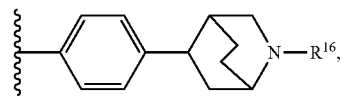
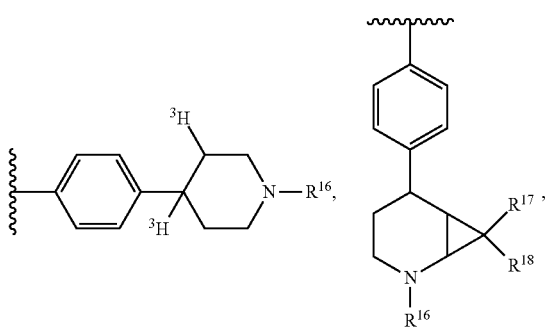
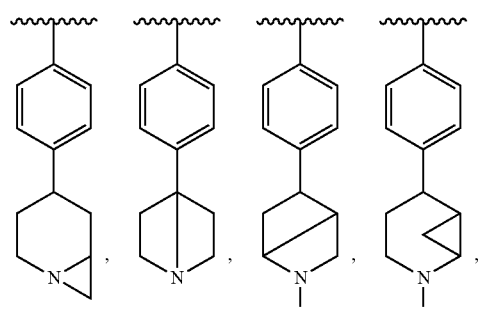
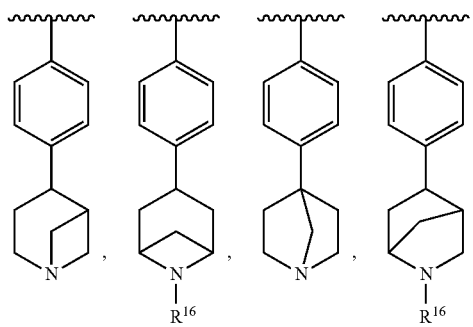

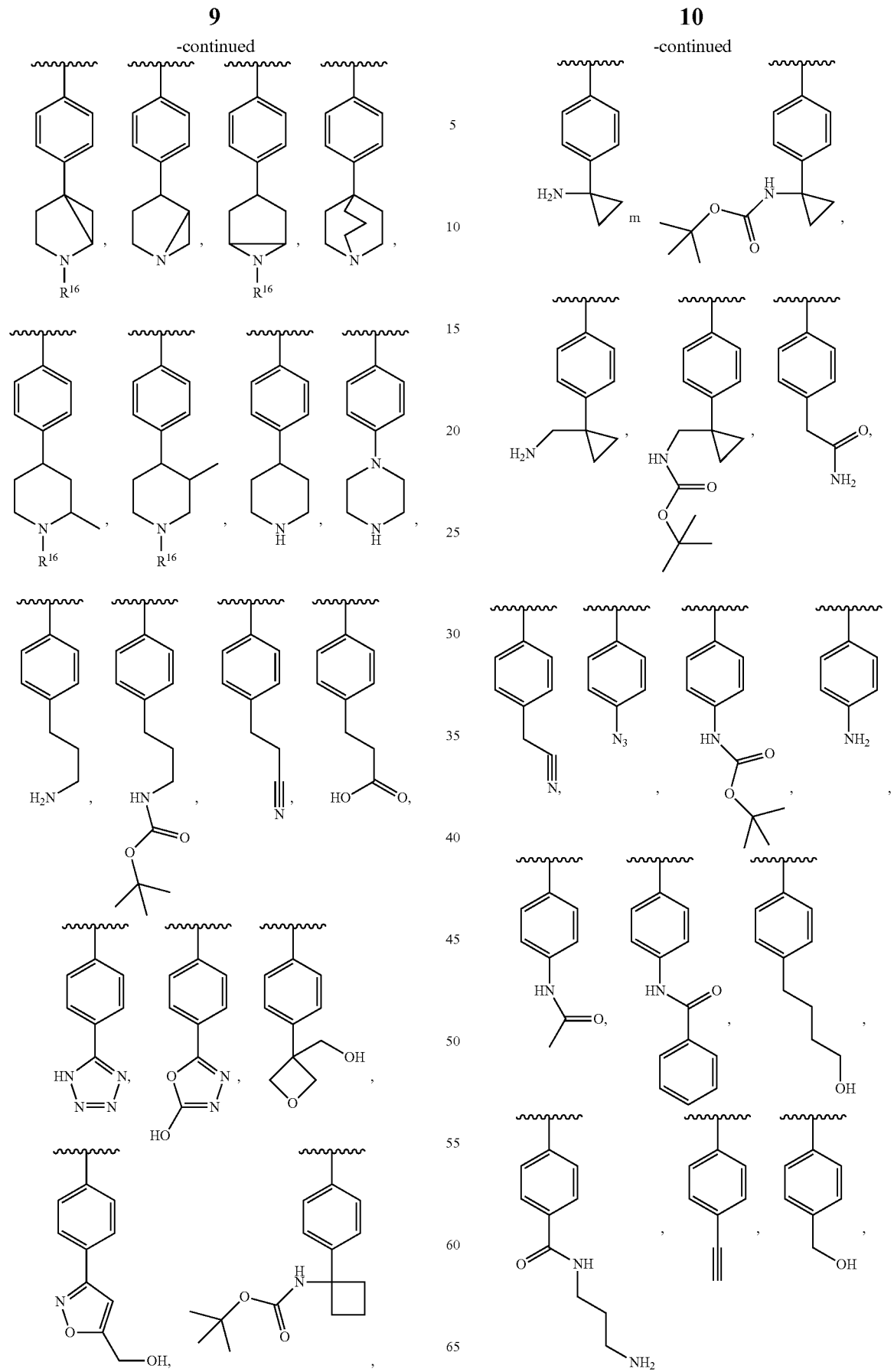

-continued

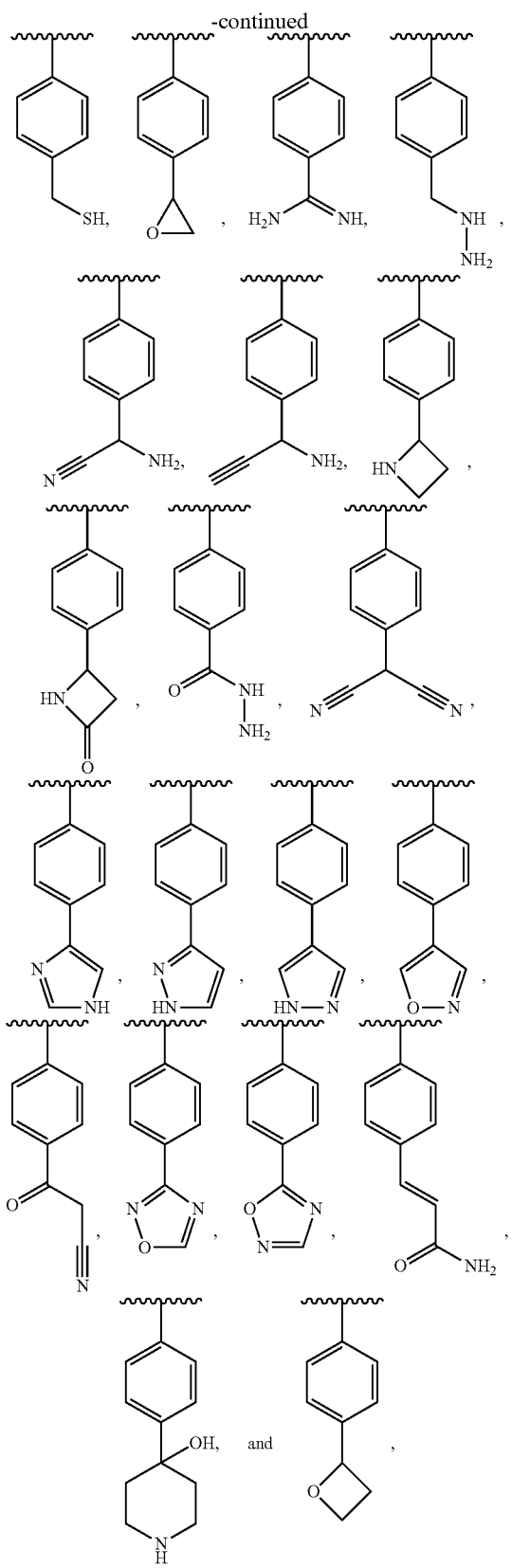

$R^{10}$ is halo or $CF_3$,
$R^{11}$ is halo, OH, or $C_1$-$C_6$ alkoxy,
$R^{12}$ and $R^{13}$ are independently H or $C_1$-$C_6$ alkyl,
$R^{14}$ and $R^{15}$ are independently H or $C_1$-$C_6$ alkyl,
$R^{16}$ is H, $C_1$-$C_{10}$ alkyl, or $C_3$-$C_{10}$ alkynyl, and
$R^{17}$ and $R^{18}$ are both H or both F,
m is an integer of from 1 to about 10,
(i) X is N, Y is CH, and Z is CH, (ii) X is CH, Y is N, and Z is CH, or (iii) X is CH, Y is CH, and Z is N,
X' and Y' are CH or N, and
Z' is N or $CR^9$ wherein $R^9$ is H or $C_1$-$C_6$ alkyl,
or a pharmaceutically acceptable salt thereof.

The invention further provides a method for antagonizing a $P2Y_{14}R$ receptor in a mammal in need thereof comprising to the mammal a compound of the invention or a pharmaceutically acceptable salt thereof.

The invention additionally provides a method of treating or preventing an inflammatory condition in a mammal in need thereof comprising to the mammal a compound of the invention or a pharmaceutically acceptable salt thereof.

BRIEF DESCRIPTION OF THE SEVERAL VIEWS OF THE DRAWING(S)

Figure 1B:
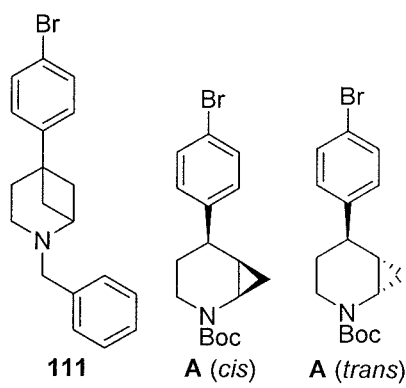
Figure 1C:
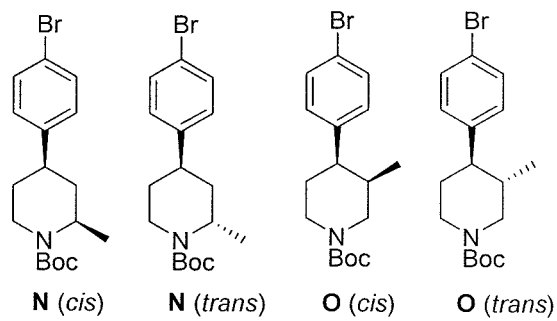
Figure 1D:
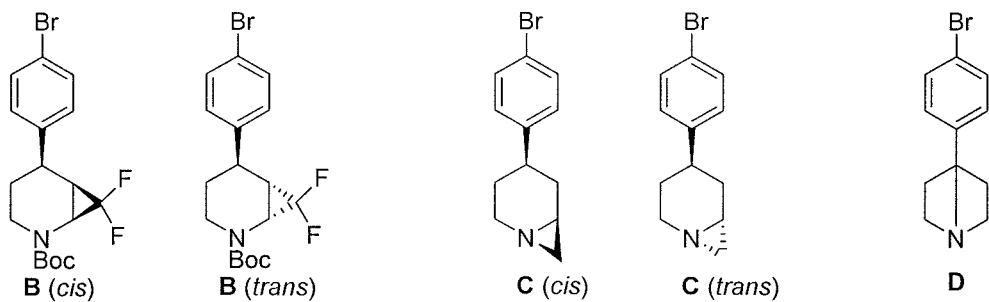
Figure 1D:
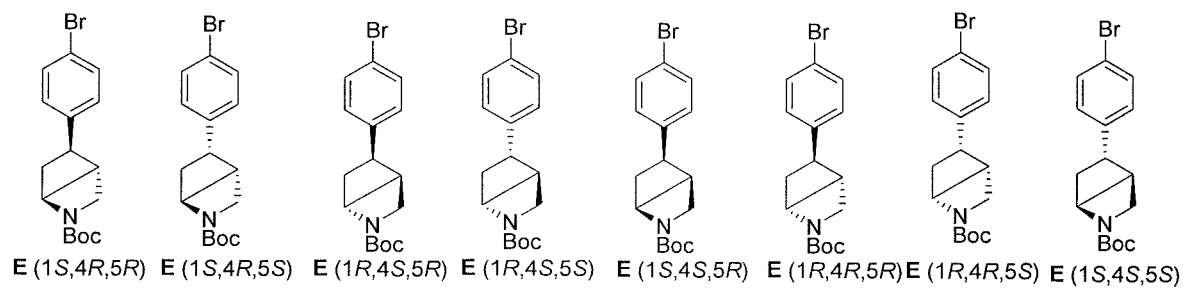
Figure 1D:
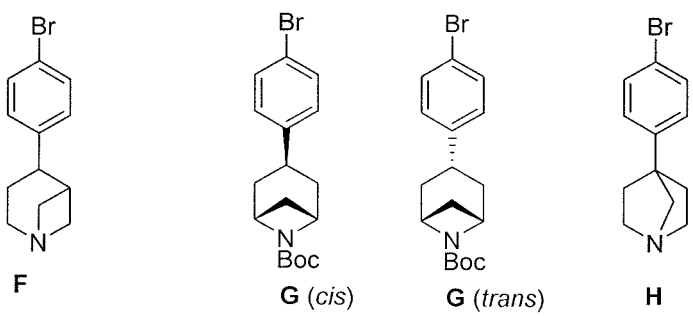
Figure 1D:
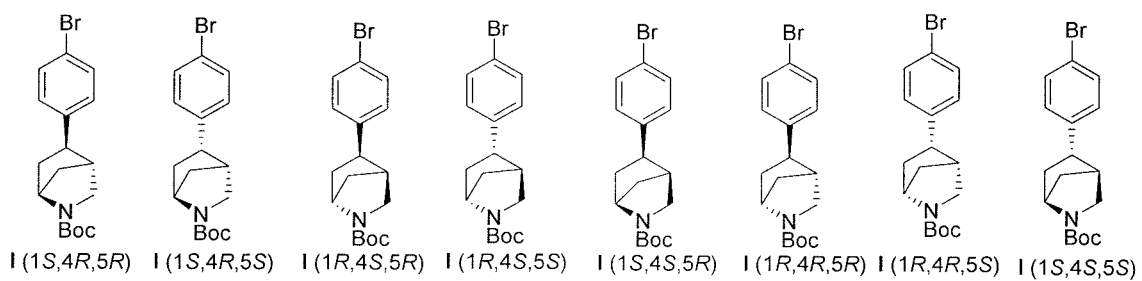
Figure 1D:
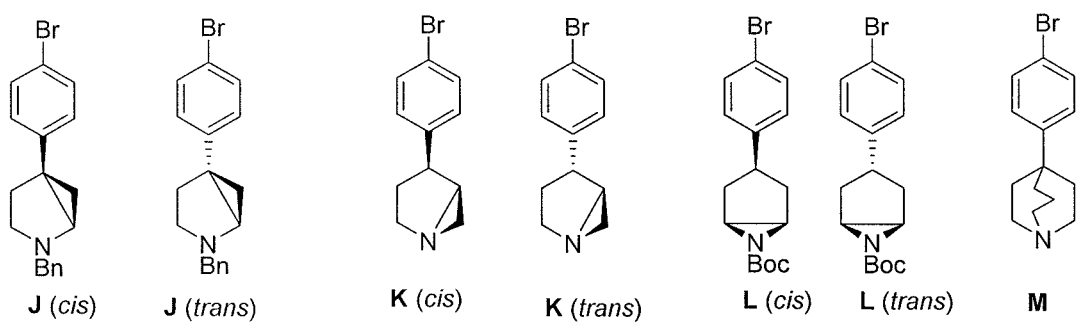

FIGS. 1A-1D show the structures of synthetic piperidine-containing intermediates for preparation of compounds in accordance with embodiments of the invention.

DETAILED DESCRIPTION OF THE INVENTION

In an embodiment, the invention provides a compound of formula (I):

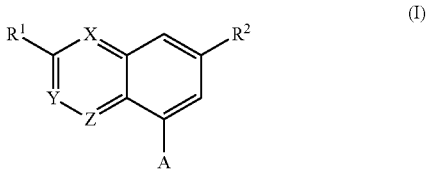

wherein (i) X is N, Y is CH, and Z is CH, (ii) X is CH, Y is N, and Z is CH, or (iii) X is CH, Y is CH, and Z is N,
$R^1$ is halo or trifluoromethyl,
$R^2$ is COOH, CN, $CONH_2$, or

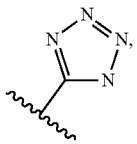 [SMILES: *c1nnn[nH]1]

A is selected from the group consisting of

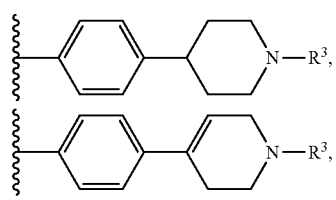

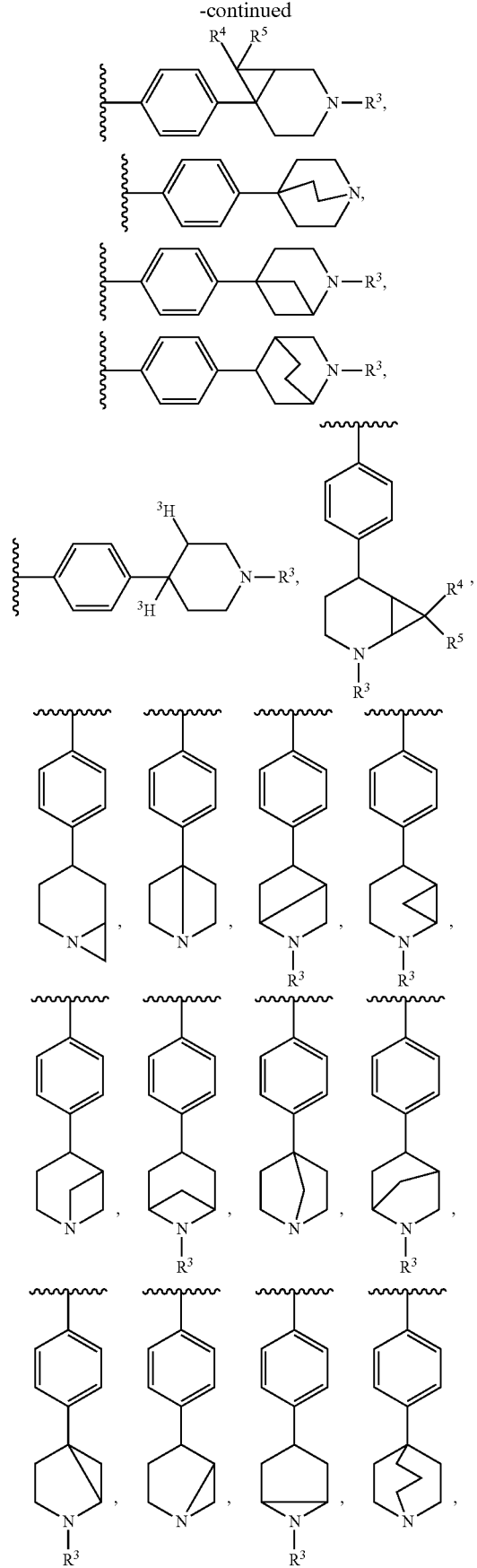
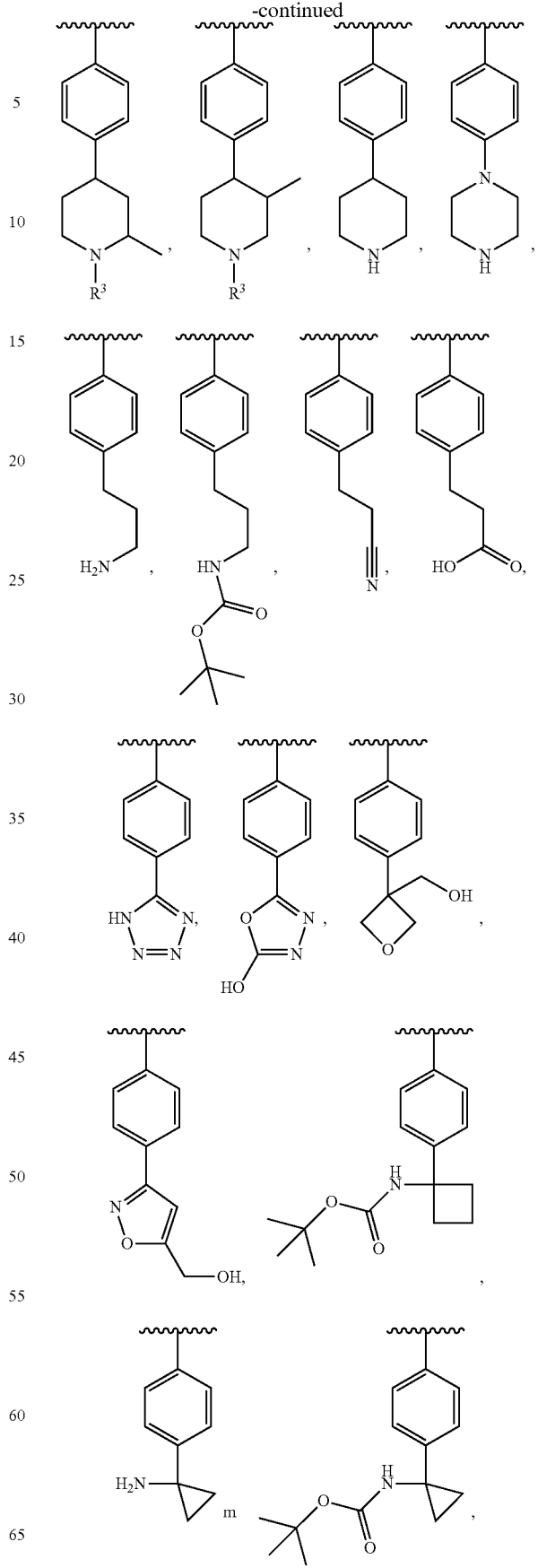

-continued

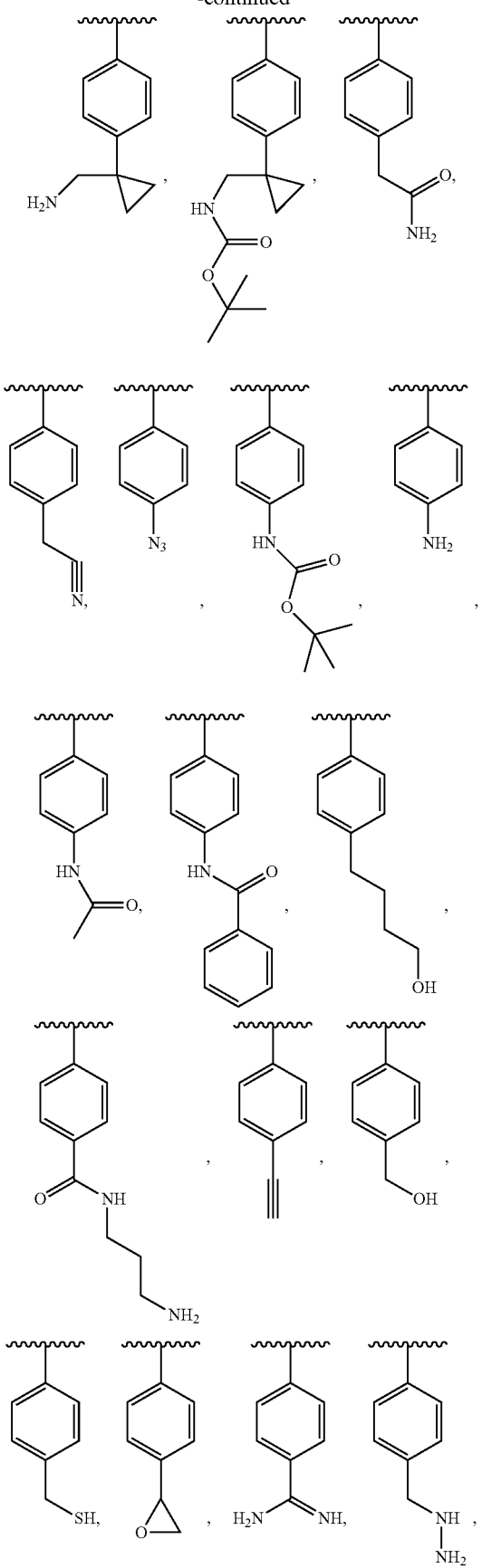

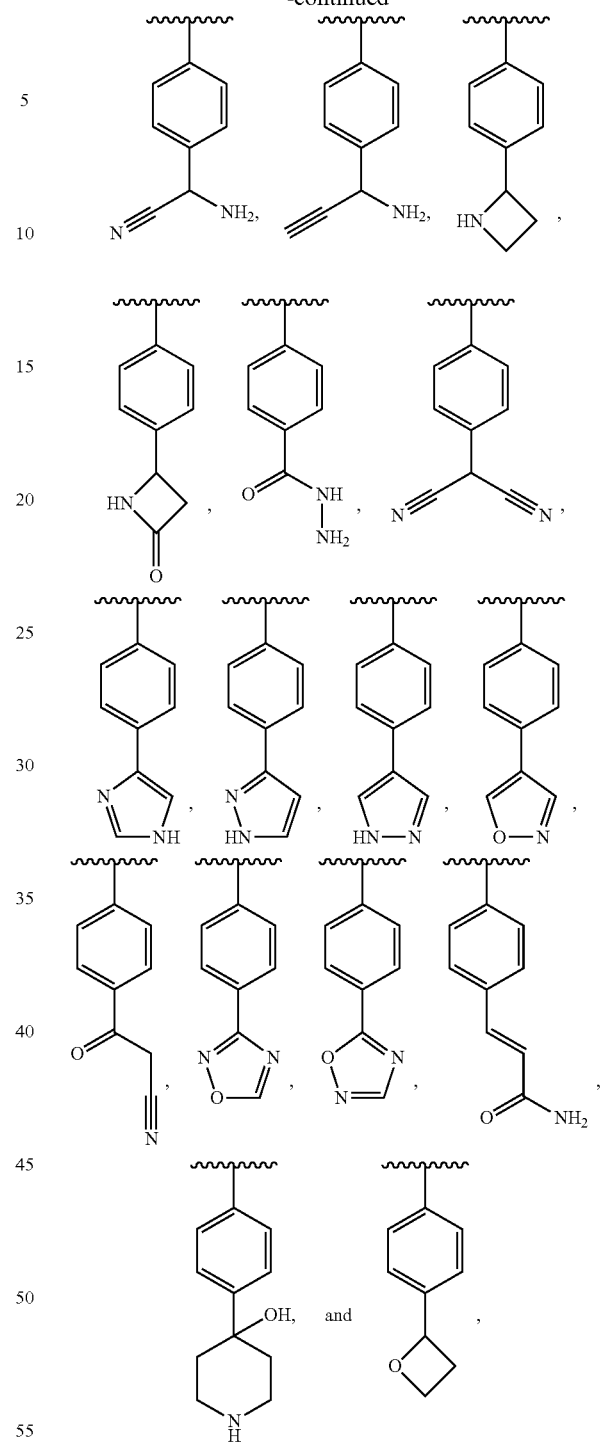

wherein $R^3$ is at each occurrence H, $C_1$-$C_{10}$ alkyl, $C_3$-$C_{10}$ alkynyl, benzyl, $C_1$-$C_6$ alkoxycarbonyl, —CO($CH_2$)$_2$O)$_o$($CH_2$)$_p$Q, or —($CH_2$)$_q$($CH_2$)$_2$O)$_o$($CH_2$)$_p$Q wherein Q is H, $C_1$-$C_6$ alkyl, or $NR^{28}R^{29}$, wherein $R^{27}$ and $R^{28}$ are independently H, $C_1$-$C_6$ alkyl, $C_1$-$C_6$ alkylcarbonyl, or $C_1$-$C_6$ alkoxycarbonyl, and wherein $R^4$ and $R^5$ are each H or F, or a pharmacologically acceptable salt thereof.

In certain embodiments, X, Y, and N are all CH.

In certain embodiments, $R^1$ is trifluoromethyl.

In certain embodiments, A is
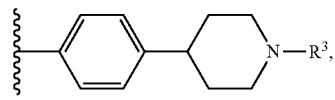
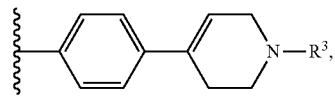
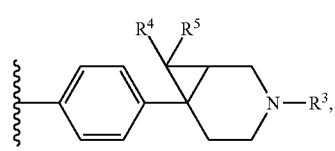
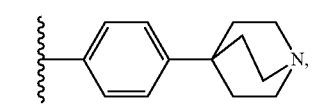
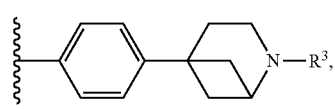
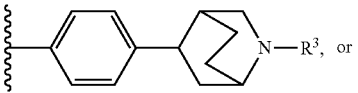 or
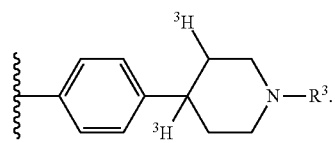
In certain particular embodiments, the compound is selected from the group consisting of:
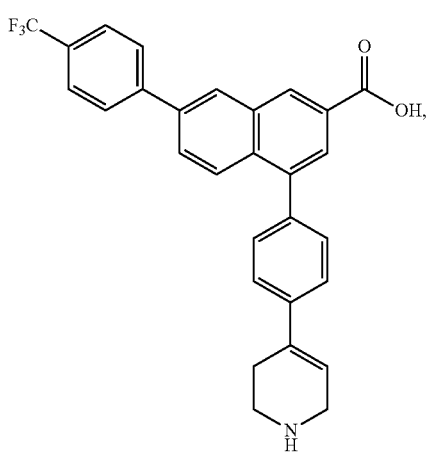
-continued
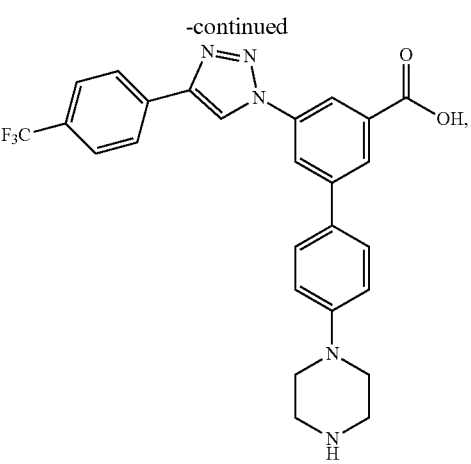
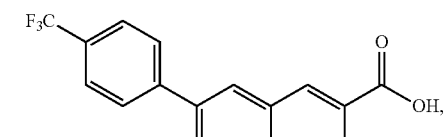
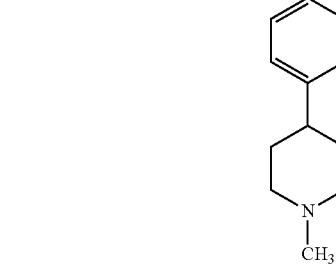
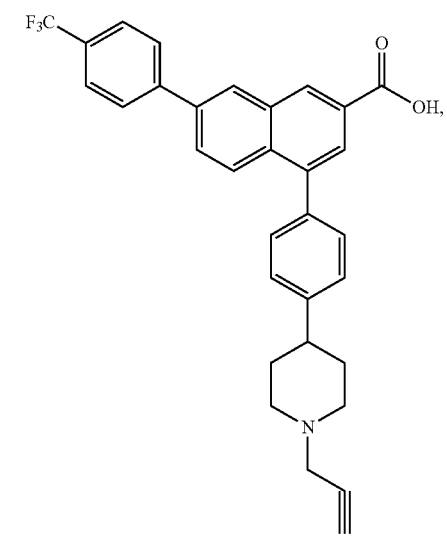

19
-continued
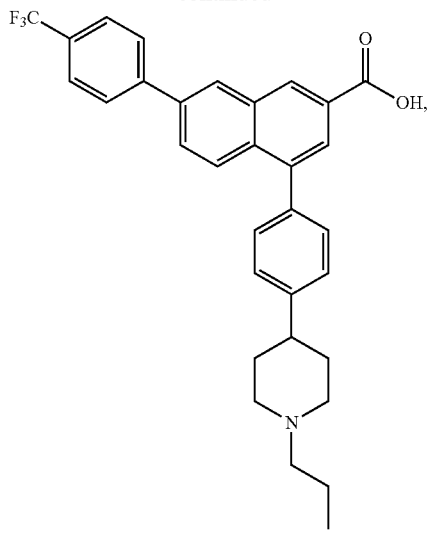
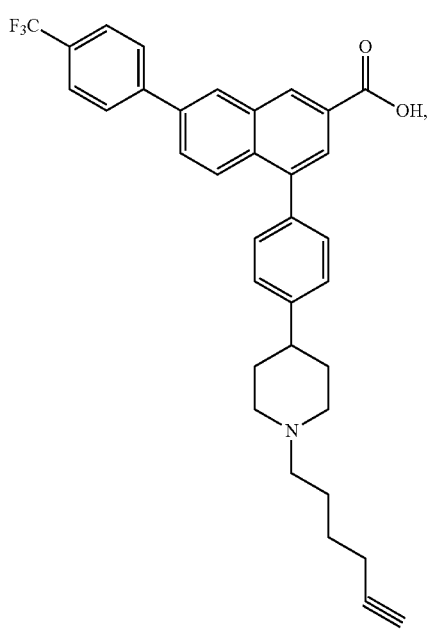
20
-continued
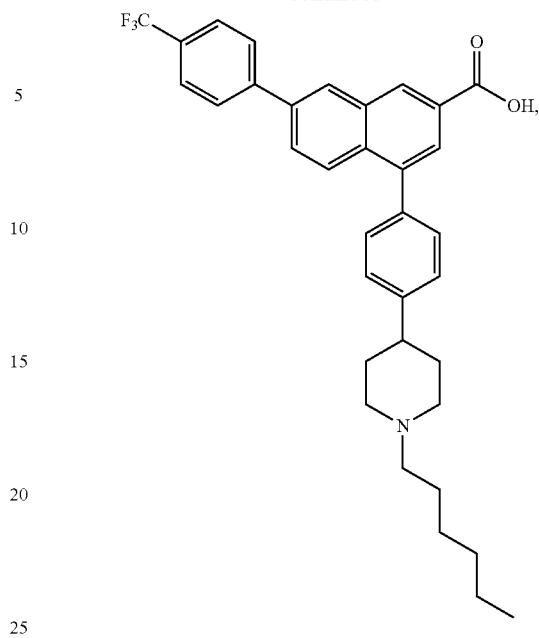
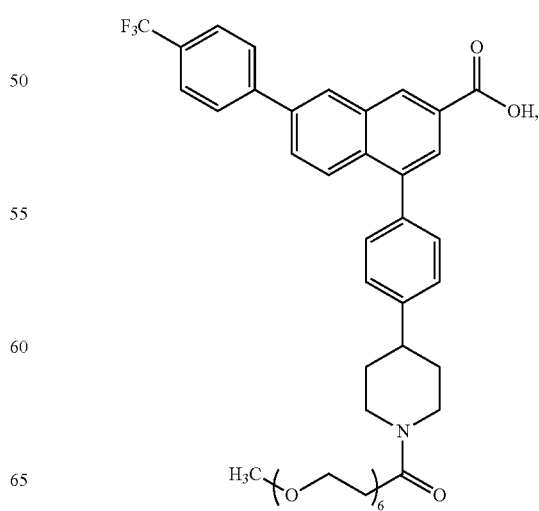

21
-continued
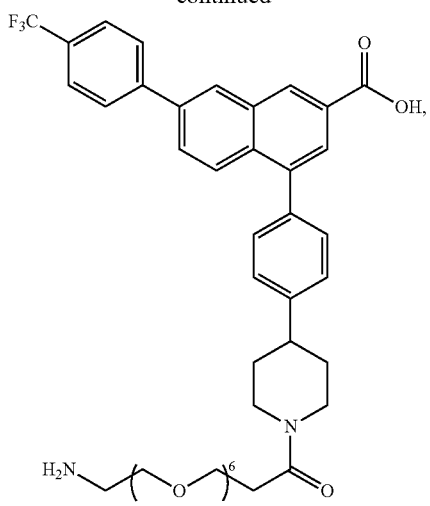
22
-continued
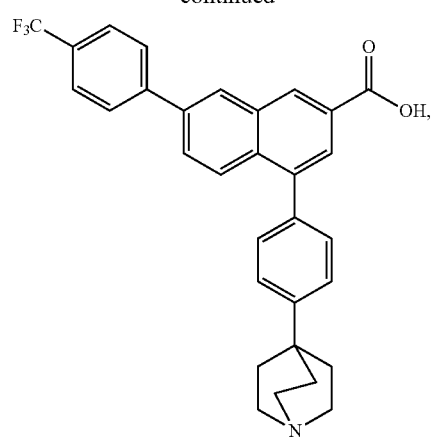
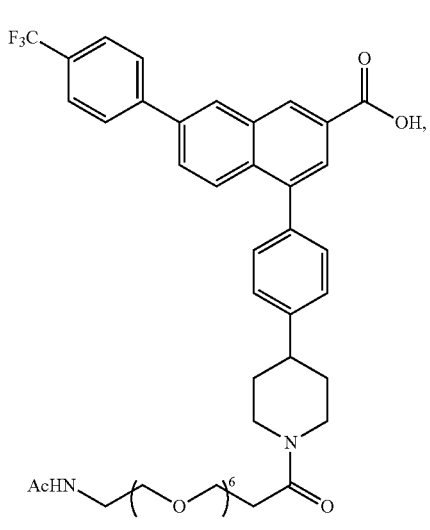
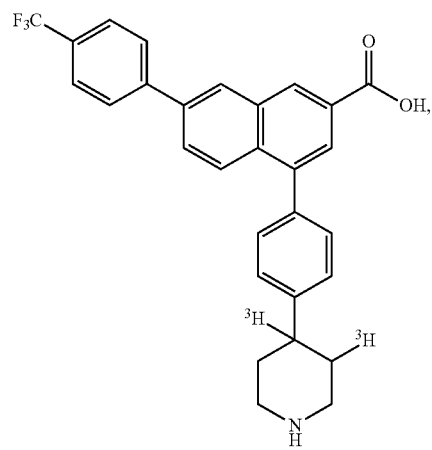
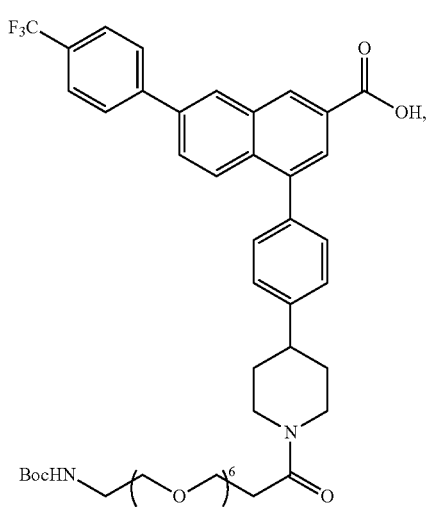
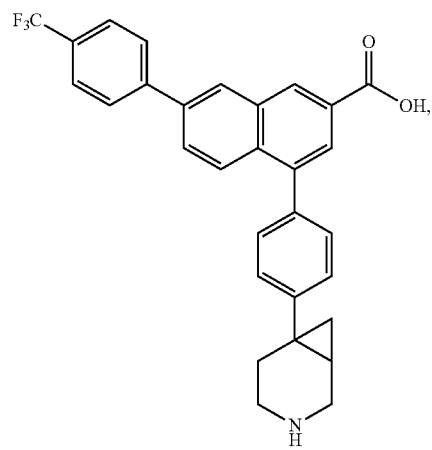

-continued
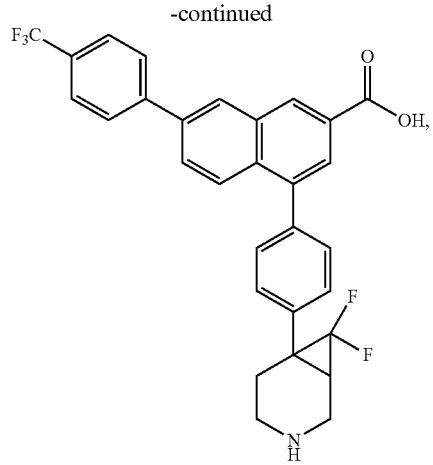
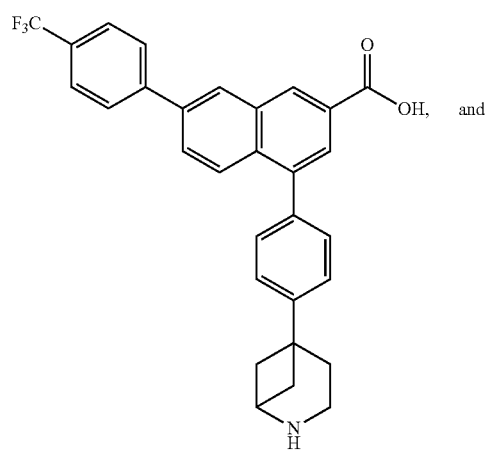 and
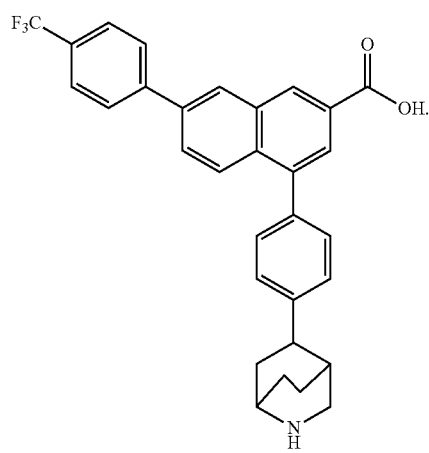
In another embodiment, the invention provides a compound of formula (II), (III), (IV), or (V):
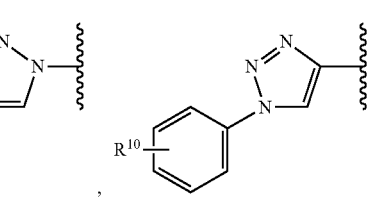
wherein $R^6$ is selected from the group consisting of
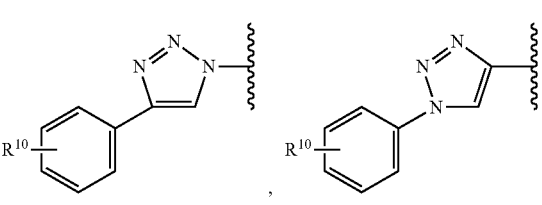

-continued
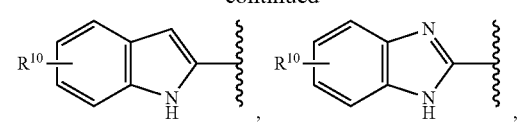
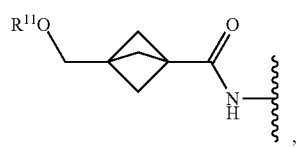
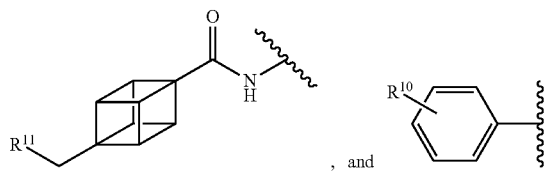
, and
R⁷ is COOH, CONH₂, CN,
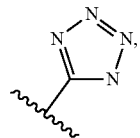 [SMILES: *c1nnn[nH]1]
or COCH₂NMe₂,
R⁸ is selected from the group consisting of C₁-C₁₀ alkyl, —CONHR₁₂R₁₃, —CONH(CH₂)ₘ—NHR₁₄R₁₅,
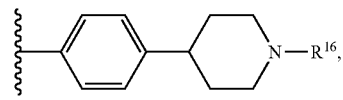
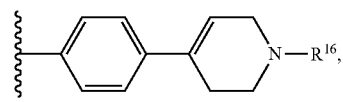
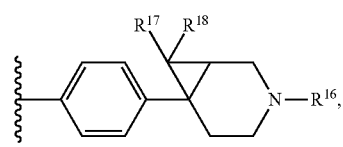
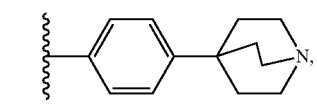
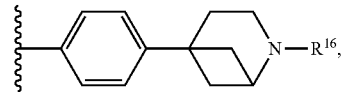
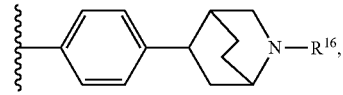
-continued
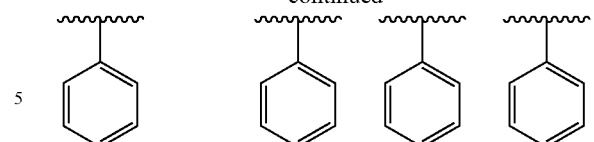
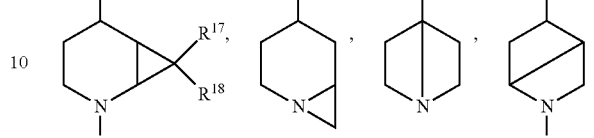
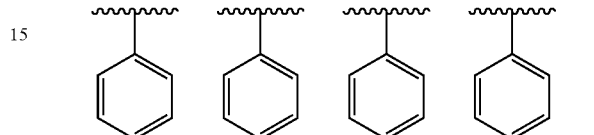
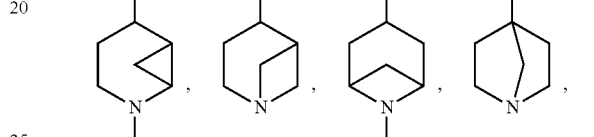
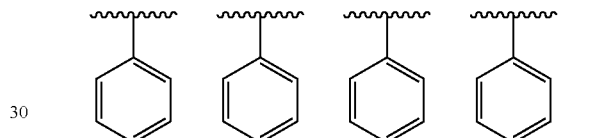
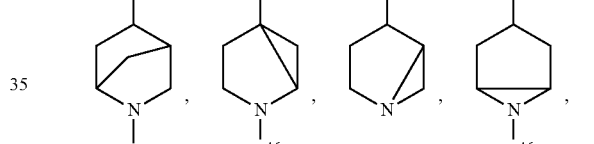
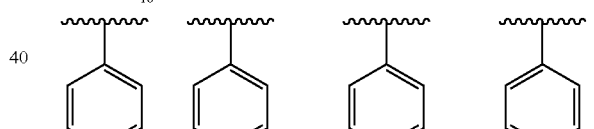
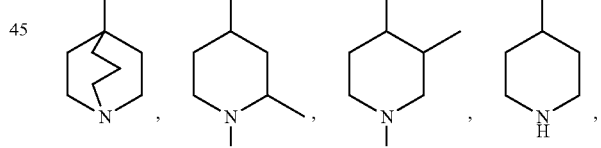
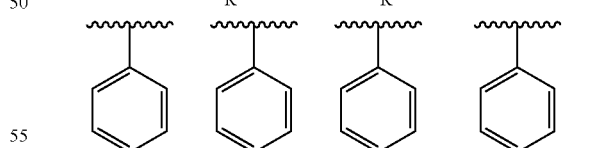
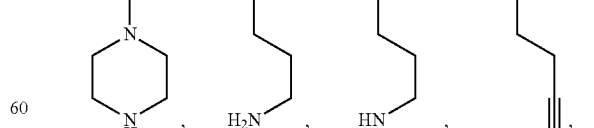
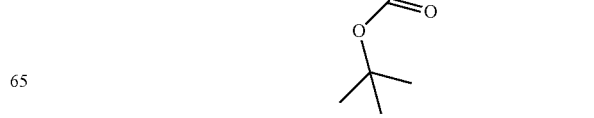

-continued
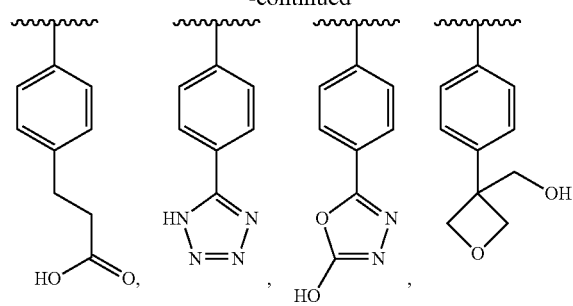
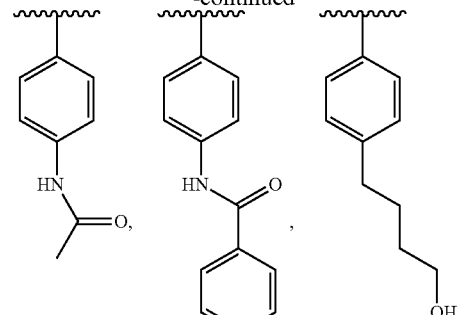
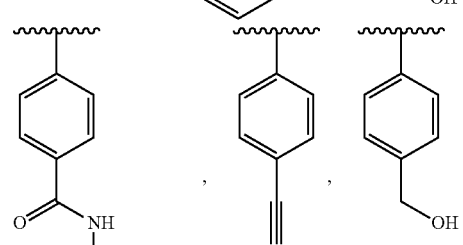
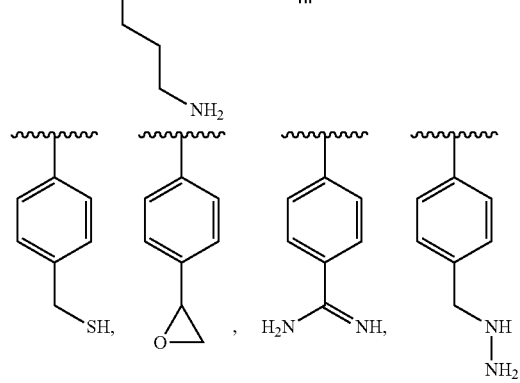
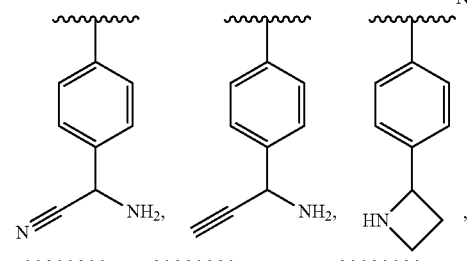
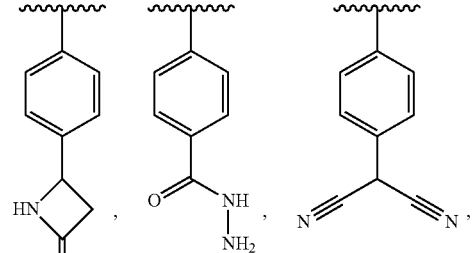
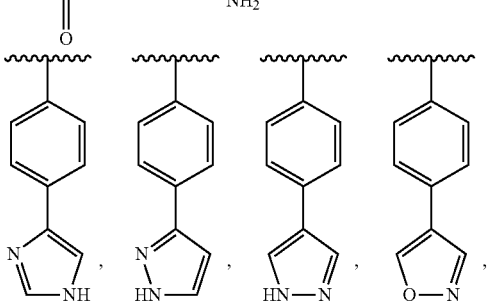

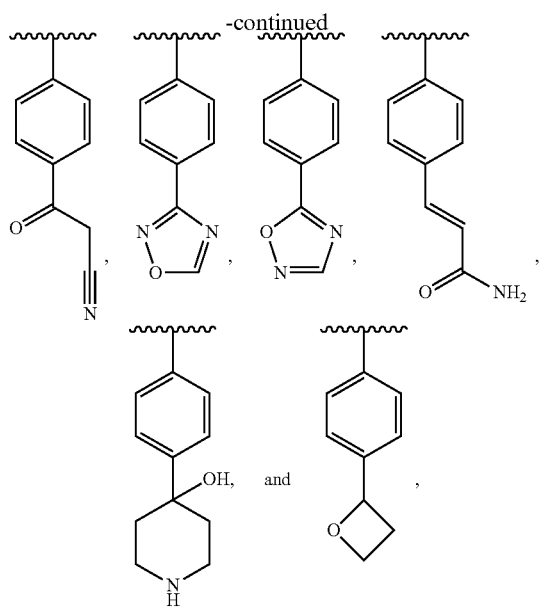

$R^{10}$ is halo or $CF_3$,
$R^{11}$ is halo, OH, or $C_1$-$C_6$ alkoxy,
$R^{12}$ and $R^{13}$ are independently H or $C_1$-$C_6$ alkyl,
$R^{14}$ and $R^{15}$ are independently H or $C_1$-$C_6$ alkyl,
$R^{16}$ is H, $C_1$-$C_{10}$ alkyl, or $C_3$-$C_{10}$ alkynyl, and
$R^{17}$ and $R^{18}$ are both H or both F,
m is an integer of from 1 to about 10,
(i) X is N, Y is CH, and Z is CH, (ii) X is CH, Y is N, and Z is CH, or (iii) X is CH, Y is CH, and Z is N,
X' and Y' are CH or N, and
Z' is N or $CR^9$ wherein $R^9$ is H or $C_1$-$C_6$ alkyl,
or a pharmaceutically acceptable salt thereof.

In certain embodiments, $R^7$ is COOH.

In certain particular embodiments, the compound is of formula (II), $R^6$ is

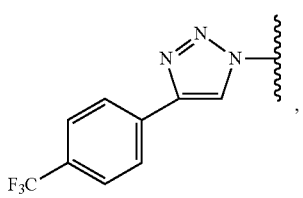 [SMILES: *n1cc(-c2ccc(C(F)(F)F)cc2)nn1]

Z' is CH, and $R^8$ is $CONH_2$ or $CONH(CH_2)_3NH_2$.

In certain particular embodiments, the compound is of formula (II), $R^6$ is

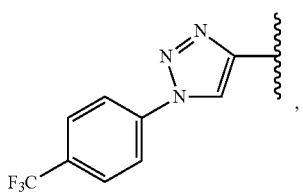

Z' is CH, and $R^8$ is $CONH_2$, $CONH(CH_2)_3NH_2$, or

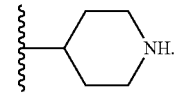

In certain particular embodiments, the compound is of formula (II), $R^6$ is

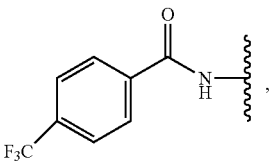 [SMILES: *NC(=O)c1ccc(C(F)(F)F)cc1]

$R^9$ is H, and $R^8$ is $CONH_2$.

In certain particular embodiments, the compound is of formula (II), $R^6$ is

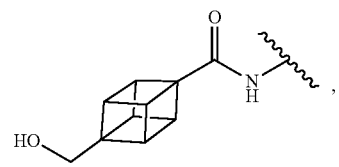 [SMILES: *NC(=O)C12C3C4C1C1C2C3C41CO]

Z' is CH, and $R^8$ is

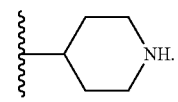

In certain particular embodiments, the compound is of formula (II), $R^6$ is

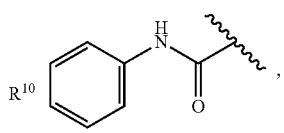

Z' is CH, and $R^8$ is $CONH_2$.

In certain particular embodiments, the compound is of formula (II), $R^6$ is

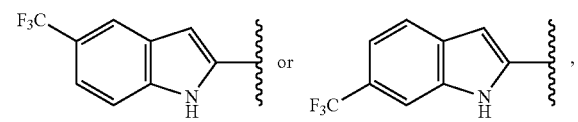 [SMILES: *c1cc2cc(C(F)(F)F)ccc2[nH]1 ; *c1cc2ccc(C(F)(F)F)cc2[nH]1]

Z' is CH and $R^8$ is $CONH_2$.

In certain particular embodiments, the compound is of formula (II), $R^6$ is

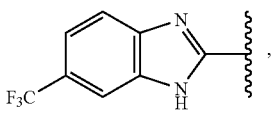

Z' is CH, and R⁸ is CONH₂.

In certain particular embodiments, the compound is of formula (III), R⁶ is

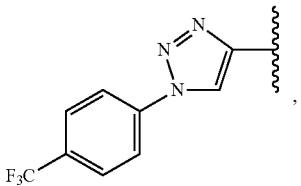 [SMILES: *c1cn(-c2ccc(C(F)(F)F)cc2)nn1]

X, Y, and Z are all C, and R⁸ is CONH(CH₂)₃NH₂.

In certain particular embodiments, the compound is of formula (IV), R⁶ is

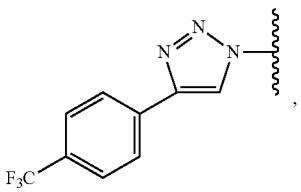 [SMILES: *n1cc(-c2ccc(C(F)(F)F)cc2)nn1]

and R⁸ is

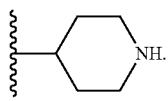 [SMILES: *C1CCNCC1]

In certain particular embodiments, the compound is of formula (II), R⁶ is

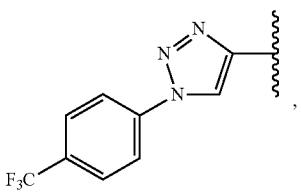 [SMILES: *c1cn(-c2ccc(C(F)(F)F)cc2)nn1]

Z' is CMe, and R⁸ is

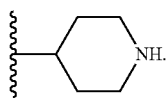 [SMILES: *C1CCNCC1]

In a further particular embodiment, the compound is of formula (V), R⁶ is 4-fluorophenyl, and R⁸ is

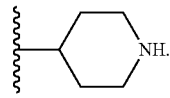

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. Suitable bicyclic heterocyclyl groups include monocylic heterocyclyl rings fused to a C₆-C₁₀ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. The term "heteroaryl" refers to a monocyclic or bicyclic 5- or 6-membered ring system as described herein, wherein the heteroaryl group is unsaturated and satisfies Hückel's rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, pyridazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl or heteroaryl group, or with benzo groups, to form a group of, for example, benzofuran.

The term "alkylcarbonyl," as used herein, refers to an alkyl group linked to a carbonyl group and further linked to a molecule via the carbonyl group, e.g., alkyl-C(=O)—. The term "alkoxycarbonyl," as used herein, refers to an alkoxy group linked to a carbonyl group and further linked to a molecule via the carbonyl group, e.g., alkyl-O—C(=O)—.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The term "metallocene" refers to a compound typically consisting of two cyclopentadienyl anions (Cp, which is $C_5H_5^-$) bound to a metal center (M) in the oxidation state II, with the resulting general formula $(C_5H_5^-)_2M$. The metal center can be Ti, V, Nb, Mo, or Fe. In a preferred embodiment, the metal center is Fe(II).

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

In any of the above embodiments, the compound or salt of formula (I), formula (II), formula (III), formula (IV), or formula (V) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess more than 60%, more than 70%, more than 80%, more than 90%, or up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess more than 60%, more than 70%, more than 80%, more than 90%, or up to 100% pure diastereomer). FIGS. 1A-1D show the structures of examples of synthetic chiral piperidine-containing intermediates useful for preparation of compounds of formulas (I)-(V).

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is ater, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The dose administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the animal or mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

In certain embodiments, the invention further provides a method for antagonizing a P2Y$_{14}$R receptor in a mammal in need thereof, comprising administering to the mammal an effective amount of a compound or salt of formulas (I)-(VI).

In certain embodiments, the invention further provides a method for treating or preventing an inflammatory condition in a mammal I need thereof, comprising administering to the mammal an effective amount of a compound or salt of formulas (I)-(VI).

In certain preferred embodiments, the inflammatory condition is selected from the group consisting of asthma, cystic fibrosis, and sterile inflammation of the kidney.

In certain embodiments, the invention further provides a compound or salt of formulas (I)-(VI) for use in antagonizing a $P2Y_{14}R$ receptor in a mammal in need thereof.

In certain embodiments, the invention further provides a compound or salt of formulas (I)-(VI) for use in treating or preventing an inflammatory condition in a mammal I need thereof.

In certain preferred embodiments, the compound is for use in treating or preventing inflammatory condition selected from the group consisting of asthma, cystic fibrosis, and sterile inflammation of the kidney.

Chemical Synthesis

Schemes 1A-1D, 2, 3A-3D, 4A-4C, and 5 depict exemplary syntheses of compound embodiments of the invention.

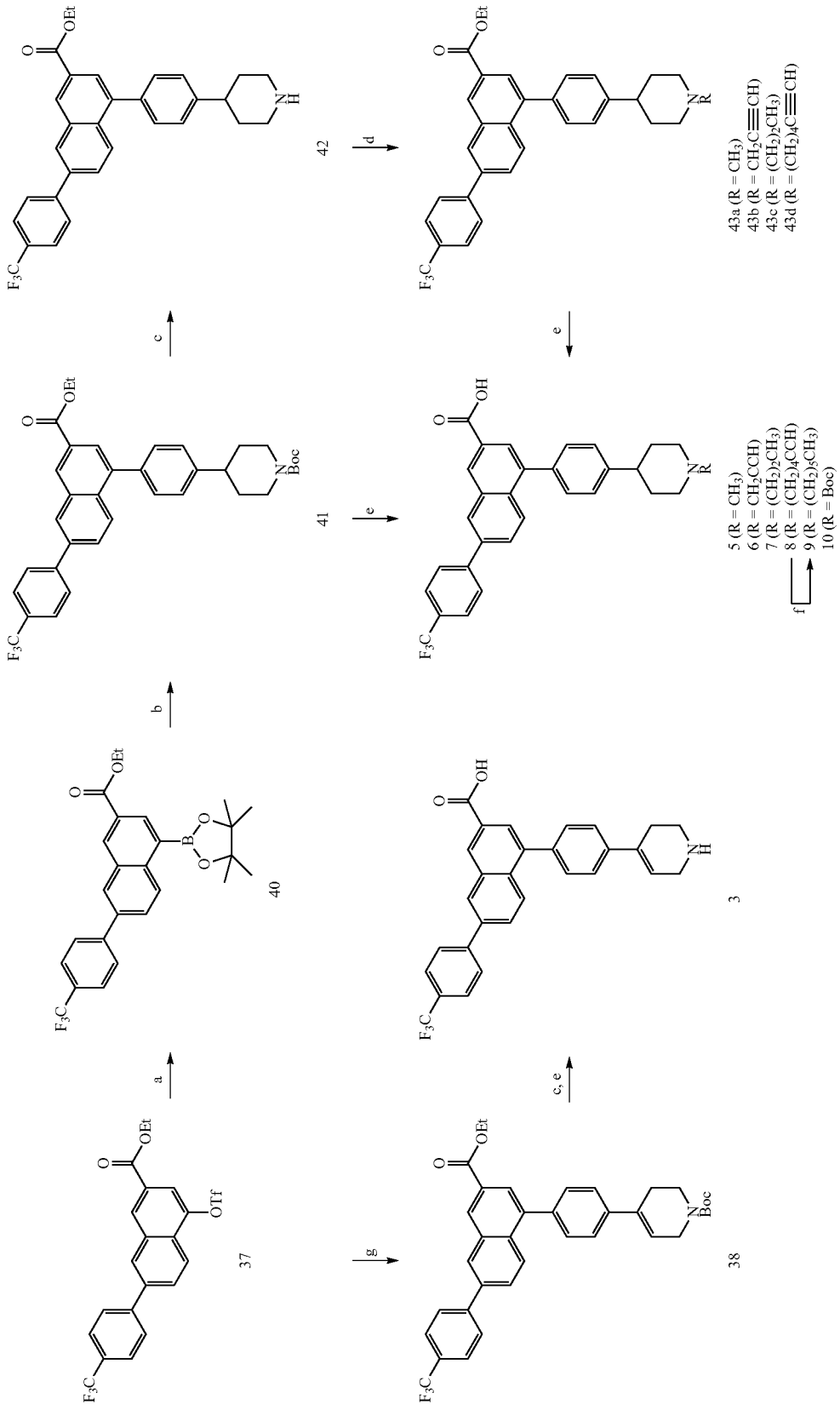

Scheme 1B
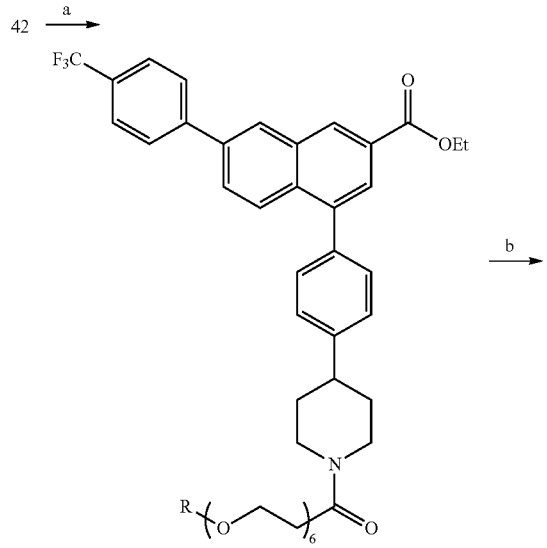
44a (R = (CH$_2$)$_2$NHBoc)
44b (R = CH$_3$)
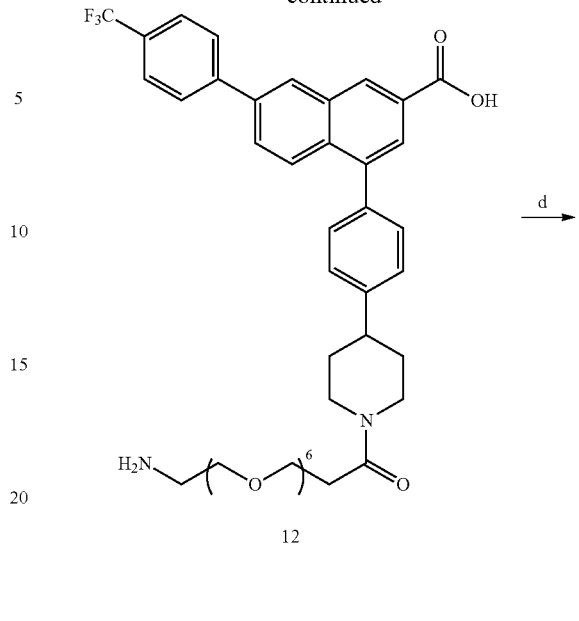
12
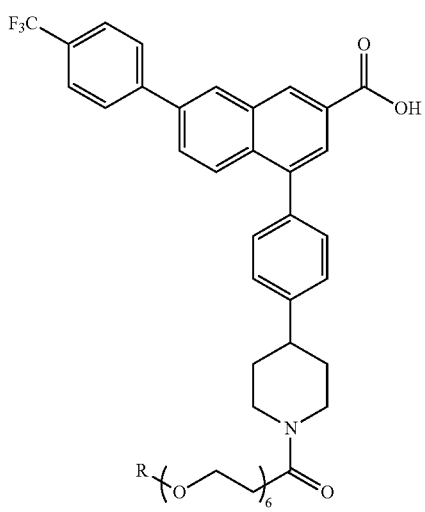
11 (R = CH$_3$)
14 (R = (CH$_2$)$_2$NHBoc)
13
1B. Reagents and Conditions: (a) Boc—NH—PEG$_6$—CH$_2$CH$_2$COOH or mPEG$_5$—CH$_2$CH$_2$COOH, HATU, DIPEA, DMF, rt, 1 h, 94% (44a) or 93% (44b); (b) KOH, MeOH, H$_2$O, 50° C., 15 h, 65% (11) or 79% (14); (c) TFA:THF = 1:1, rt, 1 h, 91%; (d) Ac$_2$O, pyr, rt, 1 h, 59%.

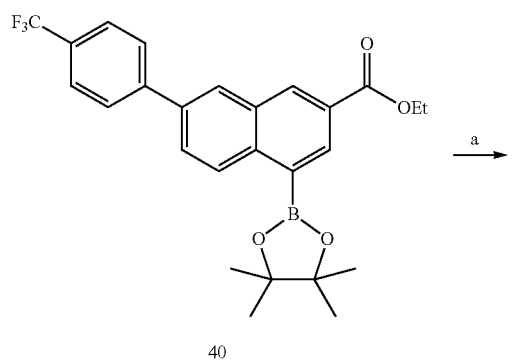
40
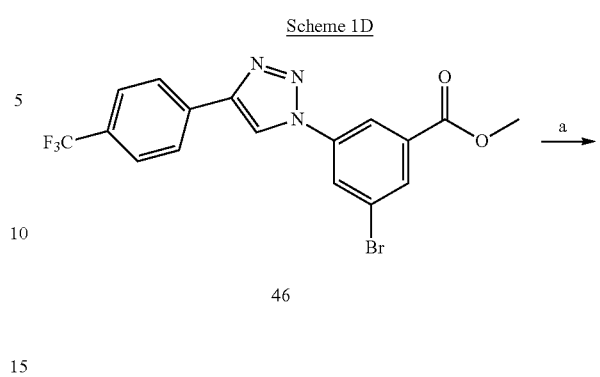
46
Scheme 1D
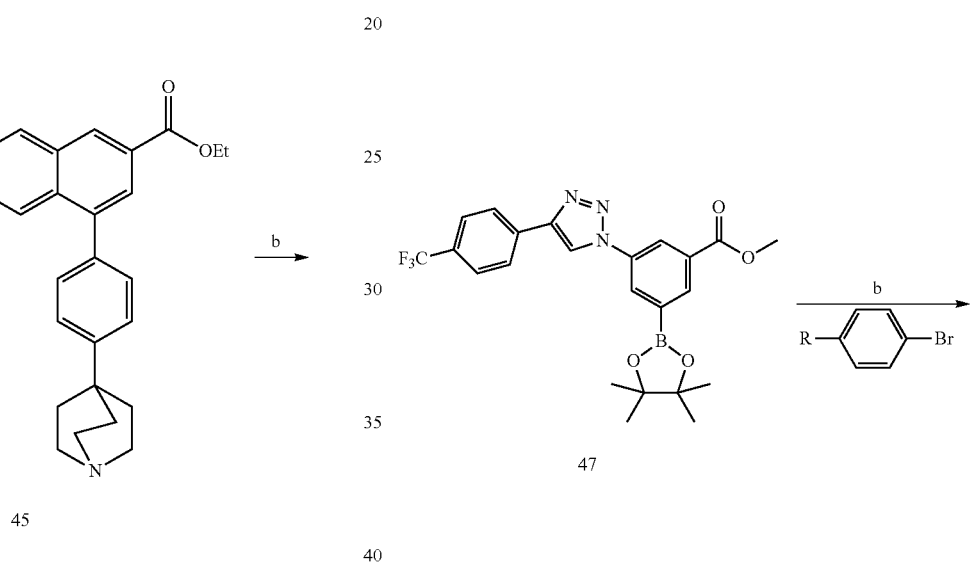
45
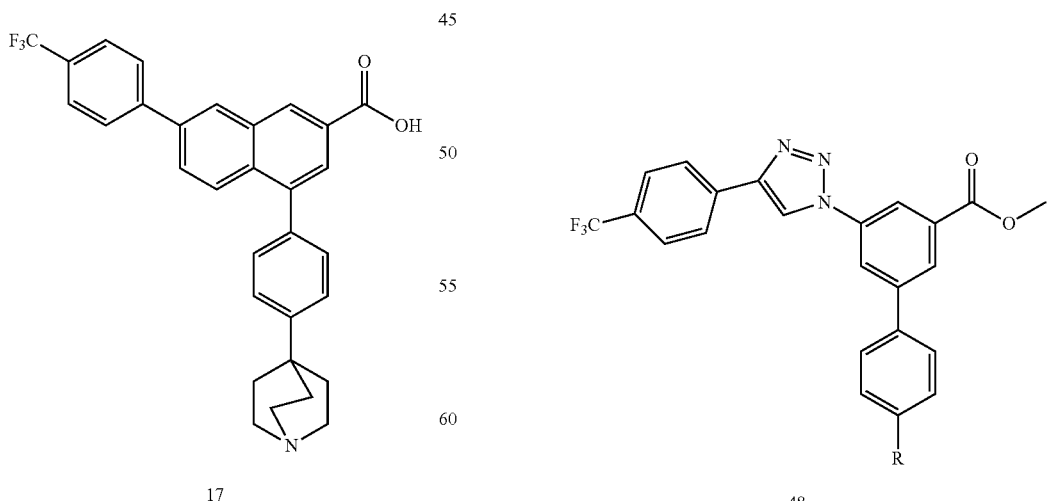
17
1C. Reagents and Conditions: (a) 4-(4-bromophenyl)quinuclidine 96, Pd(PPh$_3$)$_4$, K$_2$CO$_3$, DMF, 80° C., 3 h, 88%; b) KOH, MeOH, H$_2$O, 50° C., 12 h, 53%.

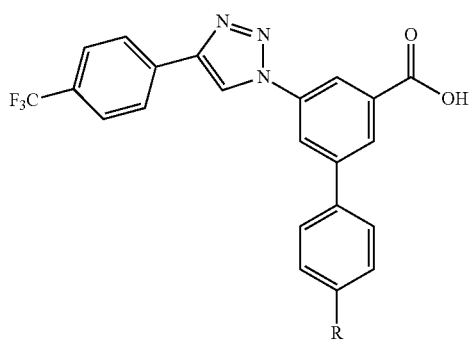

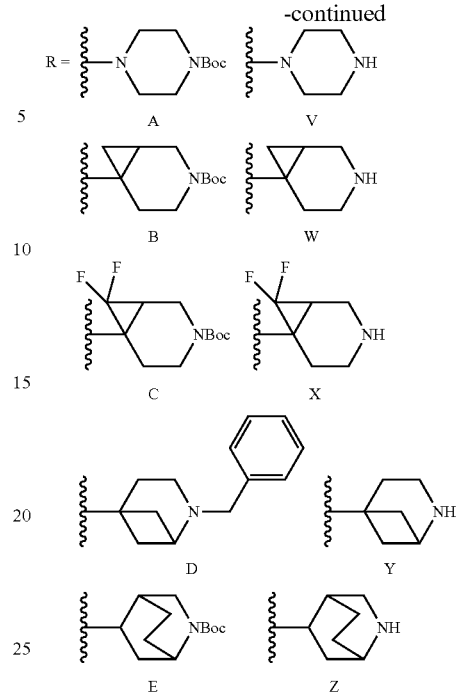

1D. Reagents and Conditions: (a) B₂pin₂, PdCl₂(dppf), KOAc, dioxane, 70° C., 15 h, 87%; (b) tert-butyl 4-(4-bromophenyl)piperidine-1-carboxylate, or 99, 101, 104 or 111, and Pd(PPh₃)₄, K₂CO₃, DMF, 80° C., 3 h, #-#%; c) KOH, MeOH, H₂O, 50° C., #-#%; (d) TFA:THF = 2:1, rt, 0.5 h, #-#%; (e) Pd/C, H₂, MeOH, EtOAc, rt, 100 psi.

Scheme 2

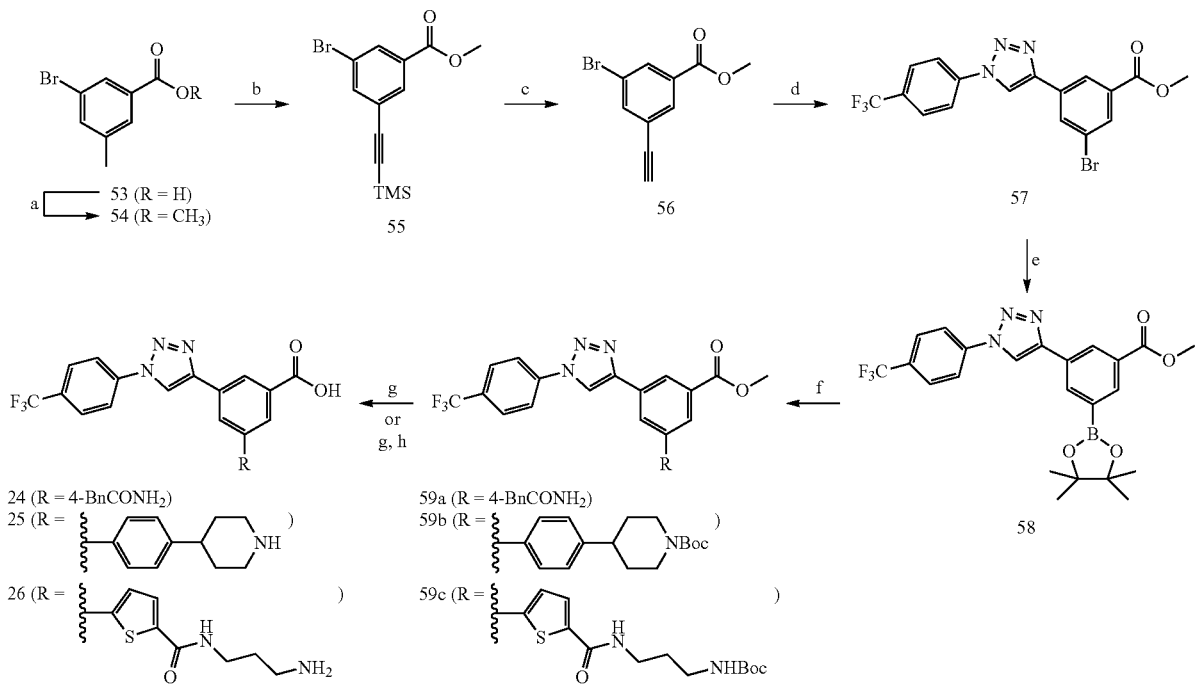

Reagents and Conditions: (a) SOCl₂, MeOH, rt, 15 h, 96%; (b) TMS-acetylene, PdCl₂(PPh₃)₂, CuI, Et₃N, DMF, rt, 5 h, 92%; (c) TBAF, THF, rt, 0.5 h, 94%; (d) 1-azido-4-(trifluoromethyl)benzene, CuSO₄·5H₂O, Na ascorbate, THF:H₂O, rt, 1 h, 46%; (e) B₂(pin)₂, KOAc, PdCl₂(dppf), dioxane, 70° C., 15 h, 76%; (f) tert-butyl 4-(4-bromophenyl)piperidine-1-carboxylate, Pd(PPh₃)₄, K₂CO₃, DMF, 85° C., 2 h for 59b (39%) or 4-BrBnCONH₂ or tert-butyl (3-(5-bromothiophene-2-carboxamido)propyl) carbamate, PdCl₂(dppf)₂, NaCO₃, DME, 50° C., 46% (59a) or 52% (59c); (g) KOH, MeOH, H₂O, 50° C., 15 h, 60-99%; (h) TFA:THF = 1:1, rt, 1 h, 61% (25) or 45% (26).

Scheme 3A
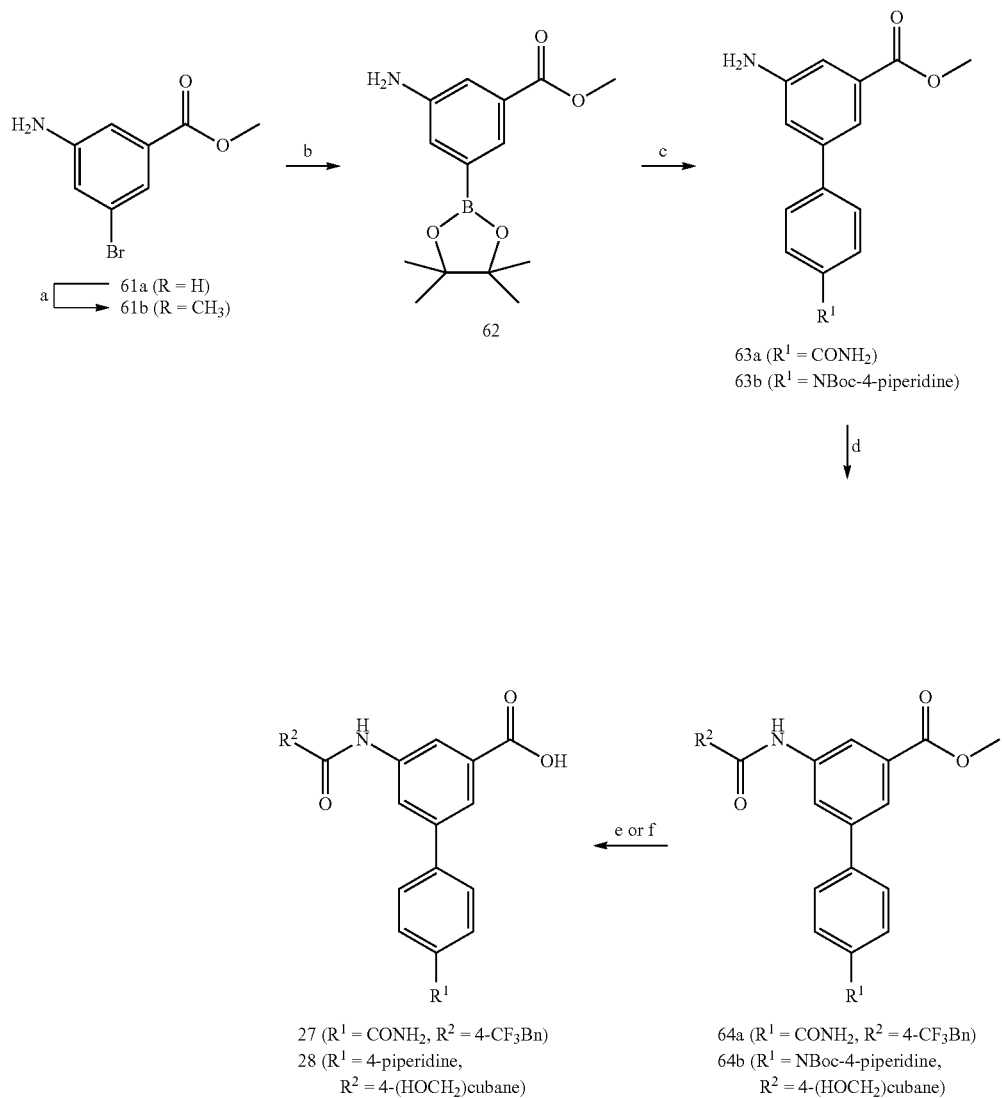
3A. Reagents and Conditions: (a) SOCl₂, MeOH, rt, 15 h, 98%; (b) B₂(pin)₂, KOAc, PdCl₂(dppf), dioxane, 95° C., 15 h, 68%; (c) 4-BrBnCONH₂ or tert-butyl 4-(4-bromophenyl)piperidine-1-carboxylate, Pd(PPh₃)₄, K₂CO₃, DMF, 80° C., 15 h, 63% (63a) or 41% (63b); (d) p-CF₃BnCOOH or 4-(HOCH₂)cubane-1-COOH, HATU, DIPEA, DMF, rt, 15 h, 99% (64a) or 69% (64b); (e) KOH, MeOH, H₂O, 50° C., 15 h, 70% for 27; (f) i) 1N HCl, dioxane, rt, 15 h, 67%; ii) KOH, MeOH, H₂O, 50° C., 15 h, 39% for 28.
Scheme 3B
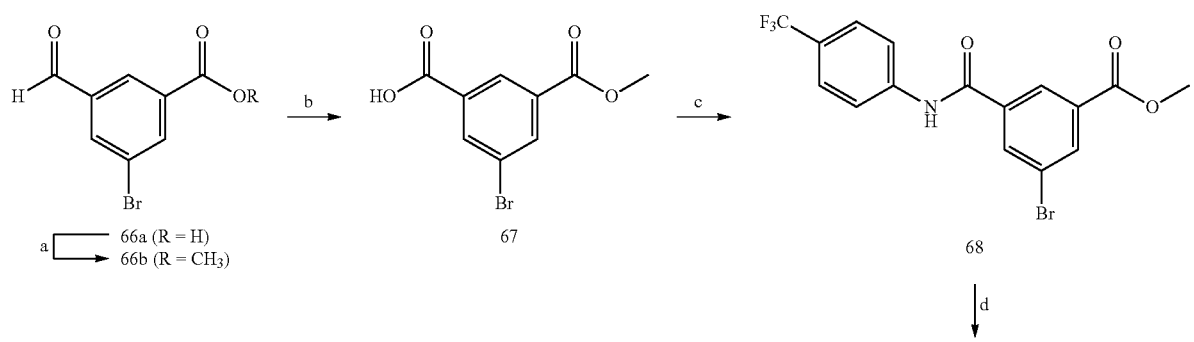

51 -continued 52

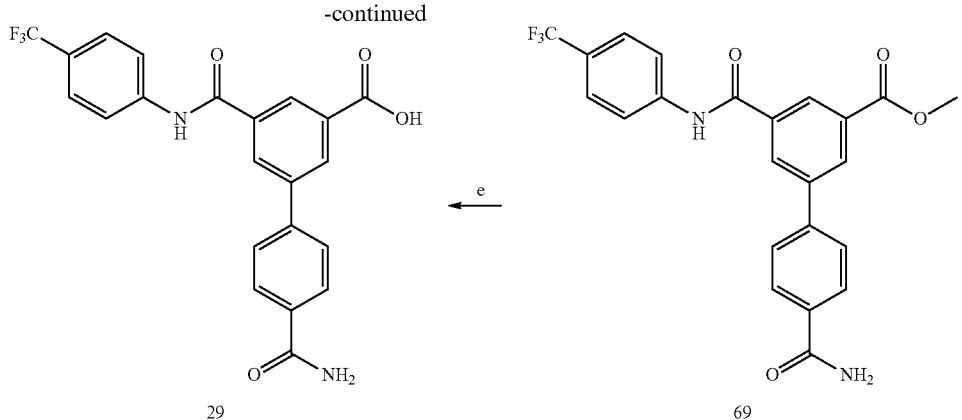

3B. Reagents and Conditions: (a) H$_2$SO$_4$, CH$_3$OH, 60° C., 15 h, 54%; (b) oxone, DMF, rt, 15 h, 78%; (c) i) SOCl$_2$, Et$_3$N, DCM, 0° C., 1 h; ii) p-trifluoromethylanilne, Et$_3$N, DCM, rt, 15 h, 45%; (d) 4-aminocarbonylphenylboronic acid pinacol ester, PdCl$_2$(PPh$_3$)$_2$, Na$_2$CO$_3$, dioxane, H$_2$O, 80° C., 2 h, 63%; (e) KOH, MeOH, H$_2$O, 50° C., 15 h, 72%.

Scheme 3C

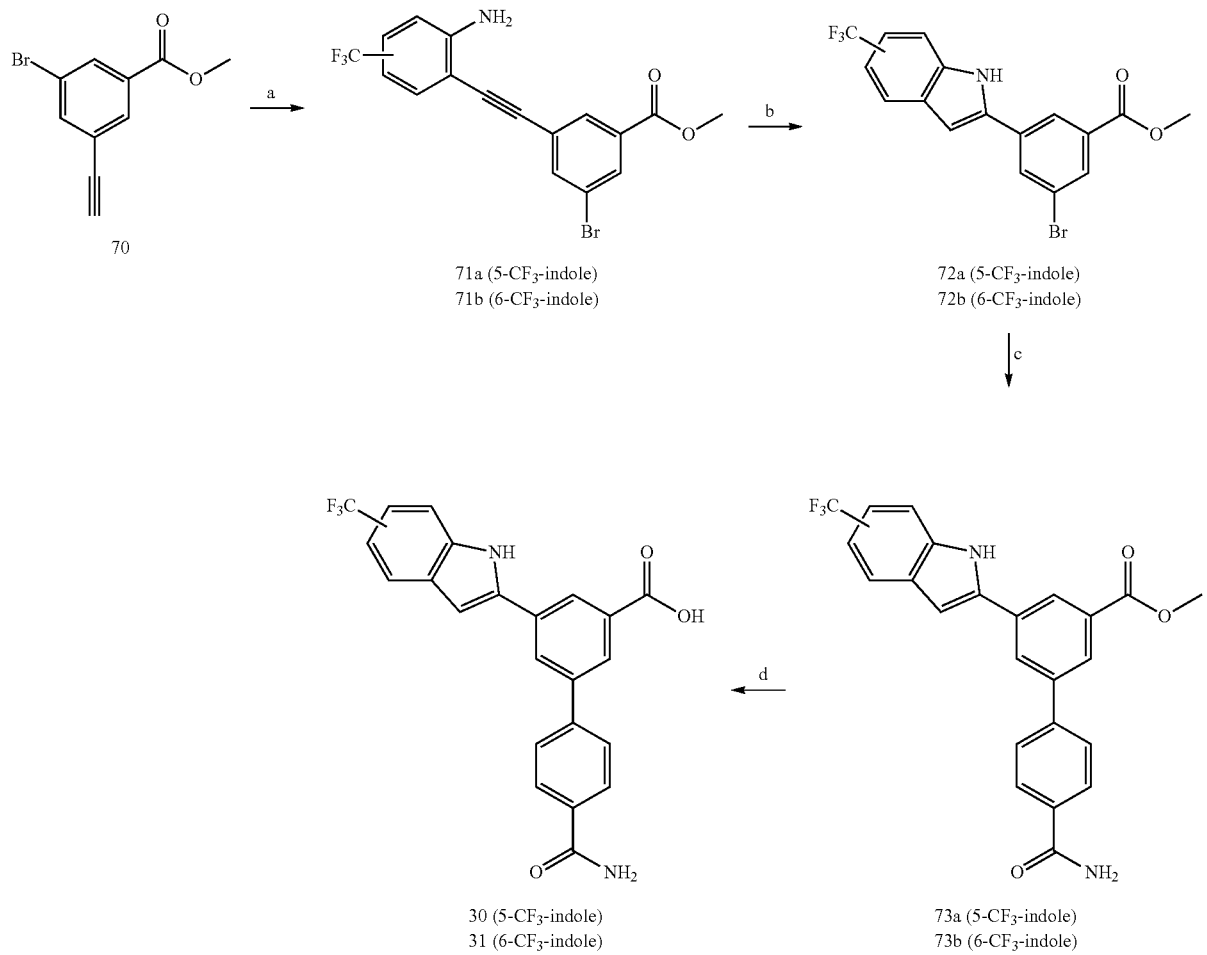

3C. Reagents and Conditions: a) iodo-(trifluoromethyl)aniline, PdCl$_2$(PPh$_3$)$_2$, CuI, Et$_3$N, rt, 1 h, 82% (71a) or 87% (71b); (b) PdCl$_2$, DMF, 110° C., 10 min, μW, 65% (72a) or 62% (72b); c) 4-aminocarbonylphenylboronic acid pinacol ester, PdCl$_2$(PPh$_3$)$_2$, Na$_2$CO$_3$, dioxane, H$_2$O, 80° C., 15 h, 55% (73a) or 72% (73b); (d) KOH, MeOH, H$_2$O, 70° C., 3 h, 59% (30) or 67% (31).

Scheme 3D
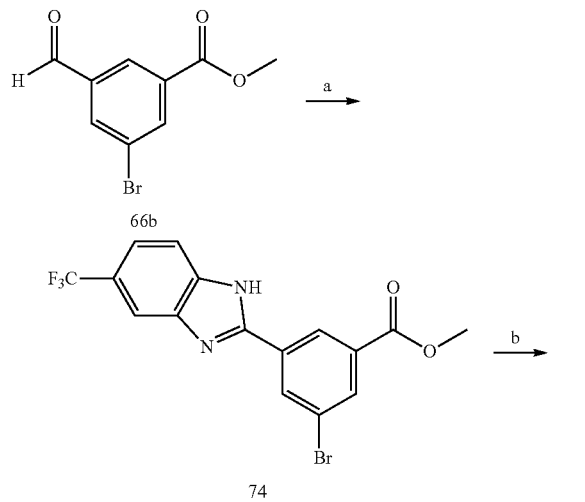
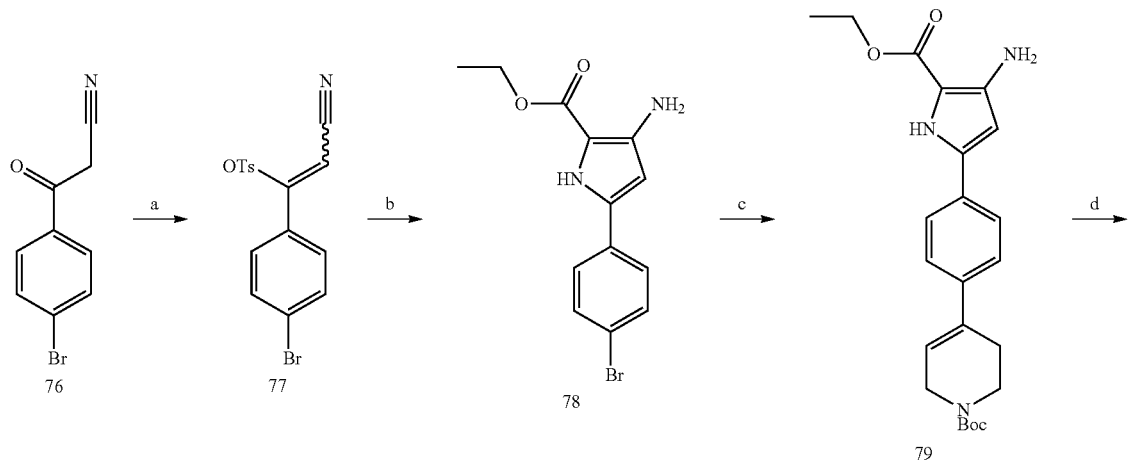
75 (R = CH₃)
32 (R = H)
3D. Reagents and Conditions: (a) Na₂S₂O₅, 4-trifluoromethyl-O-phenylenediamine, DMF, 130° C., 15 h, 97%; (b) 4-aminocarbonyl-phenylboronic acid pinacol ester, PdCl₂(PPh₃)₂, Na₂CO₃, dioxane, H₂O, 80° C., 15 h, 38%; c) KOH, MeOH, H₂O, 70° C., 3 h, 99%
Scheme 4A
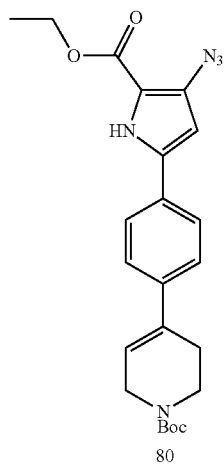

55

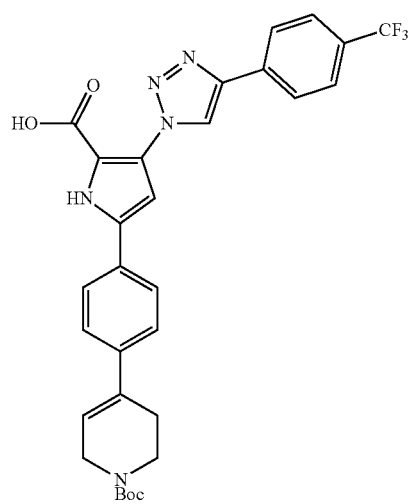

33

56

-continued

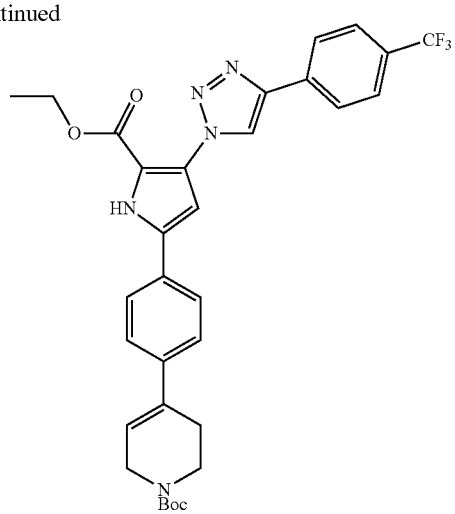

81

4A. Reagents and Conditions: (a) Ts$_2$O, TEA, DCM, rt, 3 h; (b) NaOEt, diethyl aminomalonate hydrochloride, EtOH, THF, rt, 0.5 h, 40%; (c) N-Boc-1,2,3,6-tetrahydropyridine-4-boronic acid pinacol ester, PdCl$_2$(dppf), NaOH, DMF, rt, 1 h, 78%; (d) NaNO$_2$, NaN$_3$, 4M HCl (aq), 0° C. to rt, 0.5 h, 75%; (e) 4-ethynyl-α,α,α-trifluorotoluene, sodium ascorbate, CuSO$_4$ • 5H$_2$O, dimethyl sulfoxide:water = 9:1, rt, 1 h, 77%; (f) TFA:THF = 2:1, rt, 0.5 h, 60%; (g) KOH, MeOH, H$_2$O, 50° C., 5 h, 30%.

Scheme 4B

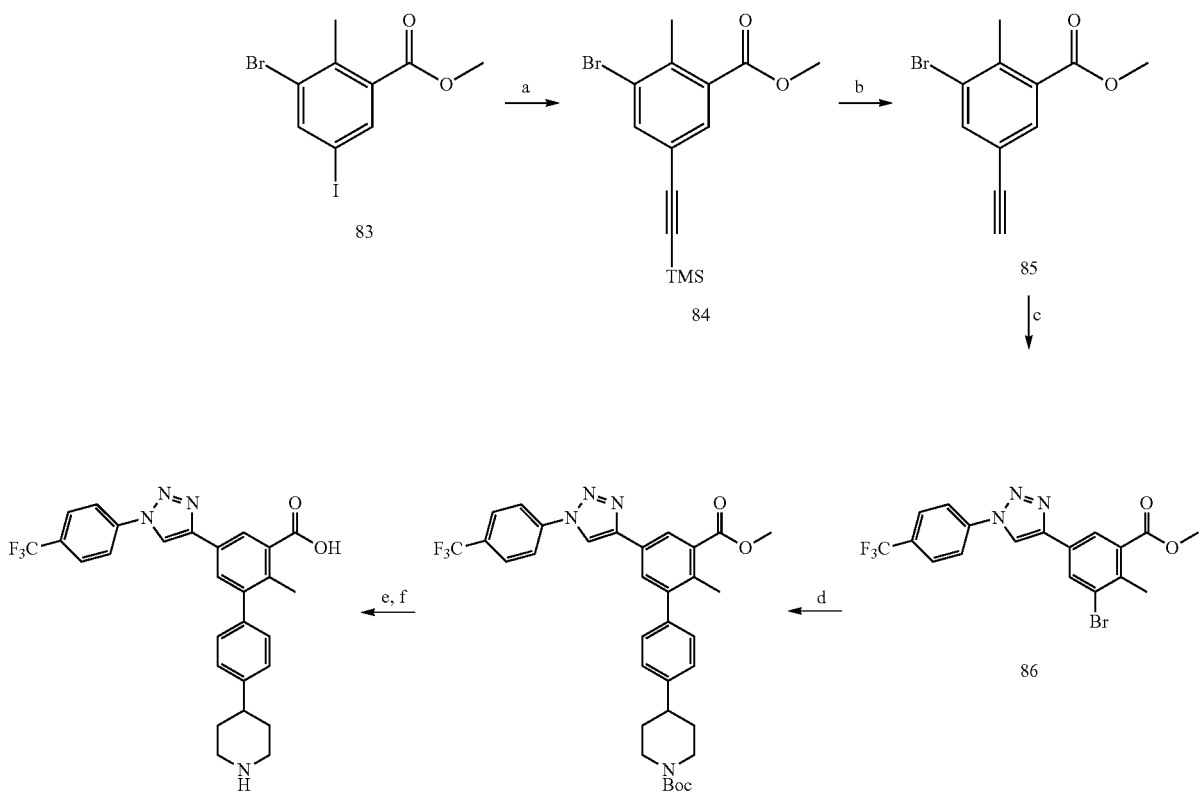

4B. Reagents and Conditions: (a) TMS-acetylene, PdCl$_2$(PPh$_3$)$_2$, CuI, Et$_3$N, DMF, rt, 5 h, 99%; (b) TBAF, THF, rt, 0.5 h, 93%; (c) 1-azido-4-(trifluoromethyl)benzene, CuSO$_4$•5H$_2$O, Na ascorbate, THF:H$_2$O, rt, 1 h, 66%; (d) tert-butyl 4-(4-(4,4,5,5-tetramethyl-1,3,2-dioxaborolan-2-yl)phenyl)piperidine-1-carboxylate, Pd(PPh$_3$)$_4$, K$_2$CO$_3$, DMF, 85% C., 12 h, 70%; (e) TFA:THF = 2:1, rt, 0.5 h, 79%; (f) KOH, MeOH, H$_2$O, 50° C., 5 h, 72%.

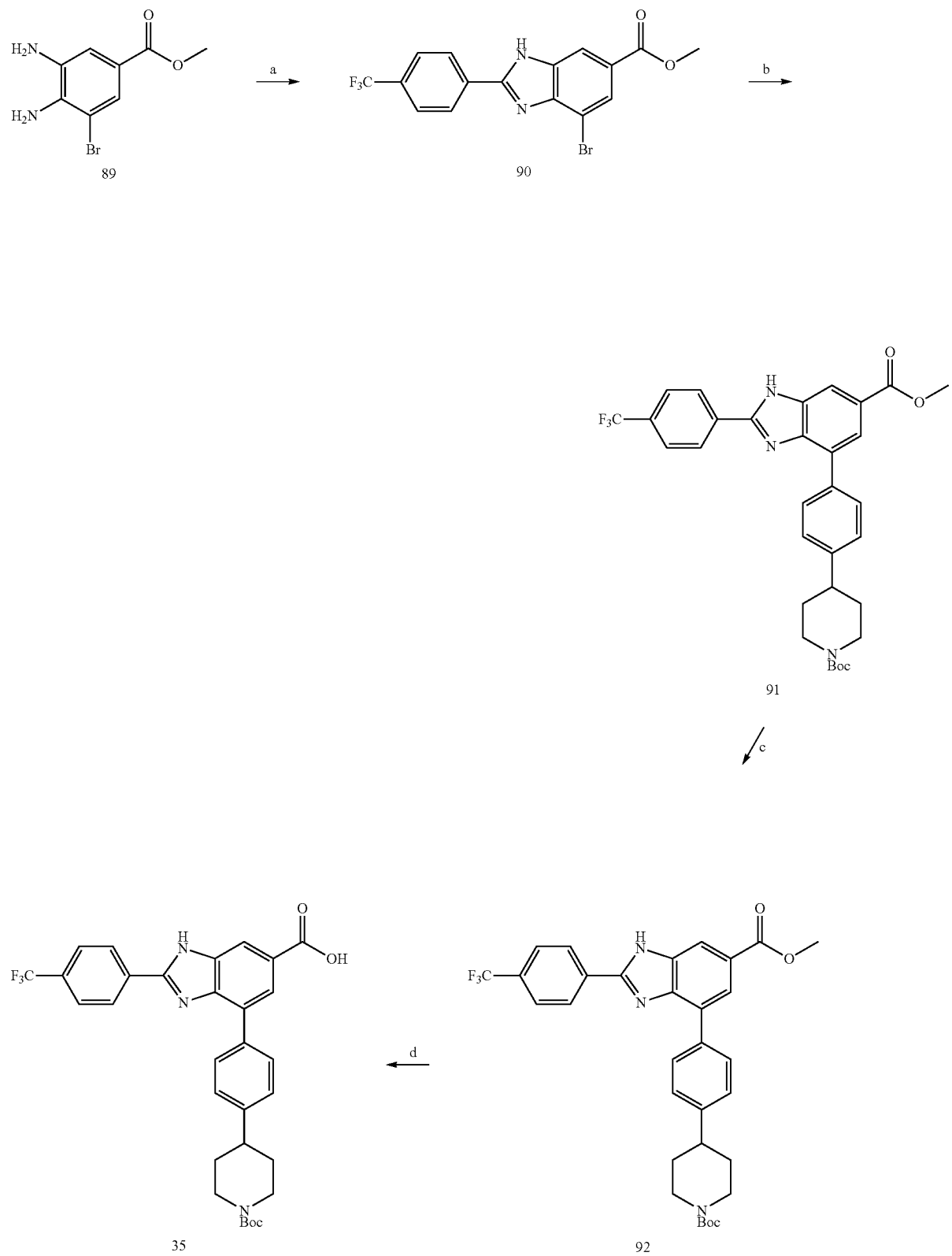
4C. Reagents and Conditions: (a) 4-(trifluoromethyl)benzaldehyde, Na$_2$S$_2$O$_5$, DMF, 130° C., 12 h, 65%; (b) tert-butyl 4-(4-(4,4,5,5-tetramethyl-1,3,2-dioxaborolan-2-yl)phenyl)piperidine-1-carboxylate, Pd(PPh$_3$)$_4$, Na$_2$CO$_3$, 1,4-dioxane:water (10:1), 80° C., 12 h, 43%; (c) TFA:THF = 2:1, rt, 0.5 h, 82%; (d) KOH, MeOH, H$_2$O, 50° C., 5 h, 63%.

Scheme 5

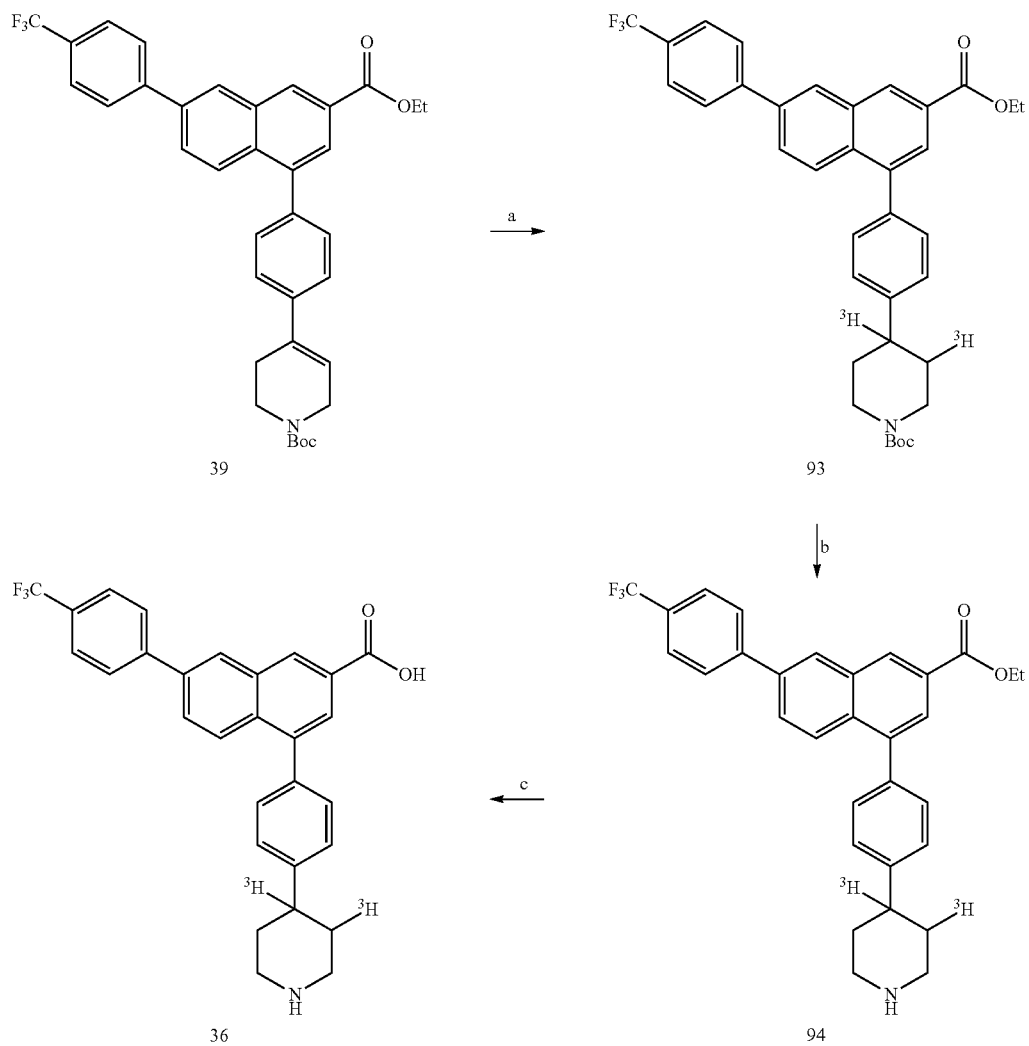

Reagents and Conditions: (a) Pd/C, ³H₂, EtOAc, rt, 100 psi; (b) TFA:THF = 2:1, rt, 0.5 h; (c) KOH, MeOH, H₂O, 50° C., 5 h.

The following examples further illustrate the invention but, of course, should not be construed as in any way limiting its scope.

Pharmacological Assays

Cell Culture: Chinese hamster ovary cells stably expressing the hP2Y$_{14}$—R (CHO-hP2Y$_{14}$R) were grown in Dulbecco's Modified Eagle's Medium (DMEM)/Ham's F12 (F12) 1:1 supplemented with 10% FBS, 100 units/mL penicillin, 100 mg/mL streptomycin, 2 mM L-glutamine and 0.500 mg/mL G418 Sulfate (Geneticin). Cells were maintained in a humidified atmosphere and sterile incubation conditions held at 37° C. and 5% $CO_2$ (g).

Competitive Assay: Competitive fluorescent assays were performed on a BD FACSCalibur flow cytometer in conjunction with the softwares BD Bioscience PlateManager and CellQuest. All cell culture growth and assays for this procedure were conducted on flat-bottom 96-well plates. CHO-hP2Y$_{14}$R cells were grown to approximately 80-90% confluency prior to assays. The 96-well plate format enabled four compounds to be analyzed in triplicate per run. All unlabeled ligand compounds are stored as 5 mM stock solutions in dimethyl sulfoxide (DMSO). Serial dilutions of each compound were prepared in complete medium. Cells were initially incubated with unlabeled compounds for 30 min at 37° C. and 5% $CO_2$ (g). Cells were then incubated with the fluorescent labeled (AlexaFluor 488) ligand MRS4174 for 30 min at a final concentration of 20 nM. After three consecutive washes in sterile 1× Dulbecco's Phosphate Buffered Saline (DPBS) minus $Ca^{2+}/Mg^{2+}$, cells were detached from the plate using Corning Cellstripper™ to reduce damaging the hP2Y$_{14}$R protein. Final cell suspensions for flow cytometry was in DPBS minus $Ca^{2+}/Mg^{2+}$.

IC$_{50}$ values were determined from the gathered data with the program GraphPad Prism version 7.0.

Reagents and instrumentation. All reagents and solvents were purchased from Sigma-Aldrich (St. Louis, Mo.), Ark Pharm, Inc. (Libertyville, Ill.; 6-bromonicotinic acid, 5-bromopicolinic acid and 5-bromopyrazine-2-carboxylic acid) and Enamine LLC (Cincinnati, Ohio; 5-bromopyrazine-2-carboxlic acid). ¹H NMR spectra were obtained with a Bruker 400 spectrometer using CDCl₃, CD₃OD, and DMSO-d₆ as solvents. Chemical shifts are expressed in δ values (ppm) with tetramethylsilane (δ 0.00) for CDCl₃ and water (δ 3.30) for CD₃OD. NMR spectra were collected with a Bruker AV spectrometer equipped with a z-gradient [$^1$H, $^{13}$C, $^{15}$N]-cryoprobe. TLC analysis was carried out on glass sheets precoated with silica gel F254 (0.2 mm) from Sigma-Aldrich. The purity of final compounds was checked using a Hewlett-Packard 1100 HPLC equipped with a Zorbax SB-Aq 5 μm analytical column (50×4.6 mm; Agilent Technologies Inc., Palo Alto, Calif.). Mobile phase: linear gradient solvent system, 5 mM tetrabutylammonium dihydrogen phosphate-CH₃CN from 100:0 to 0:100 in 15 min; the flow rate was 0.5 mL/min. Peaks were detected by UV absorption with a diode array detector at 230, 254, and 280 nm. All derivatives tested for biological activity showed >95% purity by HPLC analysis (detection at 254 nm). Low-resolution mass spectrometry was performed with a JEOL SX102 spectrometer with 6 kV Xe atoms following desorption from a glycerol matrix or on an Agilent LC/MS 1100 MSD, with a Waters (Milford, Mass.) Atlantis C18 column. High resolution mass spectroscopic (HRMS) measurements were performed on a proteomics optimized Q-TOF-2 (MicromassWaters) using external calibration with polyalanine, unless noted. Observed mass accuracies are those expected based on known instrument performance as well as trends in masses of standard compounds observed at intervals during the series of measurements. Reported masses are observed masses uncorrected for this time dependent drift in mass accuracy. cLogP was calculated using ChemDraw Professional (PerkinElmer, Boston, Mass., v. 15.0). 3b was prepared as reported.[17]

Example 1

This example demonstrates synthesis of compounds, in accordance with embodiments of the invention.

General Procedure: Deprotection Reaction

Method A: A mixture of compound (1 eq) and potassium hydroxide (5 eq) in methanol:water (2:1) was stirred at 50° C. This mixture was neutralized with 1N HCl until pH was 5-6. The slightly acidic mixture was evaporated under reduced pressure and purified by silica gel column chromatography (dichloromethane:methanol:acetic acid=95:5:0.1) or semipreparative HPLC (10 mM triethylammonium acetate buffer:acetonitrile=80:20 to 20:80 in 40 min) to afford the compound as a white solid.

Method B: A solution of compound in trifluoroacetic acid:tetrahydrofuran (1:1 or 2:1) was stirred at room temperature. The solvent was evaporated with toluene under reduced pressure. The residue was purified by silica gel column chromatography (dichloromethane:methanol=95:5) or semipreparative HPLC (10 mM triethylammonium acetate buffer:acetonitrile=80:20 to 20:80 in 40 min) to afford the compound as a white solid.

4-(4-(1,2,3,6-Tetrahydropyridin-4-yl)phenyl)-7-(4-(trifluoromethyl)phenyl)-2-naphthoic acid (3)

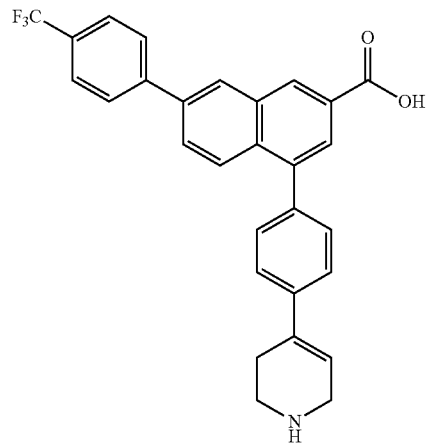

Chemical Formula: $C_{29}H_{22}F_3NO_2$
Exact Mass: 473.16
Molecular Weight: 473.50

Method A: Yield 88%; HPLC purity 95% ($R_t$=14.76 min); $^1$H NMR (400 MHz, CD₃OD) δ 8.75-8.69 (m, 1H), 8.45-8.40 (m, 1H), 8.05-7.98 (m, 3H), 7.95-7.90 (m, 1H), 7.82 (d, J=8.40 Hz, 2H), 7.70 (d, J=8.00 Hz, 1H), 7.64 (d, J=8.00 Hz, 1H), 7.58 (d, J=8.00 Hz, 1H), 7.52 (d, J=8.00 Hz, 1H), 7.37 (m, 1H), 6.23 (broad s, 1H), 3.95-3.91 (m, 1H), 3.78-3.75 (m, 1H), 3.56 (t, J=6.00 Hz, 1H), 3.25 (q, J=7.20 Hz, 1H), 2.95-2.92 (m, 1H), 2.66 (broad s, 1H); MS (ESI, m/z) 474.2 [M+1]⁺; ESI-HRMS calcd. m/z for $C_{29}H_{23}NO_2F_3$ 474.1681, found 474.1683 [M+1].

4'-(Piperazin-1-yl)-5-(4-(4-(trifluoromethyl)phenyl)-1H-1,2,3-triazol-1-yl)-[1,1'-biphenyl]-3-carboxylic acid (4)

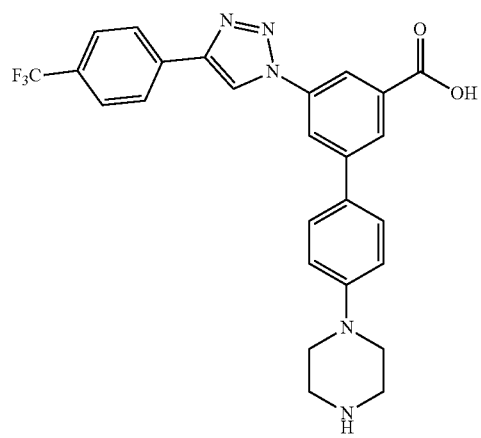

Chemical Formula: $C_{26}H_{22}F_3N_5O_2$
Exact Mass: 493.17
Molecular Weight: 493.49

Method A: Yield 59%; HPLC purity 95% ($R_t$=6.41 min); $^1$H NMR (400 MHz, CD₃OD) δ 9.17 (s, 1H), 8.45 (s, 1H), 8.37 (s, 1H), 8.23 (s, 1H), 8.16 (m, 2H), 7.81-7.75 (m, 4H), 7.20-7.14 (m, 2H), 3.51 (broad s, 4H), 3.40 (broad s, 4H); MS (ESI, m/z) 494.1 [M+1]$^+$; ESI-HRMS calcd. m/z for $C_{26}H_{23}N_5O_2F_3$ 494.1804, found 494.1807 [M+1]$^+$.

4-(4-(1-Methylpiperidin-4-yl)phenyl)-7-(4-(trifluoromethyl)phenyl)-2-naphthoic acid (5)

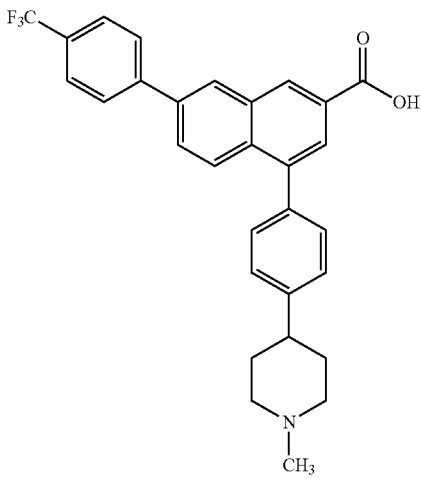

Chemical Formula: $C_{30}H_{26}F_3NO_2$
Exact Mass: 489.19
Molecular Weight: 489.54

Method A: Yield 65%; HPLC purity 95% ($R_t$=12.49 min); $^1$H NMR (400 MHz, DMSO-$d_6$) δ 8.59 (s, 1H), 8.52 (s, 1H), 8.06 (d, J=8.28 Hz, 2H), 7.96-7.86 (m, 5H), 7.46 (d, J=8.48 Hz, 2H), 7.43 (d, J 8.52 Hz, 2H), 2.93 (d, J=11.56 Hz, 2H), 2.23 (s, 3H), 2.06-2.00 (m, 2H), 1.91-1.77 (m, 4H); MS (ESI, m/z) 490.2 [M+1]$^+$; ESI-HRMS calcd. m/z for $C_{30}H_{27}NO_2F_3$ 490.1994, found 490.1988 [M+1]$^+$.

4-(4-(1-(Prop-2-yn-1-yl)piperidin-4-yl)phenyl)-7-(4-(trifluoromethyl)phenyl)-2-naphthoic acid (6)

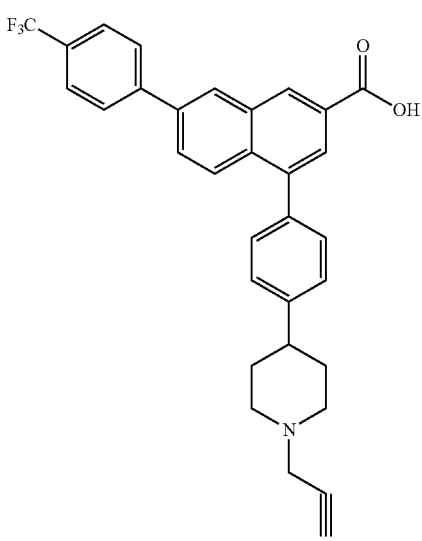

Chemical Formula: $C_{32}H_{26}F_3NO_2$
Exact Mass: 513.19
Molecular Weight: 513.56

Method A: Yield 52%; HPLC purity 99% ($R_t$=13.64 min); $^1$H NMR (400 MHz, CD$_3$OD) δ 8.72 (s, 1H), 8.41 (s, 1H), 8.06-7.98 (m, 4H), 7.91-7.89 (m, 1H), 7.80 (d, J=8.08 Hz, 2H), 7.50-7.45 (m, 4H), 3.74 (broad s, 2H), 3.45-3.42 (m, 2H), 3.05 (m, 1H), 2.88-2.80 (m, 3H), 2.15-1.94 (m, 4H); MS (ESI, m/z) 514.2 [M+1]$^+$; ESI-HRMS calcd. m/z for $C_{32}H_{27}NO_2F_3$ 514.1994, found 514.2001 [M+1]$^+$.

4-(4-(1-Propylpiperidin-4-yl)phenyl)-7-(4-(trifluoromethyl)phenyl)-2-naphthoic acid (7)

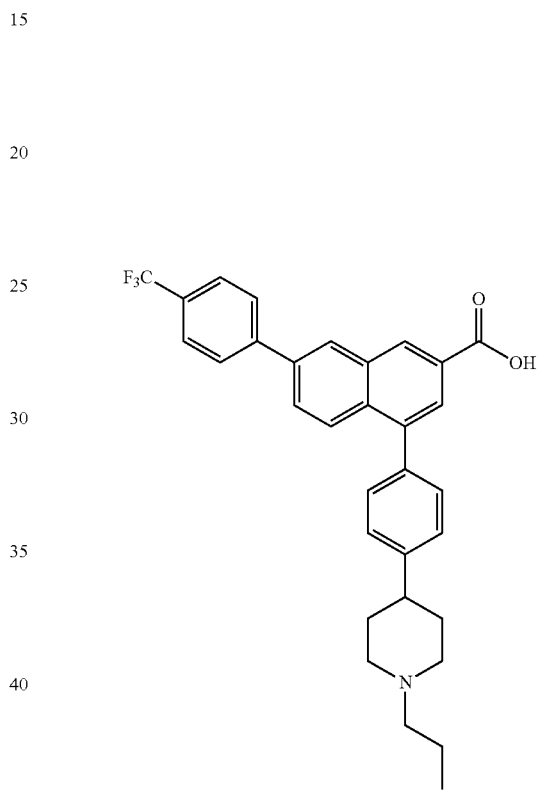

Chemical Formula: $C_{32}H_{30}F_3NO_2$
Exact Mass: 517.22
Molecular Weight: 517.59

Method A: Yield 56%; $^1$H NMR (400 MHz, CD$_3$OD) δ 8.63 (s, 1H), 8.35 (s, 1H), 8.05 (s, 1H), 7.98-7.94 (m, 3H), 7.81-7.78 (m, 3H), 7.46 (d, J=7.64 Hz, 2H), 7.41 (d, J=7.84 Hz 2H), 3.65 (d, J=11.80 Hz, 2H), 3.19-3.09 (m, 4H), 2.19-2.03 (m, 3H), 1.97 (s, 2H), 1.88-1.82 (m, 2H), 1.08 (t, J=7.32 Hz, 3H); MS (ESI, m/z) 518.2 [M+1]$^+$; ESI-HRMS calcd. m/z for $C_{32}H_{31}NO_2F_3$ 518.2307, found 518.2301 [M+1]$^+$.

4-(4-(1-(Hex-5-yn-1-yl)piperidin-4-yl)phenyl)-7-(4-(trifluoromethyl)phenyl)-2-naphthoic acid (8)

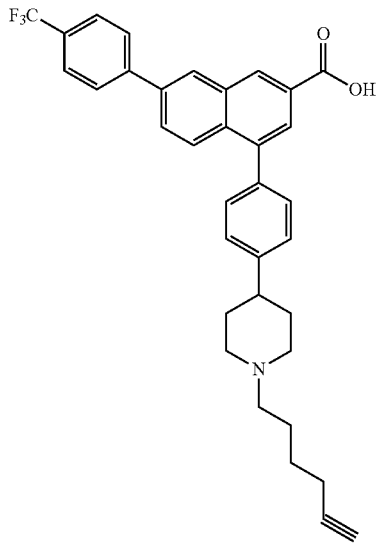

Chemical Formula: $C_{35}H_{32}F_3NO_2$
Exact Mass: 555.24
Molecular Weight: 555.64

Method A: Yield 48%.

4-(4-(1-Hexylpiperidin-4-yl)phenyl)-7-(4-(trifluoromethyl)phenyl)-2-naphthoic acid (9)

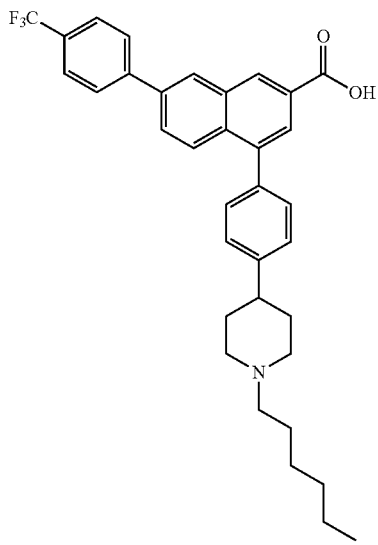

Chemical Formula: $C_{35}H_{36}F_3NO_2$
Exact Mass: 559.27
Molecular Weight: 559.67

To a solution of compound 8 (4 mg, 0.007 mmol) in methanol (0.5 mL) and ethyl acetate (0.5 mL) was added Rh/C catalyst. The resulting reaction mixture was stirred at room temperature in a hydrogen atmosphere (100 psi) for 14 h. The mixture was filtered through a cake of Celite, and the filtrate was evaporated under reduced pressure. The residue was purified by semipreparative HPLC (10 mM triethylammonium acetate buffer:acetonitrile=80:20 to 20:80 in 40 min) to afford the compound 9 (3.7 mg, 92%) as a white solid; HPLC purity 95% ($R_t$=13.98 min); $^1$H NMR (400 MHz, CD$_3$OD) δ 8.58 (s, 1H), 8.36 (s, 1H), 8.02 (s, 1H), 7.98-7.92 (m, 3H), 7.81-7.77 (m, 3H), 7.46 (d, J=8.20 Hz, 2H), 7.40 (d, J=8.16 Hz, 2H), 3.60 (d, J=11.56 Hz, 2H), 3.04-2.89 (m, 4H), 2.15-2.01 (m, 3H), 1.77-1.74 (m, 1H), 1.45-1.34 (m, 8H), 0.95 (t, J=6.80 Hz, 3H), 0.91-0.87 (m, 1H); MS (ESI, m/z) 560.3 [M+1]$^+$; ESI-HRMS calcd. m/z for $C_{35}H_{37}NO_2F_3$ 560.2776, found 560.2782 [M+1]$^+$.

4-(4-(1-(tert-butoxycarbonyl)piperidin-4-yl)phenyl)-7-(4-(trifluoromethyl)phenyl)-2-naphthoic acid (10)

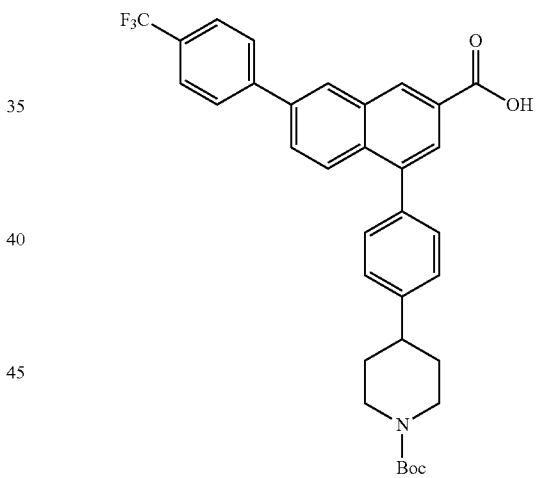

Chemical Formula: $C_{34}H_{32}F_3NO_4$
Exact Mass: 575.3
Molecular Weight: 575.63

Method A: Yield 71%; HPLC purity 95% ($R_t$=16.26 min); $^1$H NMR (400 MHz, CD$_3$OD) δ 8.74 (s, 1H), 8.43 (s, 1H), 8.05-7.99 (m, 4H), 7.93 (d, J=8.72 Hz, 1H), 7.82 (d, J=8.20 Hz, 2H), 7.48 (d, J=8.08 Hz, 2H), 7.44 (d, J=8.12 Hz, 2H), 4.28 (d, J=12.6 Hz, 2H), 2.95-2.85 (m, 3H), 1.96 (d, J=12.40 Hz, 2H), 1.77-1.685 (m, 2H), 1.52 (s, 9H); MS (ESI, m/z) 520.1 [M+1-tert-butyl]$^+$, 476.2 [M+1-Boc]$^+$.

4-(4-(1-(2,5,8,11,14,17-Hexaoxaicosan-20-oyl)piperidin-4-yl)phenyl)-7-(4-(trifluoromethyl)phenyl)-2-naphthoic acid (11)

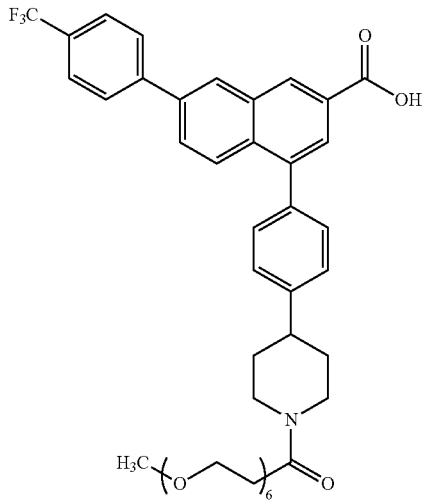

Method A: Yield 65%; HPLC purity 97% ($R_t$=14.01 min); $^1$H NMR (400 MHz, CD$_3$OD) δ 8.71 (s, 1H), 8.41 (s, 1H), 8.04-7.99 (m, 4H), 7.90 (d, J=8.92 Hz, 1H), 7.81 (d, J=8.20 Hz, 2H), 7.48 (d, J=8.16 Hz, 2H), 7.44 (d, J=8.20 Hz, 2H), 4.77 (d, J=13.22 Hz, 1H), 4.23 (d, J=13.6 Hz, 1H), 3.87-3.77 (m, 2H), 3.66-3.59 (m, 21H), 3.53-3.50 (m, 2H), 3.29-3.26 (m, 1H), 3.01-2.95 (m, 1H), 2.88-2.77 (m, 2H), 2.72-2.65 (m, 1H), 2.02 (t, J=11.88 Hz, 2H), 1.87-1.67 (m, 2H); MS (ESI, m/z) 782.4 [M+1]$^+$, 799.4 [M+NH$_4$+]$^+$; ESI-HRMS calcd. m/z for C$_{43}$H$_{51}$NO$_9$F$_3$ 782.3516, found 782.33530 [M+1]$^+$.

4-(4-(1-(1-Amino-3,6,9,12,15,18-hexaoxahenicosan-21-oyl)piperidin-4-yl)phenyl)-7-(4-(trifluoromethyl)phenyl)-2-naphthoic acid (12)

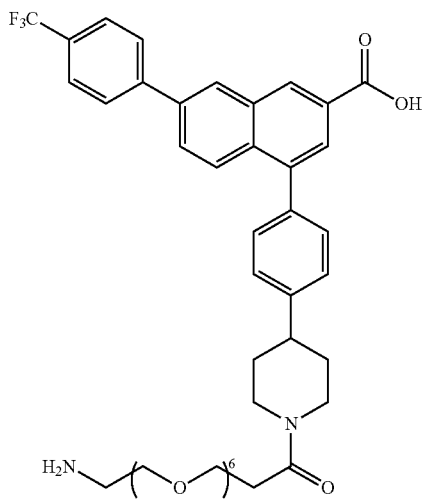

Method B: Yield 91%; $^1$H NMR (400 MHz, CD$_3$OD) δ 8.74 (s, 1H), 8.42 (s, 1H), 8.04-7.98 (m, 4H), 7.91 (d, J=8.84 Hz, 1H), 7.81 (d, J=8.20 Hz, 2H), 7.48 (d, J=8.24 Hz, 2H), 7.45 (d, J=8.32 Hz, 2H), 4.79 (d, J=12.6 Hz, 1H), 4.19 (d, J=13.4 Hz, 1H), 3.83 (t, J=6.06 Hz, 2H), 3.79 (t, J=8.08 Hz, 2H), 3.73-3.67 (m, 21H), 3.16 (t, J=4.86 Hz, 2H), 3.02-2.96 (m, 1H), 2.88-2.71 (m, 3H), 2.07-2.01 (m, 2H), 1.86-1.67 (m, 2H); MS (ESI, m/z) 811.4 [M+1]$^+$; ESI-HRMS calcd. m/z for C$_{44}$H$_{54}$N$_2$O$_9$F$_3$ 811.3781, found 811.3793 [M+1]$^+$.

4-(4-(1-(2-Oxo-6,9,12,15,18,21-hexaoxa-3-azatetracosan-24-oyl)piperidin-4-yl)phenyl)-7-(4-(trifluoromethyl)phenyl)-2-naphthoic acid (13)

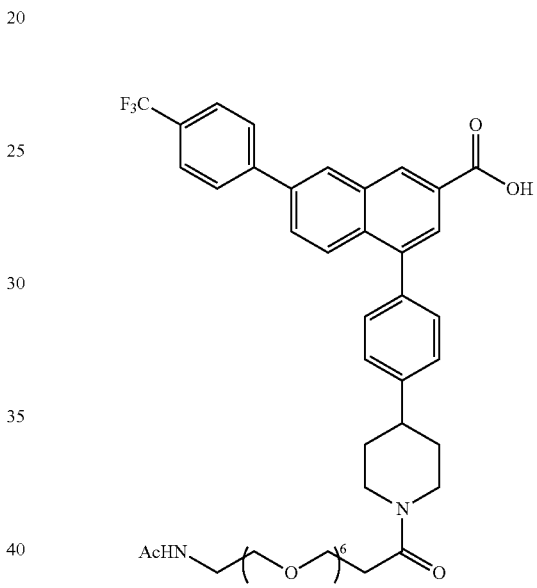

To a solution of compound 12 (6.3 mg, 7.77 μmol) in pyridine (0.5 mL) was added acetic anhydride (8 μl, 84 μmol), and then this reaction mixture was stirred at room temperature for 1 h. After all volatiles were evaporated under reduced pressure, The residue was purified by silica gel column chromatography (dichloromethane:methanol=20:1) to afford compound 13 (3.7 mg, 59%) as a white solid; HPLC purity 99% ($R_t$=13.38 min); $^1$H NMR (400 MHz, CD$_3$OD) δ 8.73 (s, 1H), 8.37 (s, 1H), 7.98-7.80 (m, 7H), 7.43 (s, 4H), 4.77 (d, J=9.04 Hz, 1H), 4.22 (d, J=11.04 Hz, 1H), 3.82 (d, J=5.24 Hz, 2H), 3.66-3.60 (m, 20H), 3.52-3.50 (m, 2H), 3.29-3.25 (m, 1H), 2.96-2.70 (m, 4H), 2.00 (m, 2H), 1.94 (s, 3H), 1.83-1.68 (m, 2H); MS (ESI, m/z) 853.4 [M+1]$^+$, 870.5 [M+NH$_4$+]$^+$; ESI-HRMS calcd. m/z for C$_{46}$H$_{56}$N$_2$O$_1$F$_3$ 853.3887, found 853.3893 [M+1]$^+$.

4-(4-(1-(2,2-Dimethyl-4-oxo-3,8,11,14,17,20,23-heptaoxa-5-azahexacosan-26-oyl)piperidin-4-yl)phenyl)-7-(4-(trifluoromethyl)phenyl)-2-naphthoicacid (14)

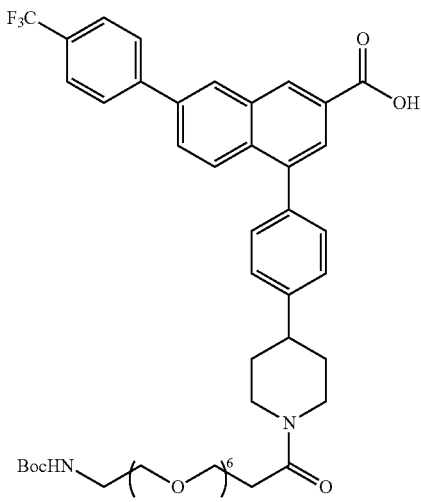

Method A: Yield 79%; HPLC purity 97% ($R_t$=14.17 min); $^1$H NMR (400 MHz, CD$_3$OD) δ 8.71 (s, 1H), 8.40 (s, 1H), 8.02-7.98 (m, 4H), 7.88 (d, J=8.92 Hz, 1H), 7.80 (d, J=8.20 Hz, 2H), 7.46 (d, J=8.20 Hz, 2H), 7.43 (d, J=8.16 Hz, 2H), 4.76 (d, J=12.6 Hz, 1H), 4.22 (d, J=12.7 Hz, 1H), 3.86-3.77 (m, 2H), 3.66-3.57 (m, 20H), 3.49 (t, J=9.52 Hz, 2H), 3.27-3.25 (m, 1H), 3.21 (t, J=5.52 Hz, 2H), 2.99-2.93 (m, 1H), 2.87-2.76 (m, 2H), 2.71-2.65 (m, 1H), 2.01 (t, J=11.82 Hz, 2H), 1.86-1.80 (m, 1H), 1.75-1.68 (m, 1H), 1.43 (s, 9H); MS (ESI, m/z) 811.4 [M+1-Boc]$^+$, 911.4 [M+1]$^+$, 928.4 [M+NH$_4$+]$^+$; ESI-HRMS calcd. m/z for C$_{49}$H$_{62}$N$_2$O$_1$F$_3$ 911.4306, found 911.4300 [M+1]$^+$.

4'-(Piperidin-4-yl)-5-(4-(4-(trifluoromethyl)phenyl)-1H-1,2,3-triazol-1-yl)-[1,1'-biphenyl]-3-carboxamide (15)

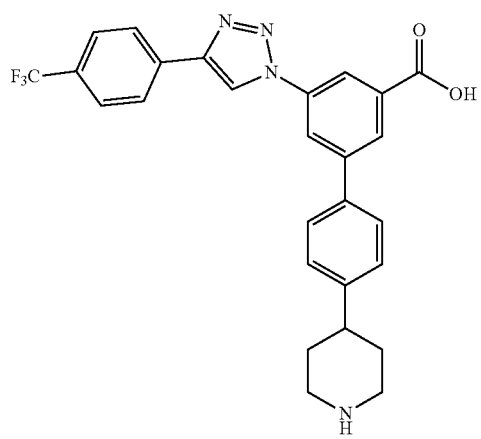

Chemical Formula: C$_{27}$H$_{24}$F$_3$N$_5$O
Exact Mass: 491.19
Molecular Weight: 491.52

Method B: Yield 72%; HPLC purity 99% ($R_t$=9.29 min); $^1$H NMR (400 MHz, CD$_3$OD) δ 9.23 (s, 1H), 8.42 (s, 1H), 8.38 (s, 1H), 8.29 (s, 1H), 8.18 (d, J=8.12 Hz, 2H), 7.83-7.80 (m, 4H), 7.48 (d, J=8.20 Hz, 2H), 3.56 (d, J=12.80 Hz, 2H), 3.22-3.15 (m, 2H), 3.06-2.98 (m, 1H), 2.17-2.14 (m, 2H), 2.03-1.92 (m, 2H); MS (ESI, m/z) 492.2 [M+1]$^+$; ESI-HRMS calcd. m/z for C$_{27}$H$_{25}$N$_5$OF$_3$ 492.2011, found 492.2013 [M+1]$^+$.

4'-(Piperidin-4-yl)-5-(4-(4-(trifluoromethyl)phenyl)-1H-1,2,3-triazol-1-yl)-[1,1'-biphenyl]-3-carbonitrile (16)

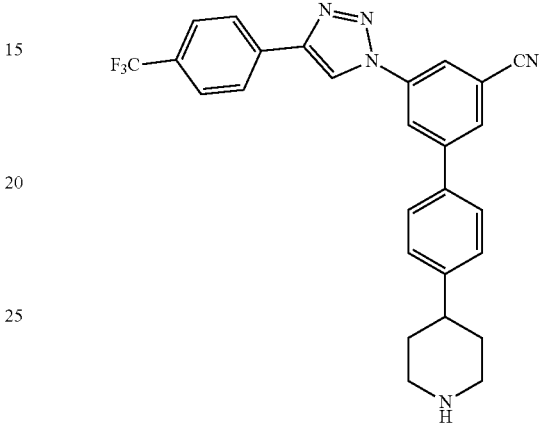

Chemical Formula: C$_{27}$H$_{22}$F$_3$N$_5$
Exact Mass: 473.18
Molecular Weight: 473.50

Method B: Yield 87%; $^1$H NMR (400 MHz, CD$_3$OD) δ 9.28 (s, 1H), 8.55 (s, 1H), 8.36 (s, 1H), 8.19-8.17 (m, 3H), 7.83-7.82 (m, 4H), 7.50 (s, 1H), 7.49 (s, 1H), 3.55 (d, J=12.4 Hz, 2H), 3.24-3.16 (m, 2H), 3.07-3.01 (m, 1H), 2.15 (d, J=13.76 Hz, 2H), 2.03-1.93 (m, 2H); MS (ESI, m/z) 474.2 [M+1]$^+$; ESI-HRMS calcd. m/z for C$_{27}$H$_{23}$N$_5$F$_3$ 474.1906, found 474.1912 [M+1]$^+$.

4-(4-(Quinuclidin-4-yl)phenyl)-7-(4-(trifluoromethyl)phenyl)-2-naphthoic acid (17)

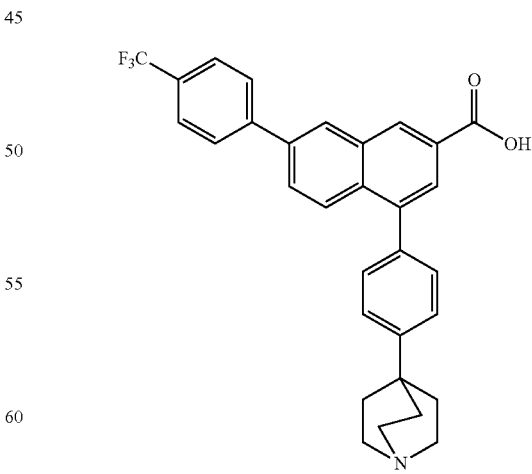

Chemical Formula: C$_{31}$H$_{26}$F$_3$NO$_2$
Exact Mass: 501.19
Molecular Weight: 501.55

Method A: Yield 53%; HPLC purity 99% ($R_t$=3.44 min); $^1$H NMR (400 MHz, CD$_3$OD) δ 8.76 (s, 1H), 8.43 (s, 1H), 8.01-7.92 (m, 5H), 7.82-7.80 (m, 2H), 7.65-7.54 (m, 4H), 3.58-3.54 (m, 6H), 2.37-2.33 (m, 6H); MS (ESI, m/z) 502.2 [M+1]$^+$; ESI-HRMS calcd. m/z for C$_{31}$H$_{27}$NO$_2$F$_3$ 502.1994, found 502.1993 [M+1]$^+$.

4'-(3-Azabicyclo[4.1.0]heptan-6-yl)-5-(4-(4-(trifluoromethyl)phenyl)-1H-1,2,3-triazol-1-yl)-[1,1'-biphenyl]-3-carboxylic acid (18)

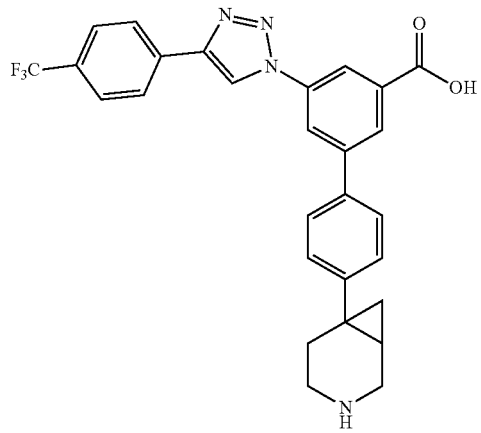

Chemical Formula: C$_{28}$H$_{23}$F$_3$N$_4$O$_2$
Exact Mass: 504.18
Molecular Weight: 504.51

Method B: Yield 79%; HPLC purity 99% ($R_t$=24.09 min); $^1$H NMR (400 MHz, CD$_3$OD) δ 9.09 (s, 1H), 8.45 (s, 1H), 8.34 (s, 1H), 8.17 (s, 1H), 8.13-8.04 (m, 2H), 7.75-7.63 (m, 4H), 7.50-7.40 (m, 2H), 3.83-3.77 (m, 1H), 3.30-3.22 (m, 2H), 2.94-2.87 (m, 1H), 2.35 (broad s, 2H), 1.60-1.56 (m, 1H), 1.31-1.23 (m, 1H), 1.12-1.10 (m, 1H); MS (ESI, m/z) 505.2 [M+1]$^+$; ESI-HRMS calcd. m/z for C$_{28}$H$_{24}$N$_4$O$_2$F$_3$ 505.1851, found 505.1848 [M+1]$^+$.

4'-(7,7-Difluoro-3-azabicyclo[4.1.0]heptan-6-yl)-5-(4-(4-(trifluoromethyl)phenyl)-1H-1,2,3-triazol-1-yl)-[1,1'-biphenyl]-3-carboxylic acid (19)

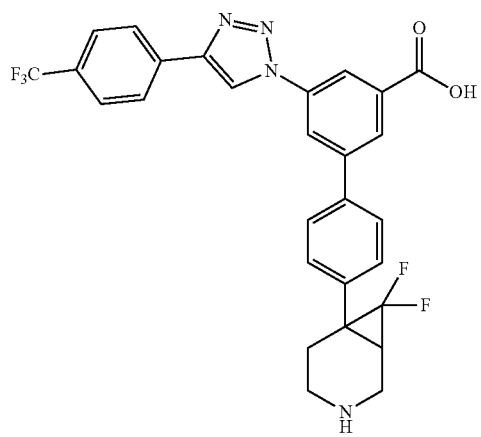

Chemical Formula: C$_{28}$H$_{21}$F$_5$N$_4$O$_2$
Exact Mass: 540.16
Molecular Weight: 540.49

Method B:

4'-(2-Azabicyclo[3.1.1]heptan-5-yl)-5-(4-(4-(trifluoromethyl)phenyl)-1H-1,2,3-triazol-1-yl)-[1,1'-biphenyl]-3-carboxylic acid (20)

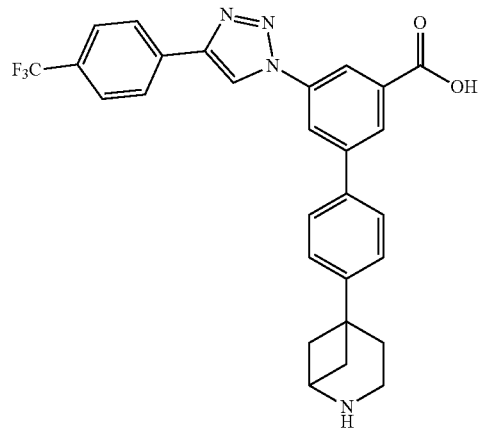

Chemical Formula: C$_{28}$H$_{23}$F$_3$N$_4$O$_2$
Exact Mass: 504.18
Molecular Weight: 504.51

To a solution of compound 49d (mg, mmol) in methanol (0.5 mL) and ethyl acetate (0.5 mL) was added Pd/C catalyst. The resulting reaction mixture was stirred at room temperature in a hydrogen atmosphere (100 psi) for 14 h. The mixture was filtered through a cake of Celite, and the filtrate was evaporated under reduced pressure. The residue was purified by silica gel column chromatography (dichloromethane:methanol:acetic acid=10:1:0.01) to afford compound 20 (mg, %) as a white solid.

4'-(2-Azabicyclo[2.2.2]octan-5-yl)-5-(4-(4-(trifluoromethyl)phenyl)-1H-1,2,3-triazol-1-yl)-[1,1'-biphenyl]-3-carboxylic acid (21)

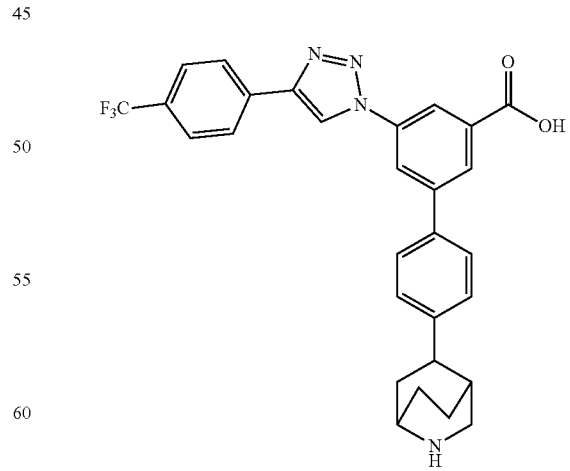

Chemical Formula: C$_{29}$H$_{25}$F$_3$N$_4$O$_2$
Exact Mass: 518.19
Molecular Weight: 518.54

Method B:

4'-Carbamoyl-5-(1-(4-(trifluoromethyl)phenyl)-1H-1,2,3-triazol-4-yl)-[1,1'-biphenyl]-3-carboxylic acid (24)

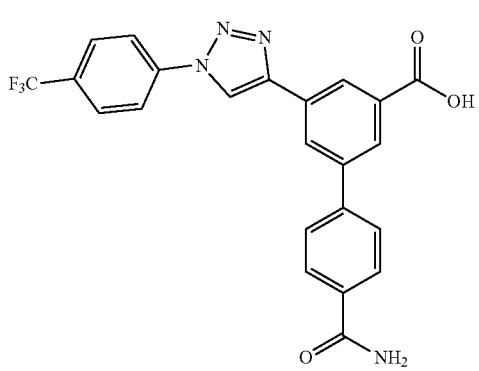

Chemical Formula: $C_{23}H_{15}F_3N_4O_3$
Exact Mass: 452.11
Molecular Weight: 452.39

Method A: Yield 88%; HPLC purity 99% ($R_t$=11.77 min); $^1$H NMR (400 MHz, CD$_3$OD) δ 9.28 (s, 1H), 8.64 (s, 1H), 8.51 (s, 1H), 8.35 (s, 1H), 8.21 (d, J=8.40 Hz, 2H), 8.04 (d, J=8.28 Hz, 2H), 7.96 (d, J=8.52 Hz, 2H), 7.88 (d, J=8.24 Hz, 2H); MS (ESI, m/z) 453.1 [M+1]$^+$; ESI-HRMS calcd. m/z for $C_{23}H_{16}N_4O_3F_3$ 453.1175 found 453.1169 [M+1]$^+$.

4'-(Piperidin-4-yl)-5-(1-(4-(trifluoromethyl)phenyl)-1H-1,2,3-triazol-4-yl)-[1,1'-biphenyl]-3-carboxylic acid (25)

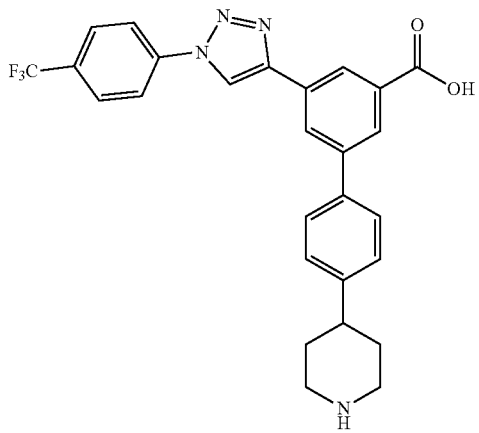

Chemical Formula: $C_{27}H_{23}F_3N_4O_2$
Exact Mass: 492.18
Molecular Weight: 492.50

Method B: Yield 61%; HPLC purity 95% ($R_t$=11.17 min); $^1$H NMR (400 MHz, CD$_3$OD) δ 9.18 (s, 1H), 8.43 (s, 1H), 8.34 (s, 1H), 8.28 (s, 1H), 8.23 (d, J=8.52 Hz, 2H), 7.96 (d, J=8.56 Hz, 2H), 7.73 (d, J=8.16 Hz, 2H), 7.39 (d, J=8.12 Hz, 2H), 3.19 (d, J=12.28 Hz, 2H), 2.82-2.74 (m, 3H), 2.67 (s, 3H; OAc salt), 1.89 (d, J=8.24 Hz, 2H), 1.80-1.70 (m, 2H); MS (ESI, m/z) 493.2 [M+1]$^+$; ESI-HRMS calcd. m/z for $C_{27}H_{24}N_4O_2F_3$ 493.1851, found 493.1856 [M+1]$^+$.

3-(5-((3-Aminopropyl)carbamoyl)thiophen-2-yl)-5-(1-(4-(trifluoromethyl)phenyl)-1H-1,2,3-triazol-4-yl) benzoic acid (26)

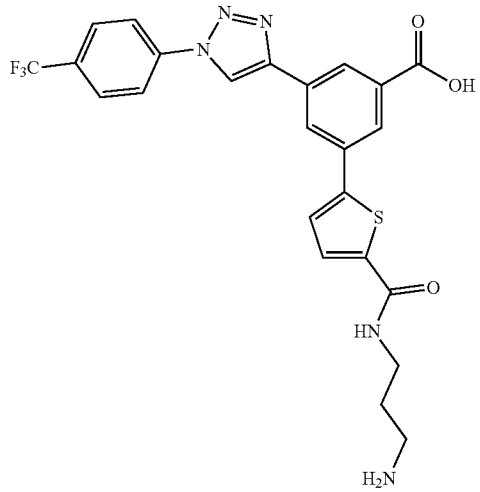

Chemical Formula: $C_{24}H_{20}F_3N_5O_3S$
Exact Mass: 515.12
Molecular Weight: 515.51

Method B: Yield 45%; HPLC purity 98% ($R_t$=10.23 min); $^1$H NMR (400 MHz, DMSO-d$_6$) δ 9.75 (s, 1H), 8.82 (broad s, 1H; NH), 8.53 (s, 1H), 8.46 (s, 1H), 8.25 (d, J=8.44 Hz, 2H), 8.23 (s, 1H), 8.06 (d, J=8.52 Hz, 2H), 7.89 (s, 1H), 7.75 (d, J=3.36 Hz, 1H), 3.35 (merged with water peak), 2.90 (t, J=7.24 Hz, 2H), 1.84 (t, J=7.02 Hz, 2H); MS (ESI, m/z) 516.1 [M+1]$^+$; ESI-HRMS calcd. m/z for $C_{24}H_{21}N_5O_3F_3{}^{32}S$, 516.1317 found 516.1316 [M+1]$^+$.

4'-Carbamoyl-5-(4-(trifluoromethyl)benzamido)-[1,1'-biphenyl]-3-carboxylic acid (27)

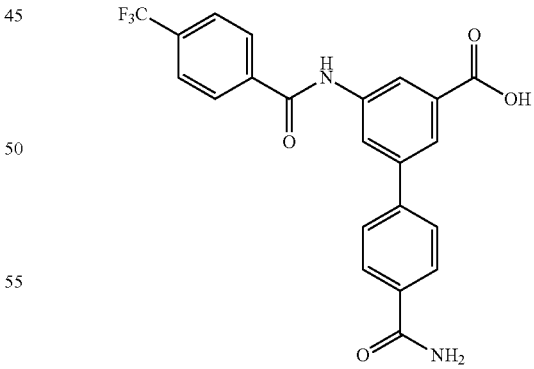

Chemical Formula: $C_{22}H_{15}F_3N_2O_4$
Exact Mass: 428.10
Molecular Weight: 428.37

Method A: Yield 70%; HPLC purity 96% ($R_t$=11.11 min) $^1$H NMR (400 MHz, CD$_3$OD) δ 8.42 (s, 1H), 8.37 (s, 1H), 8.17 (d, J=7.96 Hz, 2H), 8.14 (s, 1H), 8.02 (d, J=7.76 Hz, 2H), 7.86 (d, J=7.96 Hz, 2H), 7.81 (d, J=7.80 Hz, 2H); MS (ESI, m/z) 429.1 [M+1]$^+$; ESI-HRMS calcd. m/z for $C_{22}H_{16}N_2O_4F_3$ 429.1062, found 429.1069 [M+1]$^+$.

5-(4-(Hydroxymethyl)cubane-1-carboxamido)-4'-(piperidin-4-yl)-[1,1'-biphenyl]-3-carboxylic acid (28)

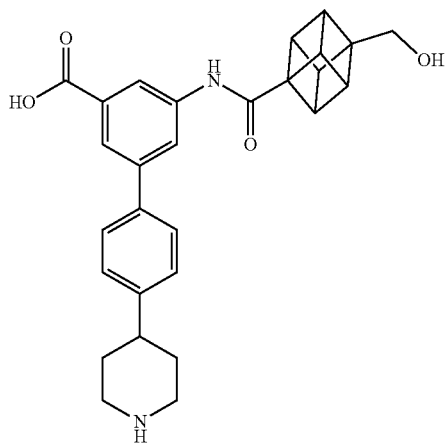

Chemical Formula: $C_{28}H_{28}N_2O_4$
Exact Mass: 456.20
Molecular Weight: 456.54

Method A: Yield 39%; HPLC purity 96% ($R_t$=7.39 min); $^1$H NMR (400 MHz, DMSO-d$_6$) δ 9.69 (s, 1H), 8.13 (s, 2H), 7.90 (s, 1H), 7.57 (d, J=7.88 Hz, 2H), 7.35 (d, J=7.96 Hz, 2H), 4.15 (t, J=4.68 Hz, 3H), 3.80 (t, J=4.50 Hz, 3H), 3.55 (s, 2H), 3.20 (d, J=11.76 Hz, 2H), 2.79-2.75 (m, 2H), 1.80-1.76 (m, 3H); MS (ESI, m/z) 457.2 [M+1]$^+$; ESI-HRMS calcd. m/z for $C_{28}H_{29}N_2O_4$ 457.2127, found 457.2129 [M+1]$^+$.

4'-Carbamoyl-5-((4-(trifluoromethyl)phenyl)carbamoyl)-[1,1'-biphenyl]-3-carboxylic acid (29)

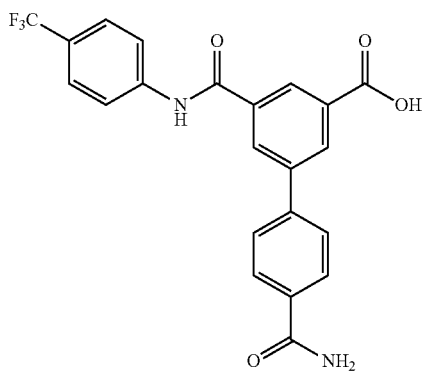

Chemical Formula: $C_{22}H_{15}F_3N_2O_4$
Exact Mass: 428.10
Molecular Weight: 428.37

Method A: Yield 72%; HPLC purity 99% ($R_t$=11.30 min) 1H NMR (400 MHz, CD$_3$OD) δ 8.61 (s, 1H), 8.53 (s, 1H), 8.44 (s, 1H), 8.03 (d, J=8.12 Hz, 2H), 7.99 (d, J=8.48 Hz, 2H), 7.87 (d, J=8.12 Hz, 2H), 7.68 (d, J=8.48 Hz, 2H); MS (ESI, m/z) 429.1 [M+1]$^+$; ESI-HRMS calcd. m/z for $C_{22}H_{16}N_2O_4F_3$ 429.1062, found 429.1065 [M+1]$^+$.

4'-Carbamoyl-5-(5-(trifluoromethyl)-1H-indol-2-yl)-[1,1'-biphenyl]-3-carboxylic acid (30)

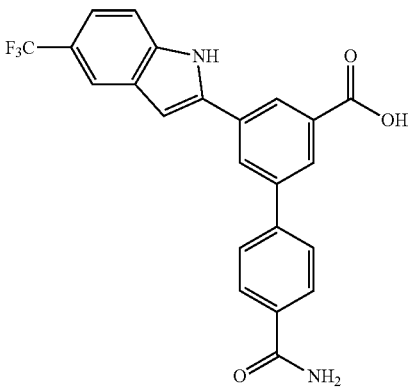

Chemical Formula: $C_{23}H_{15}F_3N_2O_3$
Exact Mass: 424.10
Molecular Weight: 424.38

The suspension of compound 73a (8 mg, 18.2 μmol) and potassium hydroxide (5.2 mg, 91.2 μmol) in methanol (1 mL) and water (0.5 mL) was stirred at 70° C. for 3 h. The reaction mixture was acidified with acetic acid, and the solvent was evaporated under reduced pressure. The residue was purified by silica gel column chromatography (dichloromethane:methanol:acetic acid=10:1:0.01) to afford compound 30 (4.6 mg, 59%) as a white solid; HPLC purity 96% ($R_t$=11.75 min); (96%); $^1$H NMR (400 MHz, CD$_3$OD) δ 8.62 (s, 1H), 8.34 (s, 1H), 8.29 (s, 1H), 8.05 (d, J=7.84 Hz, 2H), 7.93 (s, 1H), 7.89 (d, J=7.92 Hz, 2H), 7.58 (d, J=8.48 Hz, 1H), 7.40 (d, J=8.44 Hz, 1H), 7.14 (s, 1H); MS (ESI, m/z) 425.1 [M+1]$^+$; ESI-HRMS calcd. m/z for $C_{23}H_{16}N_2O_3F_3$ 425.1113, found 425.1112 [M+1]$^+$.

4'-Carbamoyl-5-(6-(trifluoromethyl)-1H-indol-2-yl)-[1,1'-biphenyl]-3-carboxylic acid (31)

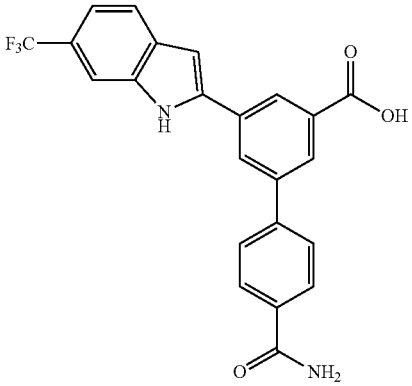

Chemical Formula: $C_{23}H_{15}F_3N_2O_3$
Exact Mass: 424.10
Molecular Weight: 424.38

Compound 73b (20 mg, 50.2 µmol) was converted to compound 31 (13 mg, 67%) as a white solid, using similar procedure used in the preparation of compound 30; HPLC purity 97% ($R_t$=11.94 min); $^1$H NMR (400 MHz, CD$_3$OD) δ 8.54 (s, 1H), 8.38 (s, 1H), 8.31 (s, 1H), 8.06 (d, J=8.24 Hz, 2H), 7.90 (d, J=8.28 Hz, 2H), 7.75-7.74 (m, 2H), 7.30 (d, J=8.64 Hz, 1H), 7.12 (s, 1H); MS (ESI, m/z) 425.1 [M+1]$^+$; ESI-HRMS calcd. m/z for C$_{23}$H$_{16}$N$_2$O$_3$F$_3$ 425.1113, found 425.1108 [M+1]$^+$.

4'-Carbamoyl-5-(5-(trifluoromethyl)-1H-benzo[d]imidazol-2-yl)-[1,1'-biphenyl]-3-carboxylic acid (32)

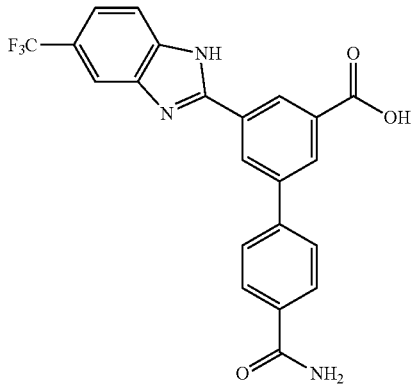

Chemical Formula: C$_{22}$H$_{14}$F$_3$N$_3$O$_3$
Exact Mass: 425.10
Molecular Weight: 425.37

Compound 75 (5 mg, 11.4 µmol) was converted to compound 32 (5 mg, 99%) as a white solid, using similar procedure used in the preparation of compound 30; HPLC purity 99% ($R_t$=10.64 min); $^1$H NMR (400 MHz, CD$_3$OD) δ 8.77 (s, 1H), 8.62 (s, 1H), 8.49 (s, 1H), 8.04 (d, J=7.48 Hz, 2H), 7.96 (s, 1H), 7.91 (d, J=7.52 Hz, 2H), 7.79 (d, J=7.92 Hz, 1H), 7.58 (d, J=8.48 Hz, 1H); MS (ESI, m/z) 426.1 [M+1]$^+$; ESI-HRMS calcd. m/z for C$_{22}$H$_{15}$N$_3$O$_3$F$_3$ 426.1066, found 426.1063 [M+1]$^+$.

5-(4-(1,2,3,6-Tetrahydropyridin-4-yl)phenyl)-3-(4-(4-(trifluoromethyl)phenyl)-1H-1,2,3-triazol-1-yl)-1H-pyrrole-2-carboxylic acid (33)

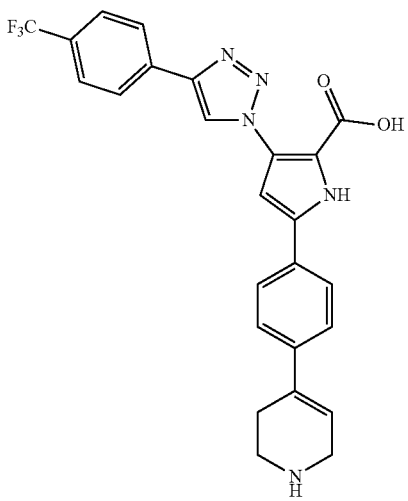

Chemical Formula: C$_{25}$H$_{20}$F$_3$N$_5$O$_2$
Exact Mass: 479.16
Molecular Weight: 479.46

Method A: Yield 30%; HPLC purity 99% ($R_t$=10.35 min); $^1$H NMR (400 MHz, CD$_3$OD) δ 9.23 (s, 1H), 8.13-8.05 (m, 2H), 7.80-7.68 (m, 3H), 7.58-49 (m, 2H), 7.37-7.31 (m, 1H), 7.01-6.92 (m, 1H), 6.22 (broad s, 1H), 3.83-3.76 (m, 2H), 3.48-3.37 (m, 2H), 2.84-2.74 (m, 2H); MS (ESI, m/z) 480.1 [M+1]$^+$; ESI-HRMS calcd. m/z for C$_{25}$H$_{21}$N$_5$O$_2$F$_3$ 480.1647, found 480.1649 [M+1]$^+$.

2-Methyl-4'-(piperidin-4-yl)-5-(1-(4-(trifluoromethyl)phenyl)-1H-1,2,3-triazol-4-yl)-[1,1'-biphenyl]-3-carboxylic acid (34)

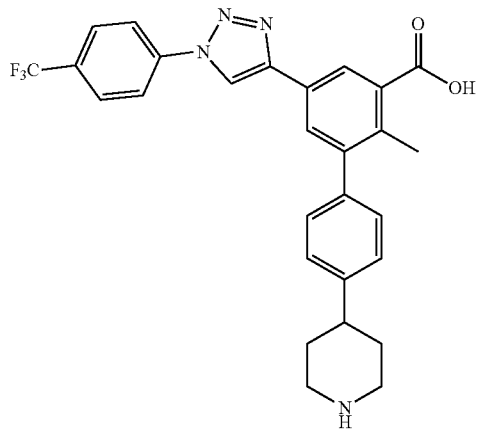

Chemical Formula: C$_{28}$H$_{25}$F$_3$N$_4$O$_2$
Exact Mass: 506.19
Molecular Weight: 506.53

Method A: Yield 72%; HPLC purity 99% ($R_t$=10.37 min); $^1$H NMR (400 MHz, DMSO-d$_6$) δ 8.31 (s, 1H), 8.22 (d, J=8.40 Hz, 2H), 8.04 (d, J=8.40 Hz, 2H), 7.88 (s, 1H), 7.39-7.34 (m, 3H), 7.01 (d, J=8.40 Hz, 1H), 6.72 (d, J=8.000 Hz, 1H), 3.42-3.35 (m, 2H), 3.05-2.91 (m, 3H), 2.38 (s, 3H), 2.01-1.83 (m, 4H); MS (ESI, m/z) 507.2 [M+1]$^+$; ESI-HRMS calcd. m/z for C$_{28}$H$_{26}$N$_4$O$_2$F$_3$ 507.2008 found 507.2009 [M+1]$^+$.

4-(4-(Piperidin-4-yl)phenyl)-2-(4-(trifluoromethyl)phenyl)-1H-benzo[d]imidazole-6-carboxylic acid (35)

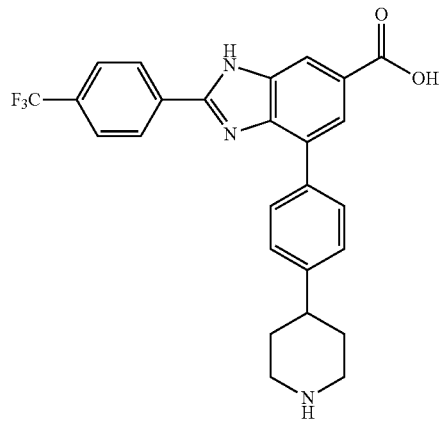

Chemical Formula: C$_{26}$H$_{22}$F$_3$N$_3$O$_2$
Exact Mass: 465.17
Molecular Weight: 465.48

Method B: Yield 63%; HPLC purity 99% ($R_t$=5.59 min); $^1$H NMR (400 MHz, CD$_3$OD) δ 8.37 (d, J=8.00 Hz, 2H), 8.28 (broad s, 1H), 8.12-8.02 (m, 3H), 7.89 (d, J=8.40 Hz, 2H), 7.53-7.45 (m, 2H), 3.58 (d, J=12.80 Hz, 2H), 3.25 (t, J=13.20 Hz, 2H), 3.08-3.00 (m, 1H), 2.23-2.15 (m, 2H), 2.06-1.95 (m, 2H); MS (ESI, m/z) 466.2 [M+1]$^+$; ESI-HRMS calcd. m/z for $C_{26}H_{23}N_3O_2F_3$ 466.1742 found 466.1747 [M+1]$^+$.

4-(4-(Piperidin-4-yl-3,4-t$_2$)phenyl)-7-(4-(trifluoromethyl)phenyl)-2-naphthoic acid (36)

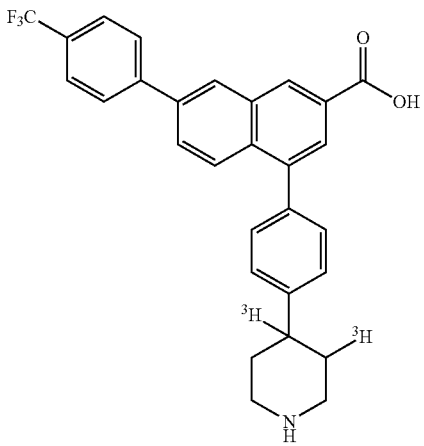

Chemical Formula: $C_{29}H_{22}T_2F_3NO_2$
Exact Mass: 479.19
Molecular Weight: 479.53

Method A:

tert-Butyl 4-(4-(3-(ethoxycarbonyl)-6-(4-(trifluoromethyl)phenyl)naphthalen-1-yl)phenyl)-3,6-dihydropyridine-1(2H)-carboxylate (38)

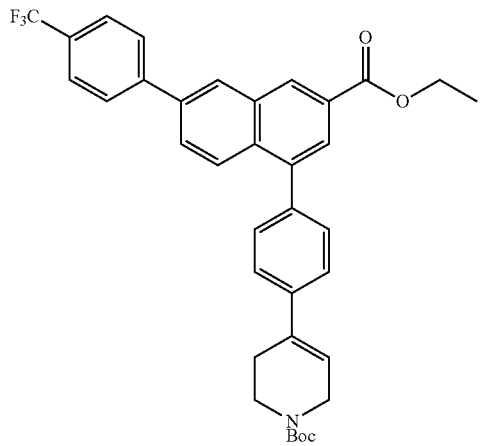

Chemical Formula: $C_{36}H_{34}F_3NO_4$
Exact Mass: 601.24
Molecular Weight: 601.67

A mixture of compound 37 (60 mg, 0.121 mmol; synthesized according to literature procedures reported), tert-butyl 4-(4-(4,4,5,5-tetramethyl-1,3,2-dioxaborolan-2-yl)phenyl)-3,6-dihydropyridine-1(2H)-carboxylate (47 mg, 0.121 mmol), PdCl$_2$(PPh$_3$)$_2$ (8 mg, 0.012 mmol) and Na$_2$CO$_3$ (47 mg, 0.240 mmol) in 1,4-dioxane:water (10:1, 5 mL) was purged with nitrogen gas for 15 min, and then stirred at 80° C. for 12 h under nitrogen atmosphere. After cooling at room temperature, the mixture was partitioned ethyl acetate (20 mL) and water (10 mL). The aqueous layer was extracted with ethyl acetate (10 mL×2), and then the combined organic layer was washed with brine (3 mL), dried (MgSO$_4$), filtered and evaporated under reduced pressure. The residue was purified by silica gel column chromatography (hexane:ethyl acetate=3:1) to afford compound 38 (35 mg, 48%) as a white solid; $^1$H NMR (400 MHz, CDCl$_3$) δ 8.68 (s, 1H), 8.23 (s, 1H), 8.06-8.03 (m, 2H), 7.83-7.74 (m, 5H), 7.55-7.49 (m, 4H), 6.17 (broad s, 1H), 4.46 (q, J=7.12 Hz, 2H), 4.14 (broad s, 2H), 3.71-3.68 (m, 2H), 2.63 (broad s, 2H), 1.51 (s, 9H), 1.45 (t, J=7.12 Hz, 3H); MS (ESI, m/z) 546.2 [M+1-tert-butyl]$^+$; ESI-HRMS calcd. m/z for $C_{32}H_{27}NO_4F_3$ 546.1892, found 546.1902 [M+1-tert-butyl]$^+$.

Ethyl 4-(4-(1,2,3,6-tetrahydropyridin-4-yl)phenyl)-7-(4-(trifluoromethyl)phenyl)-2-naphthoate (39)

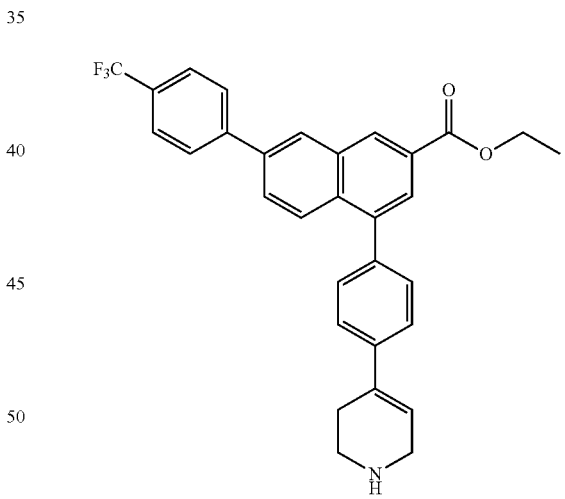

Chemical Formula: $C_{31}H_{26}F_3NO_2$
Exact Mass: 501.19
Molecular Weight: 501.55

Method B: Yield 90%; $^1$H NMR (400 MHz, CDCl$_3$) δ 8.69 (s, 1H), 8.24 (s, 1H), 8.05-8.00 (m, 2H), 7.83-7.74 (m, 5H), 7.58-7.52 (m, 4H), 6.16 (broad s, 1H), 4.46 (q, J=7.12 Hz, 2H), 3.95 (broad s, 2H), 3.56-3.48 (m, 2H), 2.93 (broad s, 2H), 1.45 (t, J=7.12 Hz, 3H); MS (ESI, m/z) 502.3 [M+1]$^+$; ESI-HRMS calcd. m/z for $C_{31}H_{27}NO_2F_3$ 502.1994, found 502.1996 [M+1]$^+$.

Ethyl 4-(4-(1-methylpiperidin-4-yl)phenyl)-7-(4-(trifluoromethyl)phenyl)-2-naphthoate (43a)

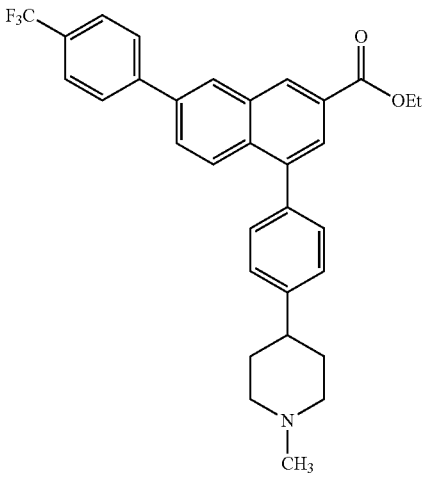

Chemical Formula: $C_{32}H_{30}F_3NO_2$
Exact Mass: 517.22
Molecular Weight: 517.59

Molecular Weight: 517.59

To a solution of compounds 42 (10 mg, 16.2 μmol; synthesized according to literature procedures reported) in acetonitrile (1 mL) were added potassium carbonate (6.7 mg, 48.6 μmol) and iodomethane (36 μL, 17.8 μmol, 0.5 M solution in acetonitrile), and then this reaction mixture was stirred at room temperature for 15 h. The reaction mixture was evaporated under reduced pressure. The residue was purified by silica gel column chromatography (dichloromethane:methanol=10:1) to afford compound 43a (5 mg, 55%) as a white solid; $^1$H NMR (400 MHz, CD$_3$OD) δ 8.74 (s, 1H), 8.44 (s, 1H), 8.04-7.93 (m, 5H), 7.82 (d, J=7.96 Hz, 2H), 7.52-7.47 (m, 4H), 4.50-4.45 (dd, J=7.03 Hz, 2H), 3.28 (m, 2H), 2.86-2.80 (m, 1H), 2.64-2.60 (m, 5H), 2.08 (d, J=12.00 Hz, 2H), 2.03-1.94 (m, 2H), 1.47 (t, J=7.00 Hz, 3H); MS (ESI, m/z) 518.2 [M+1]$^+$; ESI-HRMS calcd. m/z for $C_{32}H_{31}NO_2F_3$ 518.2307, found 518.2297 [M+1]$^+$.

Ethyl 4-(4-(1-(prop-2-yn-1-yl)piperidin-4-yl)phenyl)-7-(4-(trifluoromethyl)phenyl)-2-naphthoate (43b)

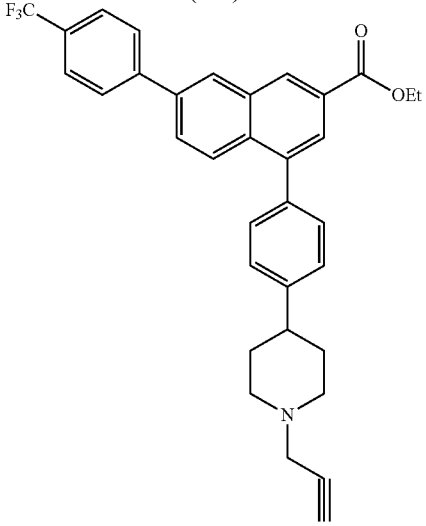

Chemical Formula: $C_{34}H_{30}F_3NO_2$
Exact Mass: 541.22
Molecular Weight: 541.61

To a solution of compounds 42 (24 mg, 0.04 mmol), which was synthesized according to literature procedures reported, in acetonitrile (2 mL) was added potassium carbonate (17.0 mg, 0.12 mmol), and then propargyl bromide (4 μL, 0.047 mmol, 1 M solution in acetonitrile) was added to the reaction mixture by dropwise addition under N$_2$ atmosphere. This reaction mixture was stirred at 50° C. temperature for 15 h. This mixture was partitioned ethyl acetate (5 mL) and water (10 mL). The aqueous layer was extracted with ethyl acetate (5 mL×2), and then the combined organic layer was washed with brine (3 mL), dried (MgSO$_4$), filtered and evaporated under reduced pressure. The residue was purified by silica gel column chromatography (hexane:ethyl acetate=3:1) to afford compound 43b (14 mg, 65%) as a white solid; $^1$H NMR (400 MHz, CDCl$_3$) δ 8.67 (s, 1H), 8.22 (s, 1H), 8.08-8.04 (m, 2H), 7.82 (d, J=8.24 Hz, 2H), 7.79-7.73 (m, 3H), 7.48 (d, J=8.04 Hz, 2H), 7.40 (d, J=8.04 Hz, 2H), 4.45 (q, J=7.12 Hz, 2H), 3.42 (broad s, 2H), 3.11-3.07 (m, 2H), 2.64-2.60 (m, 1H), 2.48-2.38 (m, 1H), 2.05-1.92 (m, 4H), 1.64-1.54 (m, 2H), 1.44 (t, J=7.12 Hz, 3H); MS (ESI, m/z) 542.2 [M+1]$^+$; ESI-HRMS calcd. m/z for $C_{34}H_{31}NO_2F_3$ 542.2307, found 542.2305 [M+1]$^+$.

Ethyl 4-(4-(1-propylpiperidin-4-yl)phenyl)-7-(4-(trifluoromethyl)phenyl)-2-naphthoate (43c)

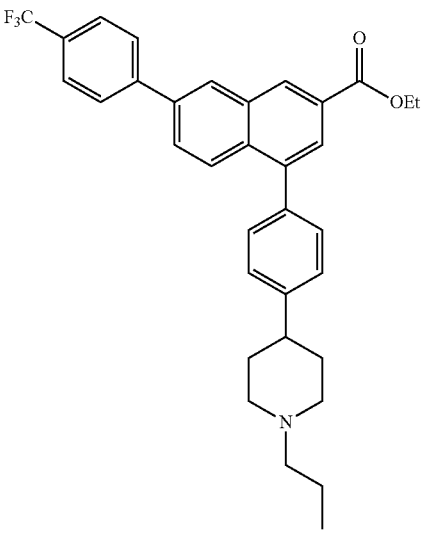

Chemical Formula: $C_{34}H_{34}F_3NO_2$
Exact Mass: 545.25
Molecular Weight: 545.65

To a solution of compounds 42 (5 mg, 8.10 μmol), which was synthesized according to literature procedures reported, in acetonitrile (1 mL) were added potassium carbonate (6.7 mg, 48.6 μmol) and 1-iodopropane (9 μL, 8.91 μmol, 1 M solution in acetonitrile), and then this reaction mixture was stirred at room temperature for 15 h. The reaction mixture was evaporated under reduced pressure. The residue was purified by silica gel column chromatography (dichloromethane:methanol=20:1) to afford compound 43c (3 mg, 68%) as a white solid; $^1$H NMR (400 MHz, CDCl$_3$) δ 8.70 (s, 1H), 8.25 (s, 1H), 8.06-8.04 (m, 2H), 7.86-7.77 (m, 5H), 7.51 (d, J=8.08 Hz, 2H), 7.45 (d, J=8.08 Hz, 2H), 4.48 (q, J=7.12 Hz, 2H), 3.59 (d, J=6.52 Hz, 2H), 2.91-2.85 (m, 2H), 2.71-2.60 (m, 3H), 2.13 (d, J=12.88 Hz, 2H), 1.97-1.92 (m, 2H), 1.47 (t, J=7.12 Hz, 3H), 1.05 (t, J=7.32 Hz, 3H); MS (ESI, m/z) 546.2 [M+1]$^+$; ESI-HRMS calcd. m/z for $C_{34}H_{35}NO_2F_3$ 546.2620, found 546.2627 [M+1]$^+$.

Ethyl 4-(4-(1-(hex-5-yn-1-yl)piperidin-4-yl)phenyl)-7-(4-(trifluoromethyl)phenyl)-2-naphthoate (43d)

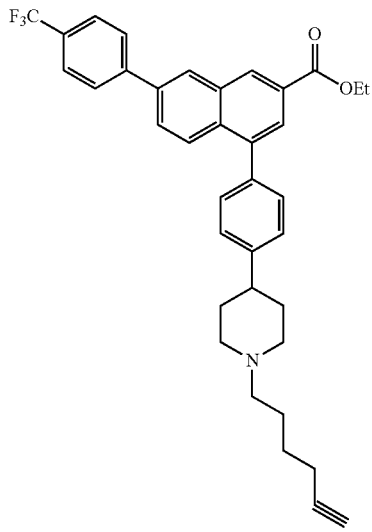

Chemical Formula: $C_{37}H_{36}F_3NO_2$
Exact Mass: 583.27
Molecular Weight: 583.70

To a solution of compounds 42 (50 mg, 0.081 mmol), which was synthesized according to literature procedures reported, in N,N-dimethylformamide (3 mL) were added potassium carbonate (34 mg, 0.024 mmol) and 6-bromohex-1-yne (65 mg, 0.405 mmol, 1 M solution in N,N-dimethylformamide), and then this reaction mixture was stirred at room temperature for 15 h. This mixture was partitioned ethyl acetate (5 mL) and water (10 mL). The aqueous layer was extracted with ethyl acetate (5 mL×2), and then the combined organic layer was washed with brine (3 mL), dried (MgSO$_4$), filtered and evaporated under reduced pressure. The residue was purified by silica gel column chromatography (hexane:ethyl acetate=3:1) to afford compound 43d (50 mg, 95%) as a white solid.

Ethyl 4-(4-(1-(2,2-dimethyl-4-oxo-3,8,11,14,17,20,23-heptaoxa-5-azahexacosan-26-oyl)piperidin-4-yl)phenyl)-7-(4-(trifluoromethyl)phenyl)-2-naphthoate (44a)

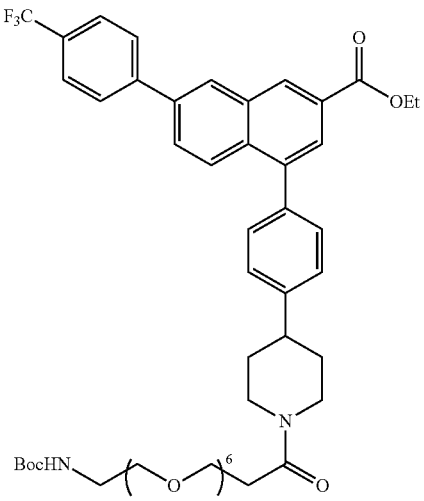

To a solution of compounds 42 (5 mg, 8.10 μmol) in N,N-dimethylformamide (0.5 mL) were added Boc-NH-PEG$_6$-CH$_2$—CH$_2$—COOH (7 mg, 15.4 μmol), HATU (3.4 mg, 0.081 μmol) and N,N-diisopropylethylamine (4 μL, 24.3 μmol), and then this reaction mixture was stirred at room temperature for 1 h. The reaction mixture was partitioned ethyl acetate (5 mL) and water (5 mL), and the aqueous layer was extracted with ethyl acetate (5 mL×2). The combined organic layer was washed brine (3 mL), dried over MgSO$_4$, filtered and evaporated under reduced pressure. The residue was purified by silica gel column chromatography (dichloromethane:methanol=50:1) to afford compound 44a (7 mg, 94%) as a white solid; $^1$H NMR (400 MHz, CDCl$_3$) δ 8.70 (s, 1H), 8.25 (s, 1H), 8.08-8.06 (m, 2H), 7.84 (d, J=8.16 Hz, 2H), 7.82-7.77 (m, 3H), 7.50 (d, J=7.92 Hz, 2H), 7.38 (d, J=8.00 Hz, 2H), 5.09 (s, 1H), 4.86 (d, J=13.24 Hz, 1H), 4.48 (q, J=7.12 Hz, 2H), 4.09 (d, J=13.32 Hz, 1H), 3.86 (t, J=6.58 Hz, 2H), 3.71-3.65 (m, 20H), 3.56 (t, J=5.08 Hz, 2H), 3.33 (d, J=4.88 Hz, 2H), 3.25-3.19 (m, 1H), 2.92-2.86 (m, 1H), 2.76 (t, J=6.68 Hz, 2H), 2.07-2.00 (m, 2H), 1.80-1.70 (m, 2H), 1.49-1.46 (m, 12H); MS (ESI, m/z) 939.5 [M+1]$^+$, 956.4 [M+NH$_4$]$^+$; ESI-HRMS calcd. m/z for $C_{51}H_{66}N_2O_{11}F_3$ 939.4619, found 939.4625 [M+1]$^+$.

Ethyl 4-(4-(1-(2,5,8,11,14,17-hexaoxaicosan-20-oyl)piperidin-4-yl)phenyl)-7-(4-(trifluoromethyl)phenyl)-2-naphthoate (44b)

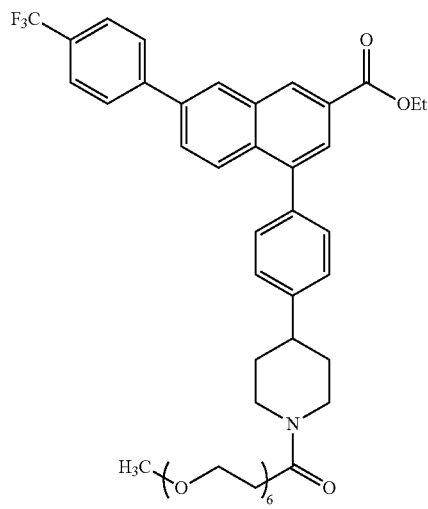

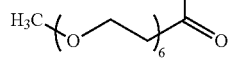

Compound 42 (11 mg, 14.9 μmol) with mPEG$_5$-CH$_2$—CH$_2$—COOH (7.4 mg, 22.8 μmol) were converted to compound 44b (11 mg, 93%) as a white foam, using similar procedure used in the preparation of compound 44a; $^1$H NMR (400 MHz, CDCl$_3$) δ 8.70 (s, 1H), 8.25 (s, 1H), 8.07 (d, J=7.88 Hz, 2H), 7.86-7.77 (m, 5H), 7.50 (d, J=7.88 Hz, 2H), 7.38 (d, J=7.88 Hz, 2H), 4.84 (d, J=13.8 Hz, 1H), 4.48 (q, J=7.10 Hz, 2H), 4.10 (d, J=13.6 Hz, 1H), 3.89-3.82 (m, 2H), 3.70-3.65 (m, 18H), 3.59-3.57 (m, 2H), 3.51 (s, 1H), 3.40 (s, 3H), 3.24 (t, J=12.8 Hz, 1H), 2.90 (t, J=12.1 Hz, 1H), 2.76 (t, J=12.7 Hz, 2H), 2.04 (t, J=13.5 Hz, 2H), 1.81-1.71 (m, 2H), 1.47 (t, J=7.15 Hz, 3H); MS (ESI, m/z) 810.4 [M+1]$^+$; ESI-HRMS calcd. m/z for $C_{45}H_{55}NO_9F_3$ 810.3829, found 810.3831 [M+1]$^+$.

Ethyl 4-(4-(quinuclidin-4-yl)phenyl)-7-(4-(trifluoromethyl)phenyl)-2-naphthoate (45)

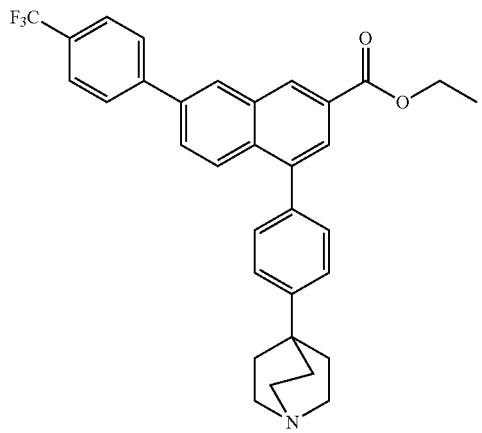

Chemical Formula: $C_{33}H_{30}F_3NO_2$
Exact Mass: 529.22
Molecular Weight: 529.60

The mixture of compound 40 (10 mg, 0.021 mmol), Pd(PPh$_3$)$_4$ (2 mg, 1.73 μmol) and potassium carbonate (8 mg, 0.057 mmol) in N,N-dimethylformamide (2 mL) was purged with nitrogen gas for 15 min, and then 4-(4-bromophenyl)quinuclidine (96, 7 mg, 0.025 mmol) was added to the mixture. The mixture was stirred at 80° C. for 3 h, and then allowed to be cooled at room temperature. This mixture was partitioned ethyl acetate (5 mL) and water (10 mL). The aqueous layer was extracted with ethyl acetate (5 mL×2), and then the combined organic layer was washed with brine (3 mL), dried (MgSO$_4$), filtered and evaporated under reduced pressure. The residue was purified by silica gel column chromatography (hexane:ethyl acetate=4:1) to afford compound 45 (10 mg, 88%) as a white solid; 1H NMR (400 MHz, CD$_3$OD) δ 8.75 (s, 1H), 8.44 (s, 1H), 8.01-7.92 (m, 5H), 7.82 (d, J=8.12 Hz, 2H), 7.62 (d, J=8.16 Hz, 2H), 7.57 (d, J=8.24 Hz, 2H), 4.49 (q, J=7.12 Hz, 2H), 3.58-3.54 (m, 6H), 2.37-2.33 (m, 6H), 1.47 (t, J=7.12 Hz, 3H); MS (ESI, m/z) 530.2 [M+1]$^+$; ESI-HRMS calcd. m/z for $C_{33}H_{31}NO_2F_3$ 530.2307, found 530.2302 [M+1]$^+$.

tert-Butyl 4-(3'-(methoxycarbonyl)-5'-(4-(4-(trifluoromethyl)phenyl)-1H-1,2,3-triazol-1-yl)-[1,1'-biphenyl]-4-yl)piperazine-1-carboxylate (48a)

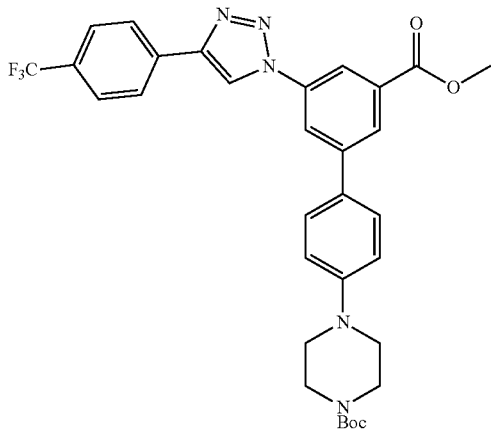

Chemical Formula: $C_{32}H_{32}F_3N_5O_4$
Exact Mass: 607.24
Molecular Weight: 607.63

The mixture of compound 47 (30 mg, 0.063 mmol), Pd(PPh$_3$)$_4$ (5.0 mg, 4.32 μmol) and potassium carbonate (25 mg, 0.180 mmol) in N,N-dimethylformamide (1.5 mL) was purged with nitrogen gas for 15 min, and then tert-Butyl 4-(4-bromophenyl)piperazine-1-carboxylate (26 mg, 0.076 mmol) was added to the mixture. The mixture was stirred at 80° C. for 3 h, and then allowed to be cooled at room temperature. This mixture was partitioned ethyl acetate (5 mL) and water (10 mL). The aqueous layer was extracted with ethyl acetate (5 mL×2), and then the combined organic layer washed with brine (3 mL), dried (MgSO$_4$), filtered and evaporated under reduced pressure. The residue was purified by silica gel column chromatography (hexane:ethyl acetate=4:1) to afford compound 48a (14 mg, 36%) as a colorless oil; 1H NMR (400 MHz, CDCl$_3$) δ 8.39 (s, 1H), 8.34 (s, 1H), 8.29 (s, 1H), 8.25 (s, 1H), 8.07 (d, J=7.96 Hz, 2H), 7.77 (d, J=7.96 Hz, 2H), 7.65 (d, J=8.60 Hz, 2H), 7.04 (d, J=8.60 Hz, 2H), 4.01 (s, 3H), 3.62 (broad s, 4H), 3.24 (broad s, 4H), 1.49 (s, 9H); MS (ESI, m/z) 608.3 [M+1]$^+$; ESI-HRMS calcd. m/z for $C_{32}H_{33}N_5O_4F_3$ 608.2485, found 608.2483 [M+1]$^+$.

tert-Butyl 6-(3'-(methoxycarbonyl)-5'-(4-(4-(trifluoromethyl)phenyl)-1H-1,2,3-triazol-1-yl)-[1,1'-biphenyl]-4-yl)-3-azabicyclo[4.1.0]heptane-3-carboxylate (48b)

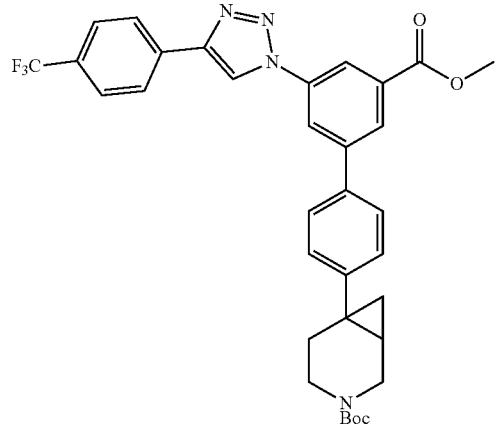

Chemical Formula: $C_{34}H_{33}F_3N_4O_4$
Exact Mass: 618.25
Molecular Weight: 618.66

Compound 47 (36 mg, 0.076 mmol) and compound 99 (32 mg, 0.091 mmol) were coupled to compound 48b (15 mg, 32%) as a white solid, using similar procedure used in the preparation of compound 48a; 1H NMR (400 MHz, CD$_3$OD) δ 9.18 (s, 1H), 8.40 (s, 1H), 8.31 (s, 1H), 8.26 (s, 1H), 8.11 (d, J=8.04 Hz, 2H), 7.77 (d, J=8.08 Hz, 2H), 7.65 (d, J=8.04 Hz, 2H), 7.39 (d, J=8.08 Hz, 2H), 3.97 (s, 3H), 3.78 (broad s, 2H), 3.41-3.36 (m, 2H), 2.20-2.11 (m, 2H), 1.48 (s, 9H), 1.29-1.24 (m, 1H), 1.08-1.04 (m, 1H), 0.89-0.86 (m, 1H); MS (ESI, m/z) 619.2 [M+1]$^+$; ESI-HRMS calcd. m/z for $C_{34}H_{34}N_4O_4F_3$ 619.2532, found 619.2524 [M+1]$^+$.

87 tert-Butyl 7,7-difluoro-6-(3'-(methoxycarbonyl)-5'-(4-(4-(trifluoromethyl)phenyl)-1H-1,2,3-triazol-1-yl)-[1,1'-biphenyl]-4-yl)-3-azabicyclo[4.1.0]heptane-3-carboxylate (48c)

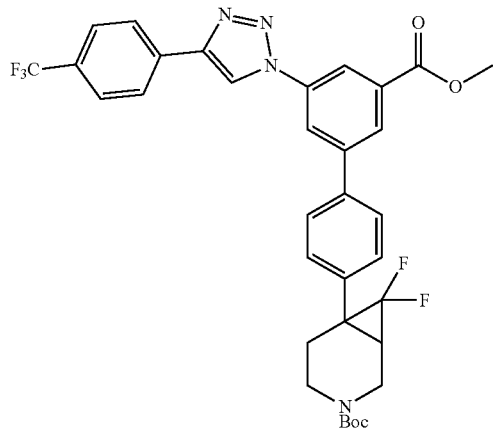

Chemical Formula: C$_{34}$H$_{31}$F$_5$N$_4$O$_4$
Exact Mass: 654.23
Molecular Weight: 654.64

Compound 47 (mg, mmol) and compound 101 (mg, mmol) were coupled to compound 48c (mg, %) as a white solid, using similar procedure used in the preparation of compound 48a.

tert-Butyl 5-(3'-(methoxycarbonyl)-5'-(4-(4-(trifluoromethyl)phenyl)-1H-1,2,3-triazol-1-yl)-[1,1'-biphenyl]-4-yl)-2-azabicyclo[3.1.1]heptane-2-carboxylate (48d)

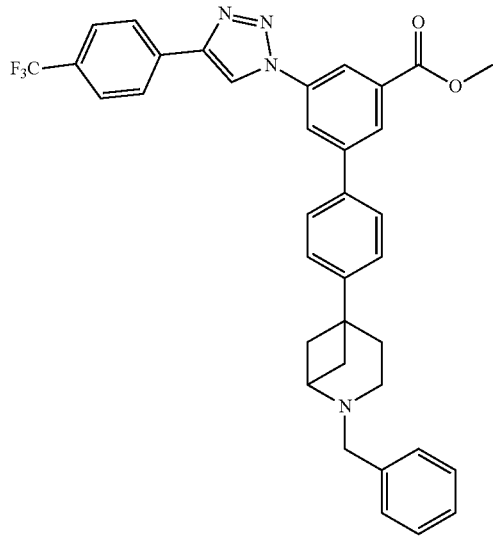

Chemical Formula: C$_{36}$H$_{31}$F$_3$N$_4$O$_2$
Exact Mass: 608.24
Molecular Weight: 608.67

88

Compound 47 (mg, mmol) and compound 111 (mg, mmol) were coupled to compound 48d (mg, %) as a white solid, using similar procedure used in the preparation of compound 48a.

tert-Butyl 5-(3'-(methoxycarbonyl)-5'-(4-(4-(trifluoromethyl)phenyl)-1H-1,2,3-triazol-1-yl)-[1,1'-biphenyl]-4-yl)-2-azabicyclo[2.2.2]octane-2-carboxylate (48e)

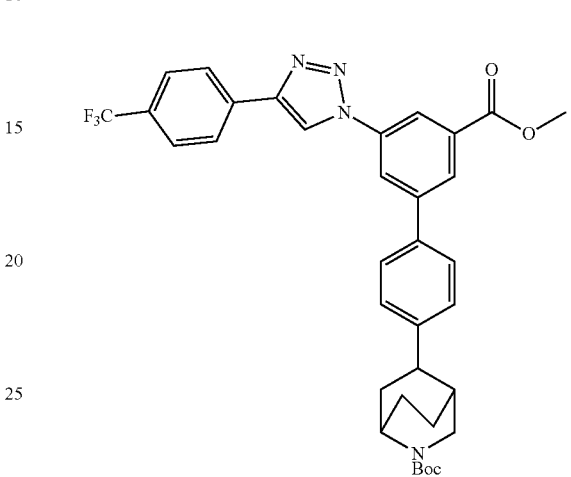

Chemical Formula: C$_{35}$H$_{35}$F$_3$N$_4$O$_4$
Exact Mass: 632.26
Molecular Weight: 632.68

Compound 47 (mg, mmol) and compound 104 (mg, mmol) were coupled to compound 48e (mg, %) as a white solid, using similar procedure used in the preparation of compound 48a.

Methyl 4'-(piperazin-1-yl)-5-(4-(4-(trifluoromethyl)phenyl)-1H-1,2,3-triazol-1-yl)-[1,1'-biphenyl]-3-carboxylate (49a)

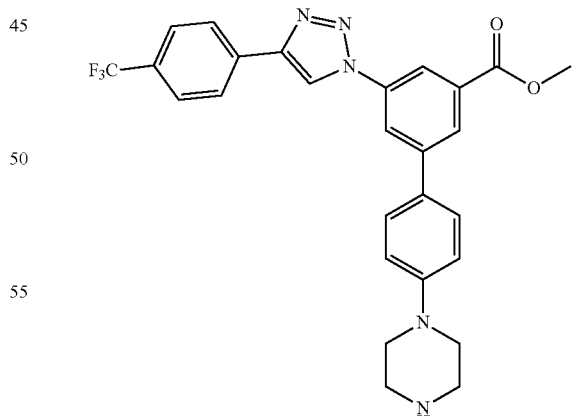

Chemical Formula: C$_{27}$H$_{24}$F$_3$N$_5$O$_2$
Exact Mass: 507.19
Molecular Weight: 507.52

Method B: Yield 76%; $^1$H NMR (400 MHz, CD$_3$OD) δ 9.26 (s, 1H), 8.46 (s, 1H), 8.40 (s, 1H), 8.35 (s, 1H), 8.16 (d, J=8.12 Hz, 2H), 7.81-7.75 (m, 4H), 7.20 (d, J=8.60 Hz, 2H), 4.01 (s, 3H), 3.54 (broad s, 4H), 3.42 (broad s, 4H); MS (ESI, m/z) 508.2 [M+1]⁺; ESI-HRMS calcd. m/z for $C_{27}H_{25}N_5O_2F_3$ 508.1960, found 508.1964 [M+1]⁺.

4'-(3-(tert-Butoxycarbonyl)-3-azabicyclo[4.1.0]heptan-6-yl)-5-(4-(4-(trifluoromethyl)phenyl)-1H-1,2,3-triazol-1-yl)-[1,1'-biphenyl]-3-carboxylic acid (49b)

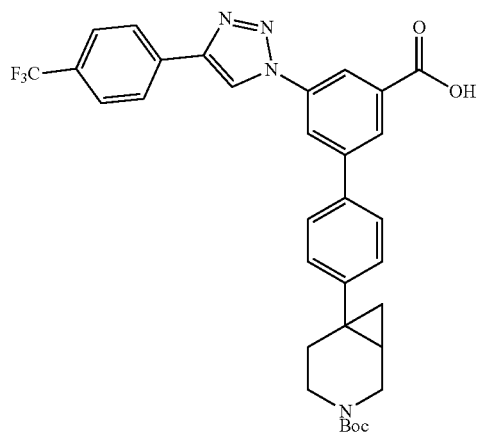

Chemical Formula: $C_{33}H_{31}F_3N_4O_4$
Exact Mass: 604.23
Molecular Weight: 604.63

Method A: Yield 76%; ¹H NMR (400 MHz, CD₃OD) δ 9.24 (s, 1H), 8.49 (s, 1H), 8.38 (d, J=6.6 Hz, 2H), 8.16 (d, J=8.04 Hz, 2H), 7.79 (d, J=8.12 Hz, 2H), 7.72 (d, J=8.04 Hz, 2H), 7.45 (d, J=7.96 Hz, 2H), 3.79 (broad s, 2H), 3.41-3.36 (m, 2H), 2.21-2.11 (m, 2H), 1.48 (s, 9H), 1.25 (d, J=6.40 Hz, 1H), 1.11-1.06 (m, 1H), 0.91-0.86 (m, 1H); MS (ESI, m/z) 549.2 [M+1-tert-butyl]⁺.

4'-(3-(tert-Butoxycarbonyl)-7,7-difluoro-3-azabicyclo[4.1.0]heptan-6-yl)-5-(4-(4-(trifluoromethyl)phenyl)-1H-1,2,3-triazol-1-yl)-[1,1'-biphenyl]-3-carboxylic acid (49c)

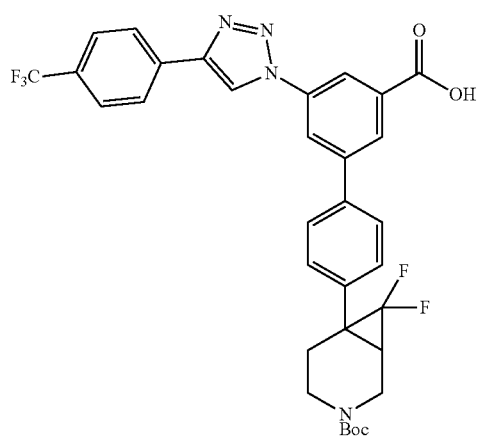

Chemical Formula: $C_{33}H_{29}F_5N_4O_4$
Exact Mass: 640.21
Molecular Weight: 640.61

Method A:

4'-(2-Benzyl-2-azabicyclo[3.1.1]heptan-5-yl)-5-(4-(4-(trifluoromethyl)phenyl)-1H-1,2,3-triazol-1-yl)-[1,1'-biphenyl]-3-carboxylic acid (49d)

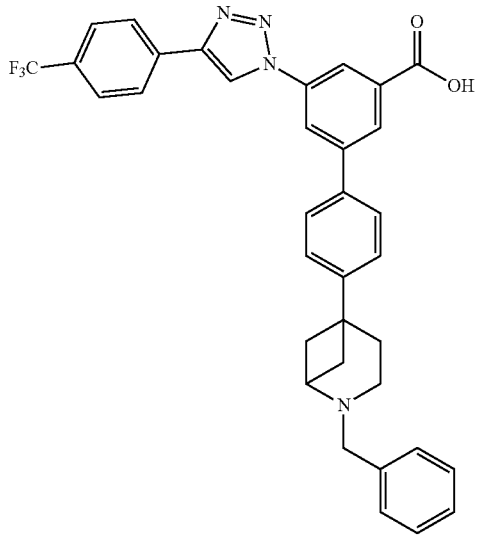

Chemical Formula: $C_{35}H_{29}F_3N_4O_2$
Exact Mass: 594.22
Molecular Weight: 594.64

Method A:

4'-(2-(tert-Butoxycarbonyl)-2-azabicyclo[2.2.2]octan-5-yl)-5-(4-(4-(trifluoromethyl)phenyl)-1H-1,2,3-triazol-1-yl)-[1,1'-biphenyl]-3-carboxylic acid (49e)

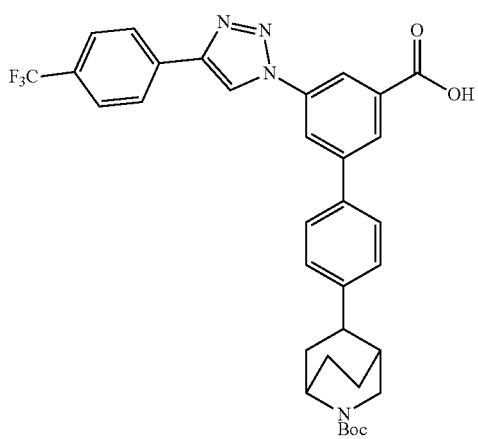

Chemical Formula: $C_{34}H_{33}F_3N_4O_4$
Exact Mass: 618.25
Molecular Weight: 618.66

Method A:

tert-Butyl 4-(3'-carbamoyl-5'-(4-(4-(trifluoromethyl)phenyl)-1H-1,2,3-triazol-1-yl)-[1,1'-biphenyl]-4-yl)piperidine-1-carboxylate (51)

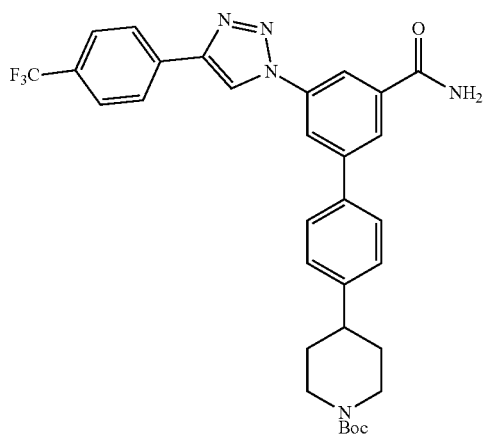

Chemical Formula: $C_{32}H_{32}F_3N_5O_3$
Exact Mass: 591.25
Molecular Weight: 591.64

To a solution of compound 50 (47 mg, 0.079 mmol; synthesized according to literature procedures reported) in dimethylformamide (3 mL) were added NH$_4$Cl (8.5 mg, 0.159 mmol), HATU (45 mg, 0.119 mmol) and N,N-diisopropylethylamine (20 mg, 28 μl, 0.159 mmol), and then this reaction mixture was stirred at room temperature for 1 h. This mixture was partitioned ethyl acetate (6 mL) and water (3 mL). The aqueous layer was extracted with ethyl acetate (5 mL×2), and then the combined organic layer was washed with brine (3 mL), dried (MgSO$_4$), filtered and evaporated under reduced pressure. The residue was purified by silica gel column chromatography (hexane:ethyl acetate=1:1) to afford compound 51 (48 mg, 99%) as a white solid; $^1$H NMR (400 MHz, CDCl$_3$) δ 8.44 (s, 1H), 8.27 (s, 1H), 8.23 (s, 1H), 8.11 (s, 1H), 8.07 (d, J=8.04 Hz, 2H), 7.76 (d, J=8.16 Hz, 2H), 7.66 (d, J=8.24 Hz, 2H), 7.38 (d, J=8.20 Hz, 2H), 4.31 (d, J=13.68 Hz, 2H), 2.89-2.81 (m, 2H), 2.80-2.73 (m, 1H), 1.89 (d, J=12.00 Hz, 2H), 1.67 (merged with water peak), 1.51 (s, 9H); MS (ESI, M/Z) 536.1 [M+1-tert-butyl]$^+$, 592.2 [M+1]$^+$; ESI-HRMS calcd. m/z for $C_{28}H_{25}N_5O_3F_3$ 536.1909, found 536.1911 [M+1-tert-butyl]$^+$.

tert-Butyl 4-(3'-cyano-5'-(4-(4-(trifluoromethyl)phenyl)-1H-1,2,3-triazol-1-yl)-[1,1'-biphenyl]-4-yl)piperidine-1-carboxylate (52)

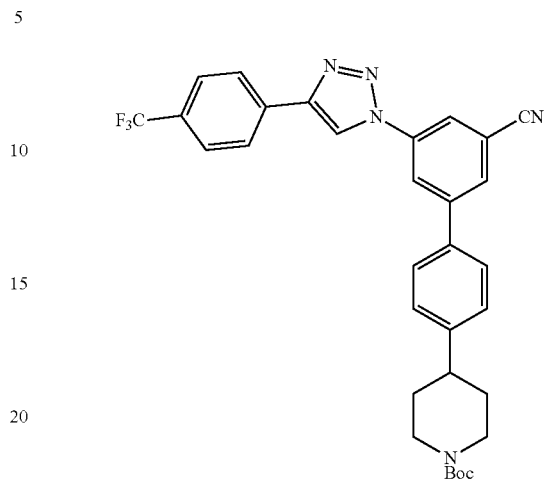

Chemical Formula: $C_{32}H_{30}F_3N_5O_2$
Exact Mass: 573.24
Molecular Weight: 573.62

To a solution of compound 51 (41 mg, 0.069 mmol) in dichloromethane (2 mL) were added trifluoroacetic anhydride (97 mg, 64 μl, 0.462 mmol) and triethylamine (50 mg, 69 μl, 0.494 mmol) at 0° C., and then this reaction mixture was stirred at room temperature for 1 h. This mixture was partitioned dichloromethane (6 mL) and water (3 mL). The aqueous layer was extracted with dichloromethane (5 mL×2), and the organic layer was washed with brine (3 mL), dried (MgSO$_4$), filtered and evaporated under reduced pressure. The residue was purified by silica gel column chromatography (hexane:ethyl acetate=4:1) to afford compound 52 (30 mg, 76%) as a white solid; $^1$H NMR (400 MHz, CDCl$_3$) δ 8.38 (s, 1H), 8.31 (t, J=1.84 Hz, 1H), 8.07 (d, J=8.08 Hz, 2H), 8.06-8.04 (m, 1H), 7.96 (t, J=1.42 Hz, 1H), 7.77 (d, J=8.20 Hz, 2H), 7.62 (d, J=8.28 Hz, 2H), 7.39 (d, J=8.20 Hz, 2H), 4.31 (d, J=12.84 Hz, 2H), 2.89-2.83 (m, 2H), 2.79-2.72 (m, 1H), 1.89 (d, J=12.04 Hz, 2H), 1.75-1.65 (m, 2H), 1.52 (s, 9H); MS (ESI, M/Z) 518.1 [M+1-tert-butyl]$^+$; ESI-HRMS calcd. m/z for $C_{28}H_{23}N_5O_2F_3$ 518.1804, found 518.1801 [M+1-tert-butyl]$^+$.

Methyl 3-bromo-5-iodobenzoate (54)

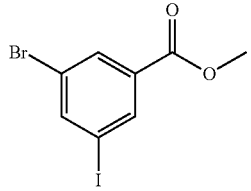

Chemical Formula: $C_8H_6BrIO_2$
Exact Mass: 339.86
Molecular Weight: 340.94

To a solution of 3-bromo-5-iodobenzoic acid (53, 500 mg, 1.53 mmol) in methanol (7.5 mL) was added dropwise thionyl chloride (1.1 mL, 2.18 g, 18.35 mmol) at 0° C., and then this reaction mixture was stirred at room temperature for 15 h. After being neutralized with saturated NaHCO$_3$ solution on the ice bath, the mixture was extracted with ethyl acetate (20 mL×2). The combined organic layer was washed with brine, dried over MgSO$_4$, filtered and evaporated under reduced pressure to afford compound 54 (498 mg, 96%) as a white solid; $^1$H NMR (400 MHz, CDCl$_3$) δ 8.32 (t, J=1.40 Hz, 1H), 8.15 (t, J=1.58 Hz, 1H), 8.06 (t, J=1.64 Hz, 1H), 3.95 (s, 3H); MS (ESI, m/z) 340.9, 342.9 [M+1]$^+$; ESI-HRMS calcd. m/z for C$_8$H$_7$O$_2$I$^{79}$Br 340.8674, found 340.8672 [M+1]$^+$.

Methyl 3-bromo-5-((trimethylsilyl)ethynyl)benzoate (55)

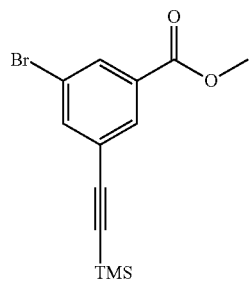

Chemical Formula:
C$_{13}$H$_{15}$BrO$_2$Si
Exact Mass: 310.00
Molecular Weight: 311.25

To a solution of compound 54 (100 mg, 0.293 mmol) in N,N-dimethylformamide (2 mL) were added PdCl$_2$(PPh$_3$)$_2$ (41 mg, 0.058 mmol), copper iodide (5 mg, 0.029 mmol), triethylamine (0.122 mL, 178 mg, 1.76 mmol), TMS-acetylene (0.045 mL, 0.322 mmol), and then this reaction mixture was stirred at room temperature for 5 h. After the solvent was evaporated under reduced pressure, the residue was purified by silica gel column chromatography (hexane:ethyl acetate=50:1) to afford compound 55 (84 mg, 92%) as a colorless syrup; $^1$H NMR (400 MHz, CDCl$_3$) δ 8.12 (t, J=1.70 Hz, 1H), 8.06 (t, J=1.44 Hz, 1H), 7.79 (t, J=1.68 Hz, 1H), 3.94 (s, 3H), 0.27 (s, 9H); MS (ESI, m/z) 311.0, 313.0 [M+1]$^+$; ESI-HRMS calcd. m/z for C$_3$H$_6$O$_2$$^{79}$BrSi 311.0103, found 311.0104 [M+1]$^+$.

Methyl 3-bromo-5-ethynylbenzoate (56)

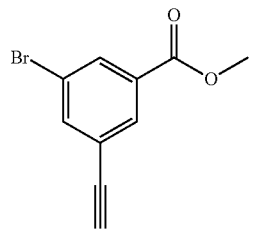

Chemical Formula:
C$_{10}$H$_7$BrO$_2$
Exact Mass: 237.96
Molecular Weight: 239.07

To a solution of compound 55 (76 mg, 0.244 mmol) in tetrahydrofuran (2 mL) was added tetrabutylammonium fluoride (0.02 mL, 1 M solution in tetrahydrofuran), and then this reaction mixture was stirred at room temperature for 0.5 h. After being neutralized with acetic acid, the mixture was evaporated under reduced pressure. The residue was purified by silica gel column chromatography (hexane:ethyl acetate=30:1) to afford compound 56 (55 mg, 94%) as a white solid; $^1$H NMR (400 MHz, CDCl$_3$) δ 8.16 (t, J=1.70 Hz, 1H), 8.10 (t, J=1.44 Hz, 1H), 7.82 (t, J=1.68 Hz, 1H), 3.95 (s, 3H), 3.19 (s, 1H); MS (ESI, m/z) 239.0, 241.0 [M+1]$^+$; ESI-HRMS calcd. m/z for C$_{10}$H$_8$O$_2$$^{79}$Br 238.9708, found 238.9709 [M+1]$^+$.

Methyl 3-bromo-5-(1-(4-(trifluoromethyl)phenyl)-1H-1,2,3-triazol-4-yl)benzoate (57)

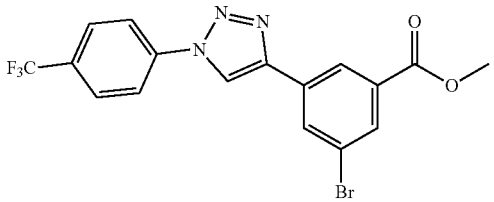

Chemical Formula: C$_{17}$H$_{11}$BrF$_3$N$_3$O$_2$
Exact Mass: 425.00
Molecular Weight: 426.19

To a solution of compound 56 (49 mg, 0.205 mmol) and 1-azido-4-(trifluoromethyl)benzene (60 µL, 0.307 mmol; synthesized according to literature procedures reported) in tetrahydrofuran:water (2 mL, 1:1) were added CuSO$_4$.5H$_2$O (25 mg, 0.102 mmol) and sodium ascorbate (61 mg, 0.307 mmol, freshly prepared 1 M aqueous solution), and then this reaction mixture was stirred at room temperature for 1 h. The reaction mixture was partitioned diethyl ether (10 mL) and water (5 mL), and the aqueous layer was extracted with diethyl ether (10 mL×2). The combined organic layer was washed brine (5 mL), dried over MgSO$_4$, filtered and evaporated under reduced pressure. The residue was purified by silica gel column chromatography (hexane:ethyl acetate=9:1) to afford compound 57 (40 mg, 46%) as a white solid; $^1$H NMR (400 MHz, CDCl$_3$) δ 8.44 (t, J=1.48 Hz, 1H), 8.38 (s, 1H), 8.36 (t, J=1.74 Hz, 1H), 8.18 (t, J=1.64 Hz, 1H), 7.98 (d, J=8.44 Hz, 2H), 7.86 (d, J=8.56 Hz, 2H), 3.98 (s, 3H); MS (ESI, m/z) 426.0, 428.0 [M+1]$^+$; ESI-HRMS calcd. m/z for C$_{17}$H$_{12}$N$_3$O$_2$F$_3$$^{79}$Br 426.0065, found 426.0063 [M+1]$^+$.

Methyl 3-(4,4,5,5-tetramethyl-1,3,2-dioxaborolan-2-yl)-5-(1-(4-(trifluoromethyl)phenyl)-1H-1,2,3-triazol-4-yl)benzoate (58)

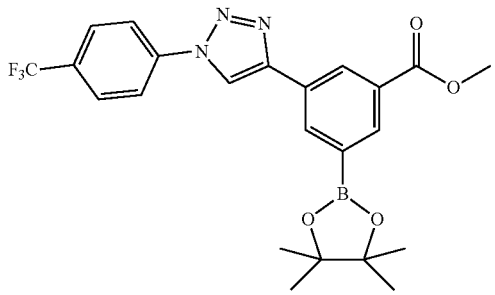

Chemical Formula: $C_{23}H_{23}BrF_3N_3O_4$
Exact Mass: 473.17
Molecular Weight: 473.26

To a solution of compound 57 (305 mg, 0.716 mmol) in 1,4-dioxane (10 mL) were added bis(pinacolato)diboron (363 mg, 1.43 mmol), $PdCl_2(dppf)$ (12 mg, 14.3 μmol) and potassium acetate (210 mg, 2.15 mmol), and then this reaction mixture was stirred at 70° C. for 15 h. The reaction mixture was partitioned ethyl acetate (20 mL) and water (10 mL), and the aqueous layer was extracted with ethyl acetate (10 mL×2). The combined organic layer was washed brine (5 mL), dried over $MgSO_4$, filtered and evaporated under reduced pressure. The residue was purified by silica gel column chromatography (hexane:ethyl acetate=2:1) to afford compound 58 (258 mg, 76%) as a white solid; $^1H$ NMR (400 MHz, $CDCl_3$) δ 8.72 (s, 1H), 8.54 (s, 1H), 8.50 (s, 1H), 8.41 (s, 1H), 8.00 (d, J=8.28 Hz, 2H), 7.86 (d, J=8.32 Hz, 2H), 3.99 (s, 3H), 1.41 (s, 12H); MS (ESI, m/z) 474.2 [M+1]$^+$; ESI-HRMS calcd. m/z for $C_{23}H_{24}N_3O_4F^{10}B$ 474.1812, found 474.1804 [M+1]$^+$.

Methyl 4'-carbamoyl-5-(1-(4-(trifluoromethyl)phenyl)-1H-1,2,3-triazol-4-yl)-[1,1'-biphenyl]-3-carboxylate (59a)

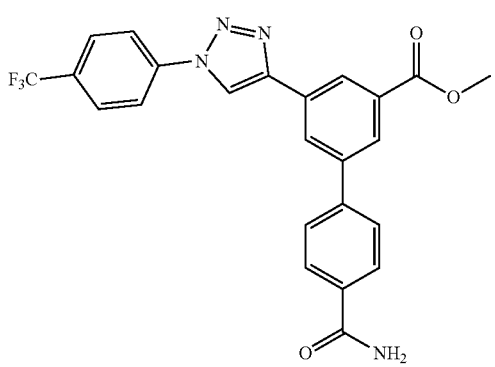

Chemical Formula: $C_{24}H_{17}F_3N_4O_3$
Exact Mass: 466.13
Molecular Weight: 466.42

A mixture of compound 58 (51 mg, 0.106 mmol), 4-bromobenzamide (26 mg, 0.127 mmol) and $PdCl_2(dppf)$ (9 mg, 10.6 μmol) in dimethoxyethane (2 mL) and 2 M $Na_2CO_3$ aqueous solution (0.2 mL) was stirred at 50° C. for 3 h. After cooling at room temperature, the mixture was partitioned diethyl ether (5 mL) and water (10 mL). The aqueous layer was extracted with diethyl ether (5 mL×2), and then the combined organic layer was washed with brine (3 mL), dried ($MgSO_4$), filtered and evaporated under reduced pressure. The residue was purified by silica gel column chromatography (hexane:ethyl acetate=1:1) to afford compound 59a (24 mg, 46%) as a white solid; $^1H$ NMR (400 MHz, $CDCl_3$) δ 8.53-8.52 (m, 2H), 8.45 (s, 1H), 8.34 (s, 1H), 8.02 (d, J=8.40 Hz, 2H), 7.97 (d, J=8.16 Hz, 2H), 7.88 (d, J=8.48 Hz, 2H), 7.83 (d, J=8.16 Hz, 2H), 4.03 (s, 3H); MS (ESI, m/z) 467.1 [M+1]$^+$; ESI-HRMS calcd. m/z for $C_{24}H_{18}N_4O_3F_3$ 467.1331, found 467.1325 [M+1]$^+$.

tert-Butyl 4-(3'-(methoxycarbonyl)-5'-(1-(4-(trifluoromethyl)phenyl)-1H-1,2,3-triazol-4-yl)-[1,1'-biphenyl]-4-yl)piperidine-1-carboxylate (59b)

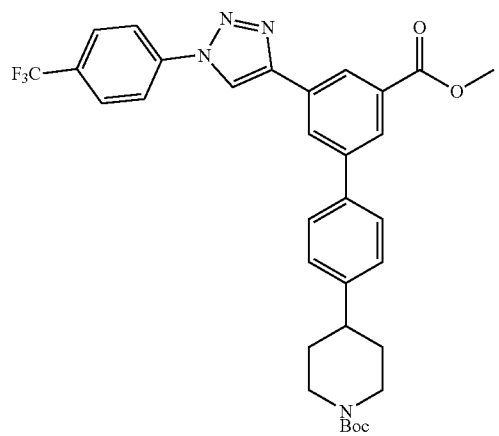

Chemical Formula: $C_{33}H_{33}F_3N_4O_4$
Exact Mass: 606.25
Molecular Weight: 606.65

The mixture of compound 58 (26 mg, 0.055 mmol), $Pd(PPh_3)_4$ (3.8 mg, 3.29 μmol) and potassium carbonate (23 mg, 0.165 mmol) in N,N-dimethylformamide (1.5 mL) was purged with nitrogen gas for 15 min, and then NBoc-(4-bromophenyl)piperidine (28 mg, 0.082 mmol) was added to the mixture. The mixture was stirred at 85° C. for 2 h, and then allowed to be cooled at room temperature. This mixture was partitioned diethyl ether (5 mL) and water (10 mL). The aqueous layer was extracted with diethyl ether (5 mL×2), and then the combined organic layer was washed with brine (3 mL), dried ($MgSO_4$), filtered and evaporated under reduced pressure. The residue was purified by silica gel column chromatography (hexane:ethyl acetate=4:1) to afford compound 59b (13 mg, 39%) as a white solid; $^1H$ NMR (400 MHz, $CD_3OD$) δ 9.26 (s, 1H), 8.57 (s, 1H), 8.45 (s, 1H), 8.27 (s, 1H), 8.20 (d, J=8.44 Hz, 2H), 7.95 (d, J=8.56 Hz, 2H), 7.71 (d, J=8.20 Hz, 2H), 7.41 (d, J=8.20 Hz, 2H), 4.26 (d, J=12.96 Hz, 2H), 2.93 (broad s, 2H), 2.86-2.79 (m, 1H), 1.90 (d, J=12.40 Hz, 2H), 1.72-1.61 (m, 2H), 1.51 (s, 9H); MS (ESI, m/z) 551.2 [M+1]$^+$; ESI-HRMS calcd. m/z for $C_{29}H_{26}N_4O_4F_3$ 551.1906, found 551.1902 [M+1]$^+$.

Methyl 3-(5-((3-((tert-butoxycarbonyl)amino)propyl)carbamoyl)thiophen-2-yl)-5-(1-(4-(trifluoromethyl) phenyl)-1H-1,2,3-triazol-4-yl)benzoate (59c)

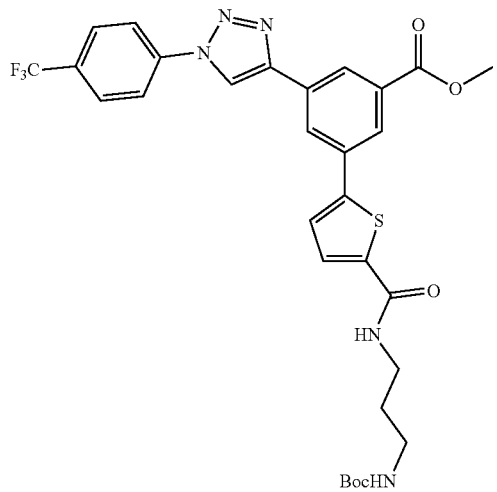

Chemical Formula: C$_{30}$H$_{30}$F$_3$N$_5$O$_5$S
Exact Mass: 629.19
Molecular Weight: 629.66

Compound 58 (45 mg, 0.095 mmol) and tert-butyl (3-(5-bromothiophene-2-carboxamido)propyl) carbamate (38 mg, 0.105 mmol) were converted to compound 59c (31 mg, 52%) as a white solid, using similar procedure used in the preparation of compound 59a; $^1$H NMR (400 MHz, CDCl$_3$) δ 8.47 (s, 1H), 8.45-8.44 (m, 2H), 8.31 (s, 1H), 8.02 (d, J=8.44 Hz, 2H), 7.87 (d, J=8.56 Hz, 2H), 7.61 (d, J=3.64 Hz, 1H), 7.47 (d, J=3.88 Hz, 1H), 7.36 (broad s, 1H), 4.92 (broad s, 1H), 4.01 (s, 3H), 3.53 (q, J=6.03 Hz, 2H), 3.30 (q, J=5.97 Hz, 2H), 1.79-1.73 (m, 2H), 1.50 (s, 9H); MS (ESI, m/z) 530.1 [M+1]$^+$; ESI-HRMS calcd. m/z for C$_{25}$H$_{23}$N$_5$O$_3$F$_3$$^{32}$S 530.1474, found 530.1476 [M+1]$^+$.

4'-(1-(tert-Butoxycarbonyl)piperidin-4-yl)-5-(1-(4-(trifluoromethyl)phenyl)-1H-1,2,3-triazol-4-yl)-[1,1'-biphenyl]-3-carboxylic acid (60b)

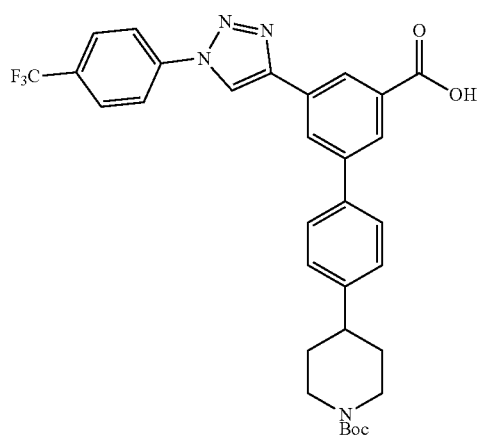

Chemical Formula: C$_{32}$H$_{31}$F$_3$N$_4$O$_4$
Exact Mass: 592.23
Molecular Weight: 592.62

Method A: Yield 60%; $^1$H NMR (400 MHz, CD$_3$OD) δ 9.20 (s, 1H), 8.53 (s, 1H), 8.39 (s, 1H), 8.25 (s, 1H), 8.18 (d, J=7.92 Hz, 2H), 7.93 (d, J=8.20 Hz, 2H), 7.68 (d, J=7.76 Hz, 2H), 7.37 (d, J=7.84 Hz, 2H), 4.25 (d, J=13.12 Hz, 2H), 2.91 (broad s, 2H), 2.80 (t, J=12.02 Hz, 1H), 1.88 (d, J=12.68 Hz, 2H), 1.70-1.60 (m, 2H), 1.51 (s, 9H).

3-(5-((3-((tert-Butoxycarbonyl)amino)propyl)carbamoyl)thiophen-2-yl)-5-(1-(4-(trifluoromethyl) phenyl)-1H-1,2,3-triazol-4-yl)benzoic acid (60c)

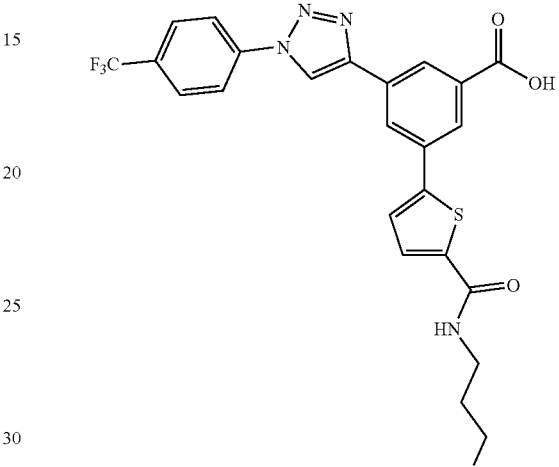

Chemical Formula: C$_{29}$H$_{28}$F$_3$N$_5$O$_5$S
Exact Mass: 615.18
Molecular Weight: 615.63

Method A: Yield 99%; $^1$H NMR (400 MHz, CD$_3$OD) δ 9.13 (s, 1H), 8.48 (s, 1H), 8.34 (s, 1H), 8.23 (s, 1H), 8.13 (s, 2H), 7.90 (s, 2H), 7.65 (s, 1H), 7.50 (s, 1H), 3.41 (s, 2H), 3.16 (s, 2H), 1.78 (s, 2H), 1.46 (s, 9H); MS (ESI, m/z) 516.1 [M+1-Boc]$^+$; ESI-HRMS calcd. m/z for C$_{24}$H$_{21}$N$_5$O$_3$F$_3$$^{32}$S 516.1317, found [M+1-Boc]$^+$.

Methyl 3-amino-5-bromobenzoate (61b)

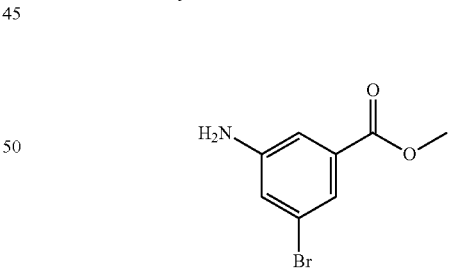

Chemical Formula: C$_8$H$_8$BrNO$_2$
Exact Mass: 228.97
Molecular Weight: 230.06

3-Bromo-5-aminobenzoic acid (61a, 1.01 g, 4.62 mmol) was stirred in methanol (15 mL) with ice cooling, and the yellow solution was treated with thionyl chloride (4.00 mL, 55.0 mmol) dropwise over 20 min. The resulting mixture was warm up to room temperature and left stirring for 15 h. The reaction mixture was quenched with aqueous saturated NaHCO$_3$ solution at 0° C. The solvent was then removed under vacuum, and the residue was suspended in ethyl acetate (200 mL). The organic phase was washed with brine (100 mL), dried (Na$_2$SO$_4$) and concentrated in vacuo to afford the title compound 61b (1.08 g, 98%) as a yellow solid; $^1$H NMR (400 MHz, DMSO-d$_6$) δ 7.16 (dd, J=1.48, 2.12 Hz, 1H), 7.13 (t, J=1.64 Hz, 1H), 6.96 (t, J=2.00 Hz, 1H), 5.74 (s, 2H), 3.81 (s, 3H); MS (ESI, m/z) 231 [M+1]$^+$; ESI-HRMS calcd. m/z for C$_8$H$_8$BrNO$_2$ 229.9817, found 229.9818 [M+1]$^+$.

Methyl 3-amino-5-(4,4,5,5-tetramethyl-1,3,2-dioxaborolan-2-yl)benzoate (62)

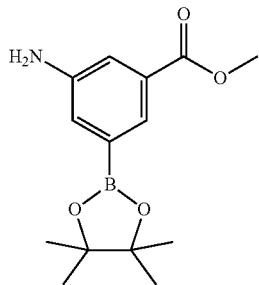

Chemical Formula: C$_{14}$H$_{20}$BNO$_4$
Exact Mass: 277.15
Molecular Weight: 277.13

To a solution of methyl 3-amino-5-bromobenzoate (61b, 219 mg, 0.950 mmol) in 1,4-dioxane (20 mL) were added bis(pinacolato)diboron (290 mg, 1.14 mmol), PdCl$_2$(dppf) (23 mg, 28.5 μmol) and potassium acetate (279 mg, 2.85 mmol), and then this reaction mixture was stirred at 95° C. for 15 h. The reaction mixture was partitioned ethyl acetate (20 mL) and water (10 mL), and the aqueous layer was extracted with ethyl acetate (10 mL×2). The combined organic layer was washed brine (5 mL), dried over MgSO$_4$, filtered and evaporated under reduced pressure. The residue was purified by silica gel column chromatography (hexane:ethyl acetate=4:1) to afford compound 62 (180 mg, 68%) as a white solid; $^1$H NMR (400 MHz, CDCl$_3$) δ 7.88 (s, 1H), 7.46 (s, 1H), 7.31 (d, J=2.4 Hz, 1H), 3.91 (s, 3H), 1.36 (s, 12H); MS (ESI, m/z) 278.2 [M+1]$^+$; ESI-HRMS calcd. m/z for C$_{14}$H$_{21}$NO$_4$$^{11}$B 278.1564, found 278.1565 [M+1]$^+$.

Methyl 5-amino-4'-carbamoyl-[1,1'-biphenyl]-3-carboxylate (63a)

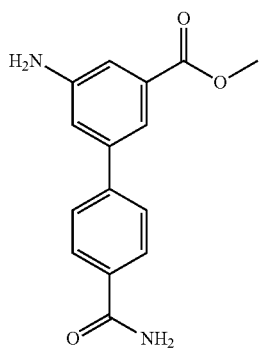

Chemical Formula: C$_{15}$H$_{14}$N$_2$O$_3$
Exact Mass: 270.10
Molecular Weight: 270.29

To a solution of compound 62 (90 mg, 0.325 mmol) in 1,2-dimethoxyethane (4 mL) were added compound 4-bromobenzamide (71 mg, 0.357 mmol), Pd(PPh$_3$)$_4$ (7.5 mg, 6.5 mol) and potassium carbonate (90 mg, 0.650 mmol), and then this reaction mixture was purged with nitrogen for 30 min and stirred at 80° C. for 15 h. The reaction mixture was partitioned ethyl acetate (20 mL) and water (10 mL), and the aqueous layer was extracted with ethyl acetate (20 mL×2). The combined organic layer was washed brine (3 mL), dried over MgSO$_4$, filtered and evaporated under reduced pressure. The residue was purified by silica gel column chromatography (hexane:ethyl acetate=1:1) to afford compound 63a (55 mg, 63%) as a white solid; $^1$H NMR (400 MHz, CDCl$_3$) δ 7.90 (d, J=8.20 Hz, 2H), 7.70-7.68 (m, 3H), 7.40 (s, 1H), 7.11 (s, 1H), 3.95 (s, 3H), 3.92 (broad s, 1.5H; NH$_2$); MS (ESI, m/z) 271.1 [M+1]$^+$; ESI-HRMS calcd. m/z for C$_{15}$H$_{15}$N$_2$O$_3$ 271.1083, found 271.1080 [M+1]$^+$.

tert-Butyl 4-(3'-amino-5'-(methoxycarbonyl)-[1,1'-biphenyl]-4-yl)piperidine-1-carboxylate (63b)

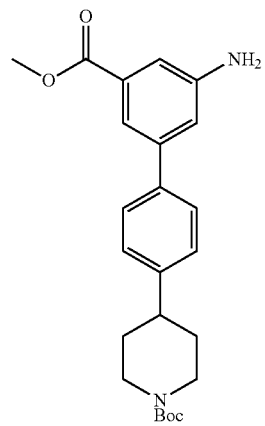

Chemical Formula: C$_{24}$H$_{30}$N$_2$O$_4$
Exact Mass: 410.22
Molecular Weight: 410.51

Compound 62 (90 mg, 0.325 mmol) was converted to compound 63b (54 mg, 41%) as a white solid, using similar procedure used in the preparation of compound 63a; $^1$H NMR (400 MHz, CDCl$_3$) δ 7.68 (s, 1H), 7.56 (d, J=8.16 Hz, 2H), 7.34 (s, 1H), 7.30 (merged with CHCl$_3$ peak, 2H), 7.09-7.08 (m, 1H), 4.03 (broad s, 2H), 3.93 (s, 3H), 2.84 (t, J=12.06 Hz, 2H), 2.75-2.67 (m, 1H), 1.88 (d, J=13.6 Hz, 2H), 1.73-1.62 (m, 2H), 1.51 (s, 9H); MS (ESI, m/z) 355.1 [M+1-tert-butyl]$^+$, 323.1 [M+1-Boc]$^+$.

Methyl 4'-carbamoyl-5-(4-(trifluoromethyl)benzamido)-[1,1'-biphenyl]-3-carboxylate (64a)

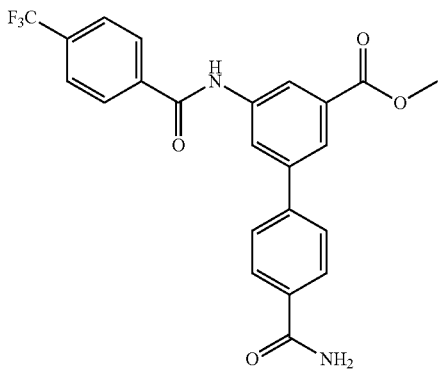

Chemical Formula: $C_{23}H_{17}F_3N_2O_4$
Exact Mass: 442.11
Molecular Weight: 442.39

To a solution of compounds 63a (20 mg, 0.074 mmol) in N,N-dimethylformamide (2 mL) were added 4-(trifluoromethyl)benzoic acid (21 mg, 0.111 mmol), HATU (31 mg, 0.081 mmol) and N,N-diisopropylethylamine (39 µL, 0.222 mmol), and then this reaction mixture was stirred at room temperature for 15 h. The reaction mixture was partitioned ethyl acetate (10 mL) and water (10 mL), and the aqueous layer was extracted with ethyl acetate (10 mL×2). The combined organic layer was washed brine (3 mL), dried over MgSO$_4$, filtered and evaporated under reduced pressure. The residue was purified by silica gel column chromatography (hexane:ethyl acetate=1:1) to afford compound 64a (33 mg, 99%) as a white solid; $^1$H NMR (400 MHz, CDCl$_3$) δ 8.42 (s, 1H), 8.15 (d, J=9.60 Hz, 2H), 8.07 (s, 1H), 8.05 (s, 1H), 7.94 (d, J=7.80 Hz, 2H), 7.83 (d, J=8.12 Hz, 2H), 7.78 (d, J=8.16 Hz, 2H), 4.00 (s, 3H); MS (ESI, m/z) 443.1 [M+1]$^+$; ESI-HRMS calcd. m/z for $C_{23}H_8N_2O_4F_3$ 443.1219, found 443.1227 [M+1]$^+$.

tert-Butyl 4-(3'-(4-(hydroxymethyl)cubane-1-carboxamido)-5'-(methoxycarbonyl)-[1,1'-biphenyl]-4-yl)piperidine-1-carboxylate (64b)

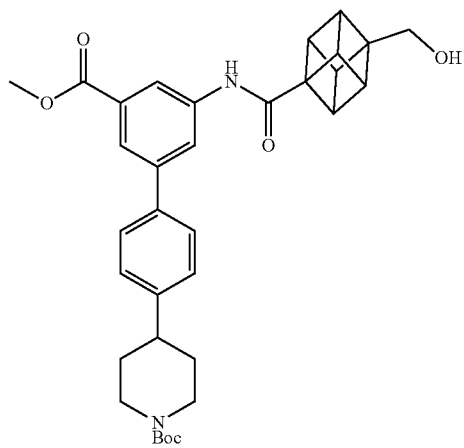

Chemical Formula: $C_{34}H_{38}N_2O_6$
Exact Mass: 570.27
Molecular Weight: 570.69

Compound 63b (28 mg, 68.2 µmol) and 4-(hydroxymethyl)cubane-1-carboxylic acid (13 mg, 75.0 µmol) were converted to compound 64b (27 mg, 69%) as a white solid, using similar procedure used in the preparation of compound 64a; $^1$H NMR (400 MHz, CDCl$_3$) δ 8.30 (s, 1H), 8.04 (s, 1H), 7.61 (d, J=7.96 Hz, 2H), 7.34 (s, 1H), 7.30 (d, J=8.28 Hz, 2H), 4.27 (s, 5H), 3.98 (s, 3H), 3.96 (s, 3H), 3.85 (s, 2H), 2.91-2.82 (m, 2H), 2.75-2.69 (m, 1H), 1.87 (d, J=12.24 Hz, 2H), 1.73-1.65 (m, 2H), 1.51 (s, 9H).

Methyl 5-(4-(hydroxymethyl)cubane-1-carboxamido)-4'-(piperidin-4-yl)-[1,1'-biphenyl]-3-carboxylate (65)

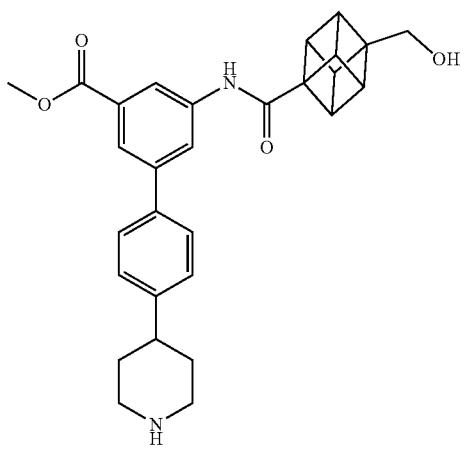

Chemical Formula: $C_{29}H_{30}N_2O_4$
Exact Mass: 470.22
Molecular Weight: 470.57

The reaction mixture of compound 64b (20 mg, 35.0 µmol) in 1N HCl/dioxane solution (1 mL) was stirred at room temperature for 15 h. After all volatiles was evaporated under reduced pressure, the residue was purified by silica gel column chromatography (dichloromethane:methanol=3:1) to afford methyl ester compound (65, 11 mg, 67%) as a white solid; $^1$H NMR (400 MHz, CD$_3$OD) δ 8.27 (s, 1H), 8.25 (s, 1H), 8.00 (t, J=1.50 Hz, 1H), 7.65 (d, J=8.28 Hz, 2H), 7.41 (d, J=8.24 Hz, 2H), 4.25 (t, J=4.90 Hz, 3H), 3.96 (s, 3H), 3.93 (t, J=4.94 Hz, 3H), 3.73 (s, 2H), 3.49 (d, J=12.52 Hz, 2H), 3.18-3.11 (m, 2H), 3.00-2.94 (m, 1H), 2.11 (d, J=12.84 Hz, 2H), 2.03-1.93 (m, 2H); MS (ESI, m/z) 471.2 [M+1]$^+$; ESI-HRMS calcd. m/z for $C_{29}H_{31}N_2O_4$ 471.2284, found 471.2282 [M+1]$^+$.

Methyl 3-bromo-5-formylbenzoate (66b)

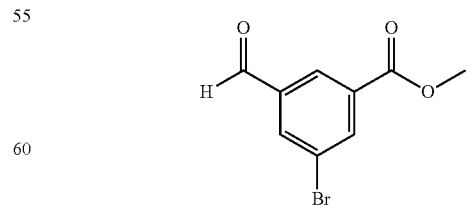

Chemical Formula: $C_9H_7BrO_3$
Exact Mass: 241.96
Molecular Weight: 243.06

To a solution of 3-bromo-5-formylbenzoic acid (66a, 500 mg, 2.18 mmol) in methanol (25 mL) was added concentrated $H_2SO_4$ (1.16 mL, 21.8 mmol) at room temperature, and this reaction mixture was stirred at 60° C. for 15 h. After the solvent was evaporated under reduced pressure, the residue was partitioned ethyl acetate (20 mL) and saturated sodium bicarbonate solution (20 mL), and extracted with ethyl acetate (20 mL×2). The combined organic layer was washed brine (5 mL), dried over $MgSO_4$, filtered and evaporated under reduced pressure. The residue was purified by silica gel column chromatography (hexane:ethyl acetate=50:1) to afford compound 66b (287 mg, 54%) as a white solid; $^1$H NMR (400 MHz, $CDCl_3$) δ 10.04 (s, 1H), 8.47 (s, 1H), 8.43 (s, 1H), 8.22 (s, 1H), 4.00 (s, 3H); MS (ESI, m/z) 243.0, 245.0 [M+1]$^+$; ESI-HRMS calcd. m/z for $C_9H_8O_3{}^{79}Br$ 242.9657, found 242.9656 [M+1]$^+$.

3-Bromo-5-(methoxycarbonyl)benzoic acid (67)

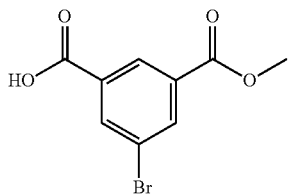

Chemical Formula: $C_9H_7BrO_4$
Exact Mass: 257.95
Molecular Weight: 259.06

To a solution of compound 66b (30 mg, 0.123 mmol) in N,N-dimethylformamide (1 mL) was added oxone (38 mg, 0.123 mmol), and this reaction mixture was stirred at room temperature for 15 h. The reaction mixture was partitioned ethyl acetate (5 mL) and saturated $NaHCO_3$ aqueous solution (5 mL), and the organic layer was extracted with saturated $NaHCO_3$ aqueous solution (5 ml×2). The basic aqueous layer was acidified with 4N HCl solution, and extracted with ethyl acetate (10 ml×2). The combined organic layer was washed brine (5 mL), dried over $MgSO_4$, filtered and evaporated under reduced pressure to afford compound 67 (25 mg, 78%) as a white solid; $^1$H NMR (400 MHz, $CDCl_3$) δ 8.69 (s, 1H), 8.43 (s, 2H), 3.99 (s, 3H); MS (ESI, m/z) 259.0, 261.0 [M+1]$^+$; ESI-HRMS calcd. m/z for $C_9H_8O_4{}^{79}Br$ 258.9606, found 258.9609 [M+1]$^+$.

Methyl 3-bromo-5-((4-(trifluoromethyl)phenyl)carbamoyl)benzoate (68)

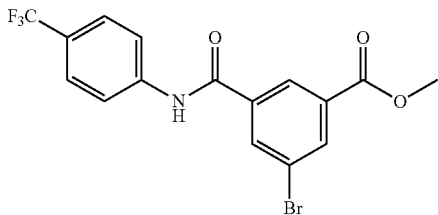

Chemical Formula: $C_{16}H_{11}BrF_3NO_3$
Exact Mass: 400.99
Molecular Weight: 402.17

To a solution of compound 67 (20 mg, 0.0778 mmol) in dichloromethane (3 mL) was added thionyl chloride (86 μL, 0.0856 mmol; 1M solution in dichloromethane) and triethylamine (16 μL, 0.117 mmol) at 0° C., and this reaction mixture was stirred at the same temperature for 1 h. After the solvent was removed under reduced pressure, the residue was dissolved in dichloromethane. p-(trifluoromethyl)aniline (30 μL, 0.234 mmol) and triethylamine (16 μL, 0.117 mmol) were added, and the reaction mixture was stirred at room temperature for 15 h. The reaction mixture was partitioned dichloromethane (10 mL) and water (5 mL), and extracted with dichloromethane (10 mL×2). The combined organic layer was dried over $MgSO_4$, filtered and evaporated under reduced pressure. The residue was purified by silica gel column chromatography (hexane:ethyl acetate=6:1) to afford compound 68 (14 mg, 45%) as a white solid; $^1$H NMR (400 MHz, $CDCl_3$) δ 8.42 (s, 1H), 8.38 (s, 1H), 8.29 (s, 1H), 8.03 (s, 1H), 7.81 (d, J=8.44 Hz, 2H), 7.67 (d, J=8.52 Hz, 2H), 4.00 (s, 3H); MS (ESI, m/z) 402.0, 404.0 [M+1]$^+$; ESI-HRMS calcd. m/z for $C_{16}H_{12}NO_3F_3{}^{79}Br$ 401.9953, found 401.9950 [M+1]$^+$.

Methyl 4'-carbamoyl-5-((4-(trifluoromethyl)phenyl)carbamoyl)-[1,1'-biphenyl]-3-carboxylate (69)

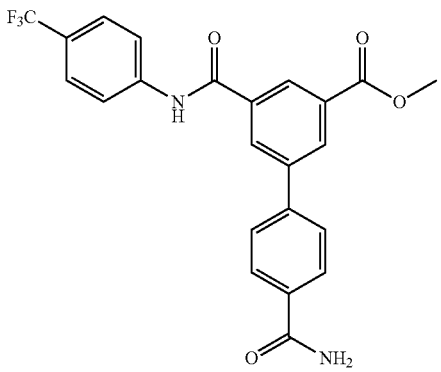

Chemical Formula: $C_{23}H_{17}F_3N_2O_4$
Exact Mass: 442.11
Molecular Weight: 442.39

To a solution of compound 68 (13 mg, 32.3 μmol) in 1,4-dioxane (2 mL) and water (0.2 mL) were added 4-aminocarbonylphenylboronic acid pinacol ester$^{Ref}$ (16 mg, 64.6 μmol), $PdCl_2(PPh_3)_2$ (2.3 mg, 3.23 μmol) and sodium carbonate (6.5 mg, 64.6 μmol), and then this reaction mixture was stirred at 80° C. for 2 h. The reaction mixture was partitioned ethyl acetate (10 mL) and water (5 mL), and the aqueous layer was extracted with ethyl acetate (5 mL×2). The combined organic layer was washed brine (3 mL), dried over $MgSO_4$, filtered and evaporated under reduced pressure. The residue was purified by silica gel column chromatography (dichloromethane:ethyl acetate=1:1) to afford compound 69 (9 mg, 63%) as a white solid; $^1$H NMR (400 MHz, $CD_3OD$) δ 8.64 (s, 1H), 8.54 (s, 1H), 8.53 (s, 1H), 8.05 (d, J=8.20 Hz, 2H), 8.00 (d, J=8.36 Hz, 2H), 7.89 (d, J=8.28 Hz, 2H), 7.70 (d, J=8.72 Hz, 2H), 4.02 (s, 3H); MS (ESI, m/z) 443.1 [M+1]$^+$; ESI-HRMS calcd. m/z for $C_{23}H_{18}N_2O_4F_3$ 443.1219, found 443.1217 [M+1]$^+$.

Methyl 3-((2-amino-5-(trifluoromethyl)phenyl)ethynyl)-5-bromobenzoate (71a)

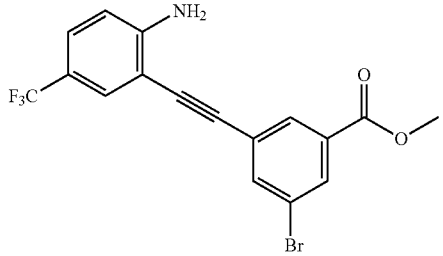

Chemical Formula: C₁₇H₁₁BrF₃NO₂
Exact Mass: 396.99
Molecular Weight: 398.18

To a solution of 2-iodo-4-(trifluoromethyl)aniline (119 mg, 0.417 mmol), PdCl$_2$(PPh$_3$)$_2$ (2.4 mg, 3.47 μmol) and copper iodide (0.7 mg, 3.47 μmol) in triethylamine (6 mL) was added dropwise a solution of 70 (83 mg, 0.347 mmol) in triethylamine (4 mL), and then the reaction mixture was stirred at room temperature for 1 h. The reaction mixture was partitioned ethyl acetate (20 mL) and water (10 mL), and the aqueous layer was extracted with ethyl acetate (10 mL×2). The combined organic layer was washed brine (3 mL), dried over MgSO$_4$, filtered and evaporated under reduced pressure. The residue was purified by silica gel column chromatography (hexane:ethyl acetate=4:1) to afford compound 71a (113 mg, 82%) as a white solid; ¹H NMR (400 MHz, CDCl$_3$) δ 8.17 (s, 1H), 8.13 (s, 1H), 7.86 (s, 1H), 7.64 (s, 1H), 7.40 (d, J=8.52 Hz, 1H), 6.78 (d, J=8.56 Hz, 1H), 4.61 (broad s, 2H), 3.97 (s, 3H); MS (ESI, m/z) 398.0, 400.0 [M+1]⁺; ESI-HRMS calcd. m/z for C$_{17}$H$_{12}$NO$_2$F$_3$⁷⁹Br 398.0003, found 398.0007 [M+1]⁺.

Methyl 3-((2-amino-4-(trifluoromethyl)phenyl)ethynyl)-5-bromobenzoate (71b)

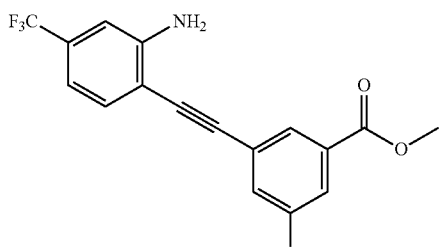

Chemical Formula: C₁₇H₁₁BrF₃NO₂
Exact Mass: 396.99
Molecular Weight: 398.18

Compound 70 (60 mg, 0.251 mmol) and 2-iodo-5-(trifluoromethyl)aniline (97 mg, 0.301 mmol) were converted to compound 71b (87 mg, 87%) as a white solid, using similar procedure used in the preparation of compound 71a; ¹H NMR (400 MHz, CDCl$_3$) δ 8.18 (s, 1H), 8.14 (s, 1H), 7.87 (s, 1H), 7.46 (d, J=8.52 Hz, 1H), 6.99-6.97 (m, 2H), 4.49 (broad s, 2H), 3.98 (s, 3H); MS (ESI, m/z) 398.0, 400.0 [M+1]⁺; ESI-HRMS calcd. m/z for C$_{17}$H$_{12}$NO$_2$F$_3$⁷⁹Br 398.0003, found 398.0009 [M+1]⁺.

Methyl 3-bromo-5-(5-(trifluoromethyl)-1H-indol-2-yl)benzoate (72a)

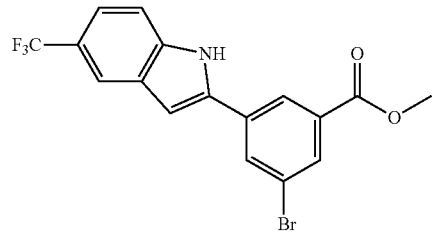

Chemical Formula: C₁₇H₁₁BrF₃NO₂
Exact Mass: 396.99
Molecular Weight: 398.18

The mixture of compound 71a (20 mg, 50.2 μmol) and PdCl$_2$ (1 mg, 5.02 μmol) in N,N-dimethylformamide (2 mL) was stirred at 110° C. for 10 min in microwave. After microwave irradiation, the solvent was removed under reduced pressure. The residue was purified by silica gel column chromatography (hexane:ethyl acetate=6:1) to afford compound 72a (13 mg, 65%) as a white solid; ¹H NMR (400 MHz, CDCl$_3$) δ 8.68 (s, 1H), 8.27 (s, 1H), 8.16 (s, 1H), 8.03 (s, 1H), 7.96 (s, 1H), 7.51 (d, J=8.48 Hz, 1H), 7.48 (d, J=8.56 Hz, 1H), 7.01 (s, 1H), 4.00 (s, 3H); MS (ESI, m/z) 398.0, 400.0 [M+1]⁺; ESI-HRMS calcd. m/z for C$_{17}$H$_{12}$NO$_2$F$_3$⁷⁹Br 398.0003, found 398.0000 [M+1]⁺.

Methyl 3-bromo-5-(6-(trifluoromethyl)-1H-indol-2-yl)benzoate (72b)

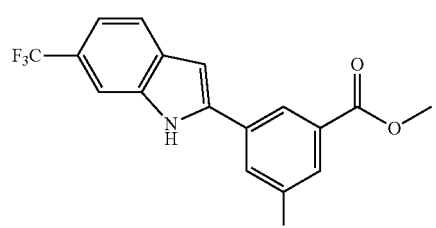

Chemical Formula: C₁₇H₁₁BrF₃NO₂
Exact Mass: 396.99
Molecular Weight: 398.18

Compound 71b (76 mg, 0.191 mmol) was converted to compound 72b (47 mg, 62%) as a white solid, using similar procedure used in the preparation of compound 72a; ¹H NMR (400 MHz, CDCl$_3$) δ 8.65 (broad s, 1H), 8.28 (s, 1H), 8.17 (s, 1H), 8.04 (s, 1H), 7.76-7.72 (m, 2H), 7.40 (d, J=8.44 Hz, 1H), 7.00 (s, 1H), 4.01 (s, 3H); MS (ESI, m/z) 398.0, 400.0 [M+1]⁺; ESI-HRMS calcd. m/z for C$_{17}$H$_{12}$NO$_2$F$_3$⁷⁹Br 398.0003, found 398.0002 [M+1]⁺.

Methyl 4'-carbamoyl-5-(5-(trifluoromethyl)-1H-indol-2-yl)-[1,1'-biphenyl]-3-carboxylate (73a)

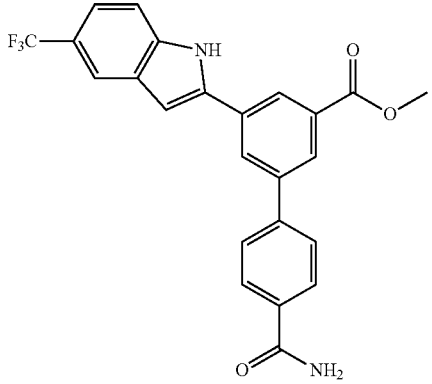

Chemical Formula: $C_{24}H_{17}F_3N_2O_3$
Exact Mass: 438.12
Molecular Weight: 438.41

Molecular Weight: 438.41

Compound 72a (13 mg, 32.6 μmol) was converted to compound 73a (8 mg, 55%) as a white solid, using similar procedure used in the preparation of compound 69 at 80° C. for 15 h; $^1$H NMR (400 MHz, CDCl$_3$) δ 8.54 (s, 1H), 8.40 (s, 1H), 8.29 (s, 1H), 8.06 (d, J=7.24 Hz, 2H), 7.95 (s, 1H), 7.90 (d, J=7.25 Hz, 2H), 7.59 (d, J=8.48 Hz, 1H), 7.41 (d, J=8.20 Hz, 1H), 7.18 (s, 1H), 4.03 (s, 3H); MS (ESI, m/z) 439.1 [M+1]$^+$; ESI-HRMS calcd. m/z for $C_{24}H_{18}N_2O_3F_3$ 439.1270, found 439.1272 [M+1]$^+$.

Methyl 4'-carbamoyl-5-(6-(trifluoromethyl)-1H-indol-2-yl)-[1,1'-biphenyl]-3-carboxylate (73b)

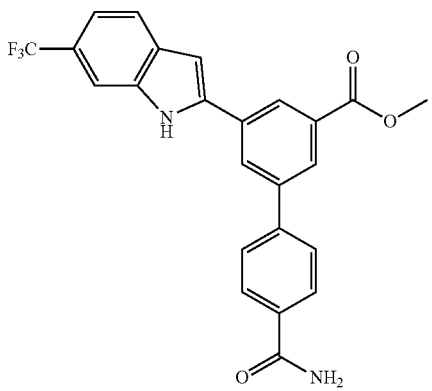

Chemical Formula: $C_{24}H_{17}F_3N_2O_3$
Exact Mass: 438.12
Molecular Weight: 438.41

Compound 72b (25 mg, 62.8 μmol) was converted to compound 73b (20 mg, 72%) as a white solid, using similar procedure used in the preparation of compound 69 at 80° C. for 15 h; $^1$H NMR (400 MHz, CD$_3$OD) δ 8.52 (s, 1H), 8.38 (s, 1H), 8.28 (s, 1H), 8.05 (d, J=8.16 Hz, 2H), 7.88 (d, J=8.24 Hz, 2H), 7.76-7.74 (m, 2H), 7.30 (d, J=8.60 Hz, 1H), 7.13 (s, 1H), 4.01 (s, 3H); MS (ESI, m/z) 439.1 [M+1]$^+$; ESI-HRMS calcd. m/z for $C_{24}H_{18}N_2O_3F_3$ 439.1270, found 439.1272 [M+1]$^+$.

Methyl 3-bromo-5-(5-(trifluoromethyl)-1H-benzo[d]imidazol-2-yl)benzoate (74)

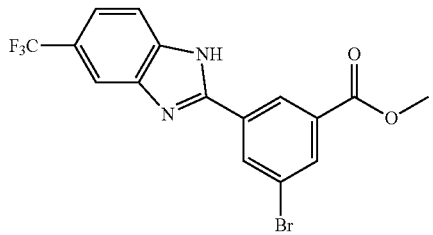

Chemical Formula: $C_{16}H_{10}BrF_3N_2O_2$
Exact Mass: 397.99
Molecular Weight: 399.17

To a solution of compound 66b (20 mg, 0.083 mmol) in N,N-dimethylformamide (3 mL) was added 4-trifluoromethyl-O-phenylenediamine (29 mg, 0.166 mmol) and sodium metabisulfite (32 mg, 0.166 mmol) at room temperature, and this reaction mixture was stirred at 130° C. for 15 h. After cooling, the reaction mixture was partitioned ethyl acetate (20 mL) and water (20 mL), and extracted with ethyl acetate (20 mL×2). The combined organic layer was washed brine (5 mL), dried over MgSO$_4$, filtered and evaporated under reduced pressure. The residue was purified by silica gel column chromatography (hexane:ethyl acetate=6:1) to afford compound 74 (32 mg, 97%) as a white solid; $^1$H NMR (400 MHz, CDCl$_3$) δ 8.57-8.56 (m, 2H), 8.32 (s, 1H), 8.01 (broad s, 1H), 7.76 (broad s, 1H), 7.60 (d, J=8.24 Hz, 1H), 4.01 (s, 3H); MS (ESI, m/z) 399.0, 401.0 [M+1]$^+$; ESI-HRMS calcd. m/z for $C_{16}H_{11}N_2O_2F_3{}^{79}Br$ 398.9956, found 398.9953 [M+1]$^+$.

Methyl 4'-carbamoyl-5-(5-(trifluoromethyl)-1H-benzo[d]imidazol-2-yl)-[1,1'-biphenyl]-3-carboxylate (75)

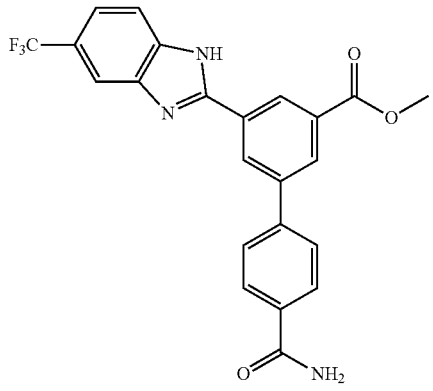

Chemical Formula: $C_{23}H_{16}F_3N_3O_3$
Exact Mass: 439.11
Molecular Weight: 439.39

Compound 74 (12 mg, 30.1 μmol) was converted to compound 75 (5 mg, 38%) as a white solid, using similar procedure used in the preparation of compound 69 at 80° C. for 15 h; $^1$H NMR (400 MHz, CD$_3$OD) δ 8.83 (s, 1H), 8.73 (s, 1H), 8.48 (s, 1H), 8.07 (d, J=8.04 Hz, 2H), 7.98 (broad s, 1H), 7.92 (d, J=8.16 Hz, 2H), 7.80 (broad s, 1H), 7.60 (d, J=8.08 Hz, 1H), 4.04 (s, 3H); MS (ESI, m/z) 440.1 [M+1]$^+$; ESI-HRMS calcd. m/z for C$_{23}$H$_{17}$N$_3$O$_3$F$_3$ 440.1222, found 440.1223 [M+1]$^+$.

Ethyl 3-amino-5-(4-bromophenyl)-1H-pyrrole-2-carboxylate (78)

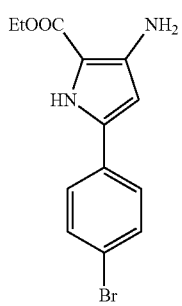

Chemical Formula:
C$_{13}$H$_{13}$BrN$_2$O$_2$
Exact Mass:
308.02
Molecular Weight:
309.16

To a mixture of (4-bromobenzoyl)acetonitrile (76, 287 mg, 1.28 mmol) in dichloromethane (1 mL) were added p-toluenesulfonic anhydride (502 mg, 1.54 mmol) and triethylamine (194 mg, 0.27 mL, 1.92 mmol), and the reaction mixture was stirred at room temperature for 3 h. The reaction mixture was partitioned dichloromethane (10 mL) and water (10 mL) and extracted with dichloromethane (10 mL×2). The combined organic layer was dried over MgSO$_4$, filtered and evaporated under reduced pressure to give beige solid (526 mg, >100%). To a solution of sodium ethoxide (262 mg, 1.25 mL, 3.85 mmol, 21% wt ethanol solution) in ethanol (4 mL) was added a solution of the obtained beige solid (426 mg, 1.28 mmol) and diethyl aminomalonate hydrochloride (281 mg, 1.33 mmol) in ethanol (6 mL) and tetrahydrofuran (3 mL) dropwise over 10 min. This reaction mixture was stirred at room temperature for 30 min, and all solvent was removed under reduced pressure. The residue was partitioned ethyl acetate (10 mL) and water (10 mL) and extracted with ethyl acetate (10 mL×2). The combined organic layer was washed brine (5 mL), dried over MgSO$_4$, filtered and evaporated under reduced pressure. The residue was purified by silica gel column chromatography (hexane:ethyl acetate=5:1) to afford compound 78 (127 mg, 40% from 76) as a beige solid; $^1$H NMR (400 MHz, CDCl$_3$) δ 7.53 (d, J=8.40 Hz, 2H), 7.38 (d, J=8.40 Hz, 2H), 6.03 (d, J=2.84 Hz, 1H), 4.37 (q, J=7.06 Hz, 2H), 1.40 (t, J=7.10 Hz, 3H); MS (ESI, m/z) 309.0, 311.0 [M+1]$^+$; ESI-HRMS calcd. m/z for C$_3$H$_4$N$_2$O$_2$$^{79}$Br 309.0239, found 309.0240 [M+1]$^+$.

tert-Butyl 4-(4-(4-amino-5-(ethoxycarbonyl)-1H-pyrrol-2-yl)phenyl)-3,6-dihydropyridine-1(2H)-carboxylate (79)

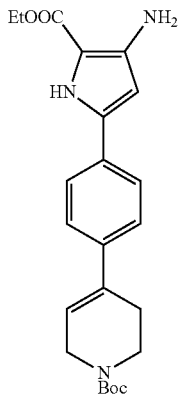

Chemical Formula:
C$_{23}$H$_{29}$N$_3$O$_4$
Exact Mass:
411.22
Molecular Weight:
411.50

To a mixture of compound 78 (23 mg, 74.4 μmol), N-Boc-1,2,3,6-tetrahydropyridine-4-boronic acid pinacol ester (28 mg, 89.2 μmol) and PdCl$_2$(dppf) (6 mg, 7.44 μmol) in N,N-dimethylformamide (1 mL) was added 2M NaOH (75 μL, 0.148 mmol), and this reaction mixture was stirred at room temperature for 1 h. The mixture was partitioned ethyl acetate (10 mL) and water (10 mL), and the aqueous layer was extracted with ethyl acetate (10 mL×2). The combined organic layer was washed brine (5 mL), dried over MgSO$_4$, filtered and evaporated under reduced pressure. The residue was purified by silica gel column chromatography (hexane:ethyl acetate=2:1) to afford compound 79 (24 mg, 78%) as a beige solid; $^1$H NMR (400 MHz, CDCl$_3$) δ 7.49 (d, J=8.20 Hz, 2H), 7.42 (d, J=8.28 Hz, 2H), 6.11 (broad s, 1H), 6.05 (d, J=2.84 Hz, 1H), 4.37 (q, J=7.01 Hz, 2H), 4.12 (s, 2H), 3.67 (t, J=5.66 Hz, 2H), 2.56 (s, 2H), 1.52 (s, 9H), 1.41 (t, J=7.10 Hz, 3H); MS (ESI, m/z) 412.2 [M+1]$^+$.

tert-Butyl 4-(4-(4-azido-5-(ethoxycarbonyl)-1H-pyrrol-2-yl)phenyl)-3,6-dihydropyridine-1(2H)-carboxylate (80)

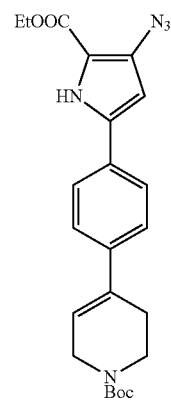

Chemical Formula:
C$_{23}$H$_{27}$N$_5$O$_4$
Exact Mass:
437.21
Molecular Weight:
437.50

To a mixture of 79 (20 mg, 48.6 μmol) in N,N-dimethylformamide (1.4 mL) and water (0.6 mL) was added 4N HCl aqeuous solution (24 μL, 97.2 μmol). After 5 min, sodium nitrite (7 mg, 0.101 mmol) was added to the above reaction mixture at 0° C., and then sodium azide was added after 30 min. The mixture stirred at room temperature for 30 min, and partitioned ethyl acetate (10 mL) and water (15 mL). The aqueous layer was extracted with ethyl acetate (10 mL×2). The combined organic layer was washed brine (5 mL), dried over MgSO$_4$, filtered and evaporated under reduced pressure. The residue was purified by silica gel column chromatography (hexane:ethyl acetate=4:1) to afford compound 80 (16 mg, 75%) as a beige solid; $^1$H NMR (400 MHz, CDCl$_3$) δ 8.94 (s, 1H), 7.51 (d, J=8.40 Hz, 2H), 7.45 (d, J=8.44 Hz, 2H), 6.40 (d, J=3.08 Hz, 1H), 6.13 (s, 1H), 4.41 (q, J=7.10 Hz, 2H), 4.12 (s, 2H), 3.68 (t, J=5.32 Hz, 2H), 2.56 (s, 2H), 1.52 (s, 9H), 1.43 (t, J=7.06 Hz, 3H); MS (ESI, m/z) 410.2 [M+1-N$_2$]$^+$; ESI-HRMS calcd. m/z for C$_{23}$H$_{28}$N$_3$O$_4$ 410.2080, found 410.2086 [M+1-N$_2$]$^+$.

tert-Butyl 4-(4-(5-(ethoxycarbonyl)-4-(4-(4-(trifluoromethyl)phenyl)-1H-1,2,3-triazol-1-yl)-1H-pyrrol-2-yl)phenyl)-3,6-dihydropyridine-1(2H)-carboxylate (81)

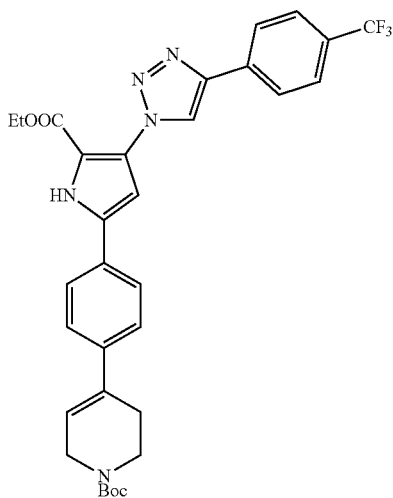

Chemical Formula: C$_{32}$H$_{32}$F$_3$N$_5$O$_4$
Exact Mass: 607.24
Molecular Weight: 607.63

To a mixture of compound 80 (15 mg, 34.3 μmol) and 4-ethynyl-α,α,α-trifluorotoluene (9 μL, 9.39 mg, 55.2 μmol) in dimethyl sulfoxide:water (9:1, 1 mL) were added sodium ascorbate (10 mg, 51.4 μmol) and CuSO$_4$.5H$_2$O (4 mg, 17.1 μmol) sequentially. The reaction mixture was stirred at room temperature for 1 h, and partitioned between ethyl acetate (10 mL) and water (10 mL). The aqueous layer was extracted with ethyl acetate (10 mL×2). The combined organic layer was washed brine (5 mL), dried over MgSO$_4$, filtered and evaporated under reduced pressure. The residue was purified by silica gel column chromatography (hexane: ethyl acetate=2:1) to afford compound 81 (16 mg, 77%) as a beige solid; $^1$H NMR (400 MHz, CDCl$_3$) δ 9.32 (s, 1H), 8.79 (s, 1H), 8.07 (d, J=8.16 Hz, 2H), 7.73 (d, J=8.00 Hz, 2H), 7.61 (d, J=8.08 Hz, 2H), 7.51 (d, J=7.92 Hz, 2H), 7.11 (s, 1H), 6.17 (s, 1H), 4.39 (q, J=7.00 Hz, 2H), 4.14 (s, 2H), 3.69 (t, J=5.40 Hz, 2H), 2.58 (s, 2H), 1.53 (s, 9H), 1.36 (t, J=6.98 Hz, 3H); MS (ESI, m/z) 608.2 [M+1]$^+$; ESI-HRMS calcd. m/z for C$_{32}$H$_{33}$N$_5$O$_4$F$_3$ 608.2485, found 608.2491 [M+1]$^+$.

Ethyl 5-(4-(1,2,3,6-tetrahydropyridin-4-yl)phenyl)-3-(4-(4-(trifluoromethyl)phenyl)-1H-1,2,3-triazol-1-yl)-1H-pyrrole-2-carboxylate (82)

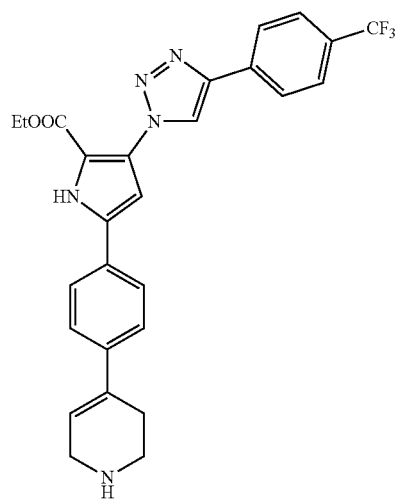

Chemical Formula: C$_{27}$H$_{24}$F$_3$N$_5$O$_2$
Exact Mass: 507.19
Molecular Weight: 507.52

Method B: Yield 60%; $^1$H NMR (400 MHz, CD$_3$OD) δ 8.90 (s, 1H), 8.13 (d, J=8.04 Hz, 2H), 7.86 (d, J=8.36 Hz, 2H), 7.80 (d, J=8.16 Hz, 2H), 7.62 (d, J=8.44 Hz, 2H), 7.01 (s, 1H), 6.28 (broad s, 1H), 4.29 (q, J=7.12 Hz, 2H), 3.91-3.88 (m, 2H), 3.50 (t, J=6.12 Hz, 2H), 2.87-2.84 (m, 2H), 0.91 (t, J=6.12 Hz, 3H); MS (ESI, m/z) 508.2 [M+1]$^+$; ESI-HRMS calcd. m/z for C$_{27}$H$_{25}$N$_5$O$_2$F$_3$ 508.1960, found 508.1960 [M+1]$^+$.

Methyl 3-bromo-2-methyl-5-((trimethylsilyl)ethynyl)benzoate (84)

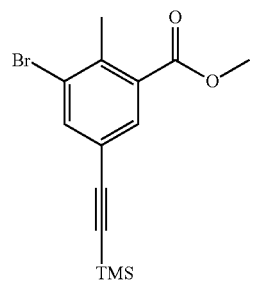

Chemical Formula: C$_{14}$H$_{17}$BrO$_2$Si
Exact Mass: 324.02
Molecular Weight: 325.28

To a solution of compound 83 (100 mg, 0.281 mmol) in N,N-dimethylformamide (2 mL) were added PdCl$_2$(PPh$_3$)$_2$ (40 mg, 0.056 mmol), copper iodide (6 mg, 0.030 mmol), triethylamine (0.120 mL, 0.843 mmol), TMS-acetylene (0.043 mL, 0.309 mmol), and then this reaction mixture was stirred at room temperature for 5 h. After the solvent was evaporated under reduced pressure, the residue was purified by silica gel column chromatography (hexane:ethyl acetate=50:1) to afford compound 84 (91 mg, 99%) as a colorless syrup; $^1$H NMR (400 MHz, CDCl$_3$) δ 7.82 (s, 1H), 7.79 (s, 1H), 3.89 (s, 3H), 2.61 (s, 3H), 0.24 (s, 9H).

Methyl 3-bromo-5-ethynyl-2-methylbenzoate (85)

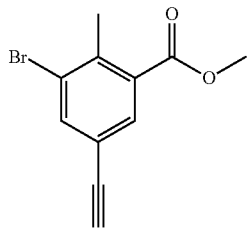

Chemical Formula: C$_{11}$H$_9$BrO$_2$
Exact Mass: 251.98
Molecular Weight: 253.10

To a solution of compound 84 (91 mg, 0.279 mmol) in tetrahydrofuran (10 mL) was added tetrabutylammonium fluoride (0.028 mL, 1 M solution in tetrahydrofuran), and then this reaction mixture was stirred at room temperature for 0.5 h. After being neutralized with acetic acid, the mixture was evaporated under reduced pressure. The residue was purified by silica gel column chromatography (hexane:ethyl acetate=30:1) to afford compound 85 (66 mg, 93%) as a white solid; $^1$H NMR (400 MHz, CDCl$_3$) δ 7.85 (s, 1H), 7.81 (s, 1H), 3.90 (s, 3H), 3.10 (s, 1H), 2.62 (s, 3H).

Methyl 3-bromo-2-methyl-5-(1-(4-(trifluoromethyl)phenyl)-1H-1,2,3-triazol-4-yl)benzoate (86)

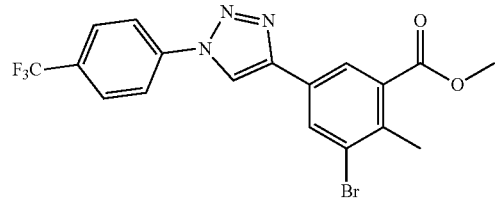

Chemical Formula: C$_{18}$H$_{13}$BrF$_3$N$_3$O$_2$
Exact Mass: 439.01
Molecular Weight: 440.22

To a solution of compound 85 (66 mg, 0.149 mmol) and 1-azido-4-(trifluoromethyl)benzene (42 mg, 0.224 mmol; synthesized according to literature procedures reported) in tetrahydrofuran:water (2 mL, 1:1) were added CuSO$_4$.5H$_2$O (19 mg, 0.076 mmol) and sodium ascorbate (43 mg, 0.217 mmol, freshly prepared 1 M aqueous solution), and then this reaction mixture was stirred at room temperature for 1 h. The reaction mixture was partitioned diethyl ether (10 mL) and water (5 mL), and the aqueous layer was extracted with diethyl ether (10 mL×2). The combined organic layer was washed brine (5 mL), dried over MgSO$_4$, filtered and evaporated under reduced pressure. The residue was purified by silica gel column chromatography (hexane:ethyl acetate=9:1) to afford compound 86 (76 mg, 66%) as a white solid; $^1$H NMR (400 MHz, CDCl$_3$) δ 8.30 (s, 2H), 8.27 (s, 1H), 7.97 (d, J=8.36 Hz, 2H), 7.85 (d, J=8.40 Hz, 2H), 3.95 (s, 3H), 2.68 (s, 3H); MS (ESI, m/z) 440.0, 442.0 [M+1]$^+$; ESI-HRMS calcd. m/z for C$_8$H$_{14}$N$_3$O$_2$F$_3$$^{79}$Br 440.0221, found 440.0227 [M+1]$^+$.

tert-Butyl 4-(3'-(methoxycarbonyl)-2'-methyl-5'-(1-(4-(trifluoromethyl)phenyl)-1H-1,2,3-triazol-4-yl)-[1,1'-biphenyl]-4-yl)piperidine-1-carboxylate (87)

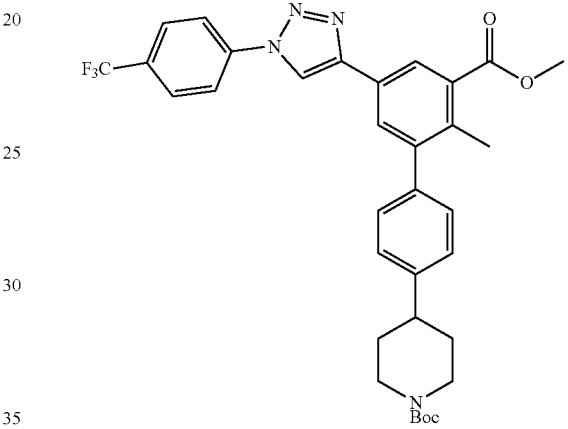

Chemical Formula: C$_{34}$H$_{35}$F$_3$N$_4$O$_4$
Exact Mass: 620.26
Molecular Weight: 620.67

The mixture of compound 86 (40 mg, 0.090 mmol), Pd(PPh$_3$)$_4$ (6 mg, 5.19 µmol) and potassium carbonate (37 mg, 0.267 mmol) in N,N-dimethylformamide (3 mL) was purged with nitrogen gas for 15 min, and then tert-Butyl 4-(4-(4,4,5,5-tetramethyl-1,3,2-dioxaborolan-2-yl)phenyl)piperidine-1-carboxylate (53 mg, 0.136 mmol) was added to the mixture. The mixture was stirred at 85° C. for 12 h, and then allowed to be cooled at room temperature. This mixture was partitioned diethyl ether (5 mL) and water (10 mL). The aqueous layer was extracted with diethyl ether (5 mL×2), and then the combined organic layer was washed with brine (3 mL), dried (MgSO$_4$), filtered and evaporated under reduced pressure. The residue was purified by silica gel column chromatography (hexane:ethyl acetate=4:1) to afford compound 87 (40 mg, 70%) as a white solid; $^1$H NMR (400 MHz, CDCl$_3$) δ 8.35 (s, 1H), 8.28 (s, 1H), 7.96-7.92 (m, 3H), 7.84 (d, J=8.44 Hz, 2H), 7.07 (d, J=8.52 Hz, 2H), 6.78 (d, J=8.56 Hz, 2H), 4.30-4.19 (m, 2H), 3.96 (s, 3H), 2.95-2.72 (m, 3H), 2.47 (s, 3H), 1.90 (d, J=13.12 Hz, 2H), 1.80 (d, J=13.12 Hz, 2H), 1.49 (s, 9H); MS (ESI, m/z) 621.3 [M+1]$^+$; ESI-HRMS calcd. m/z for C$_{34}$H$_{36}$N$_4$O$_4$F$_3$ 621.2689, found 621.2690 [M+1]$^+$.

Methyl 2-methyl-4'-(piperidin-4-yl)-5-(1-(4-(trifluoromethyl)phenyl)-1H-1,2,3-triazol-4-yl)-[1,1'-biphenyl]-3-carboxylate (88)

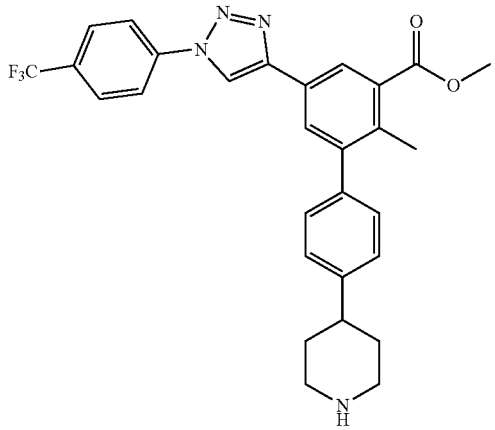

Chemical Formula: $C_{29}H_{27}F_3N_4O_2$
Exact Mass: 520.21
Molecular Weight: 520.56

Method B: Yield 79%; $^1$H NMR (400 MHz, CDCl$_3$) δ 8.35 (s, 1H), 8.29 (s, 1H), 7.96-7.92 (m, 3H), 7.84 (d, J=8.52 Hz, 2H), 7.34-7.29 (m, 2H), 7.09 (d, J=8.40 Hz, 1H), 6.81 (d, J=8.40 Hz, 1H), 3.96 (s, 3H), 3.62-3.52 (m, 2H), 2.90-2.83 (m, 2H), 2.74-2.67 (m, 1H), 2.46 (s, 3H), 2.17-2.11 (m, 2H), 2.06-1.97 (m, 2H); MS (ESI, m/z) 521.2 [M+1]$^+$; ESI-HRMS calcd. m/z for $C_{29}H_{28}N_4O_2F_3$ 521.2164 found 521.2173 [M+1]$^+$.

Methyl 4-bromo-2-(4-(trifluoromethyl)phenyl)-1H-benzo[d]imidazole-6-carboxylate (90)

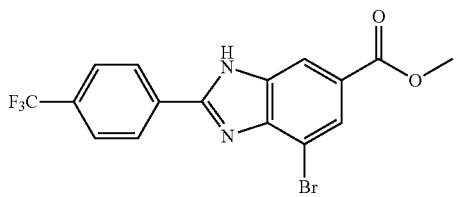

Chemical Formula: $C_{16}H_{10}BrF_3N_2O_2$
Exact Mass: 397.99
Molecular Weight: 399.17

To a solution of compound 89 (200 mg, 0.816 mmol) in N,N-dimethylformamide (10 mL) was added 4-(trifluoromethyl)benzaldehyde (0.222 mL, 1.632 mmol) and sodium metabisulfite (310 mg, 1.632 mmol) at room temperature, and this reaction mixture was stirred at 130° C. for 12 h. After cooling, the reaction mixture was partitioned ethyl acetate (20 mL) and water (20 mL), and extracted with ethyl acetate (20 mL×2). The combined organic layer was washed brine (5 mL), dried over MgSO$_4$, filtered and evaporated under reduced pressure. The residue was purified by silica gel column chromatography (hexane:ethyl acetate=6:1) to afford compound 90 (212 mg, 65%) as a white solid; $^1$H NMR (400 MHz, CDCl$_3$) δ 8.38 (broad s, 1H), 8.25-8.18 (m, 3H), 7.82 (d, J=8.16 Hz, 2H), 3.97 (s, 3H); MS (ESI, m/z) 399.0, 401.0 [M+1]$^+$; ESI-HRMS calcd. m/z for $C_{16}H_{11}N_2O_2F_3{}^{79}Br$ 398.9956, found 398.9950 [M+1]$^+$.

Methyl 4-(4-(1-(tert-butoxycarbonyl)piperidin-4-yl)phenyl)-2-(4-(trifluoromethyl)phenyl)-1H-benzo[d]imidazole-6-carboxylate (91)

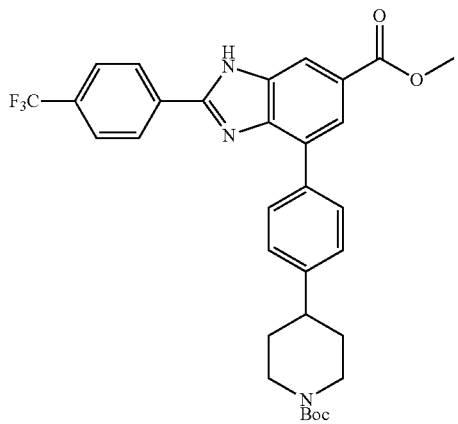

Chemical Formula: $C_{32}H_{32}F_3N_3O_4$
Exact Mass: 579.23
Molecular Weight: 579.62

Compound 90 (30 mg, 0.075 mmol) and tert-butyl 4-(4-(4,4,5,5-tetramethyl-1,3,2-dioxaborolan-2-yl)phenyl)piperidine-1-carboxylate (34 mg, 0.090 mmol) were dissolved in degassed 2M Na$_2$CO$_3$ aqueous solution (15 mg, 0.141 mmol) and 1,4-dioxane (3 mL), and then Pd(PPh$_3$)$_4$ (5 mg, 4.32 μmol) was added to the reaction mixture. The mixture was stirred at 80° C. for 12 h under nitrogen atmosphere. After cooling at room temperature, the mixture was partitioned ethyl acetate (20 mL) and water (10 mL). The aqueous layer was extracted with ethyl acetate (10 mL×2), and then the combined organic layer was washed with brine (3 mL), dried (MgSO$_4$), filtered and evaporated under reduced pressure. The residue was purified by silica gel column chromatography (hexane:ethyl acetate=5:1) to afford compound 91 (19 mg, 43%) as a white solid; $^1$H NMR (400 MHz, CDCl$_3$) δ 8.42 (broad s, 1H), 8.23-8.17 (m, 3H), 7.79 (d, J=8.04 Hz, 2H), 7.40 (d, J=7.84 Hz, 2H), 7.27-7.23 (m, 2H), 3.97 (s, 3H), 2.90-2.70 (m, 3H), 1.93-1.86 (m, 2H), 1.74-1.65 (m, 2H), 1.50 (s, 9H), 1.28-1.24 (m, 2H); MS (ESI, m/z) 580.2 [M+1]$^+$; ESI-HRMS calcd. m/z for $C_{32}H_{33}N_3O_4F_3$ 580.2423, found 580.2434 [M+1]$^+$.

117

Methyl 4-(4-(piperidin-4-yl)phenyl)-2-(4-(trifluoromethyl)phenyl)-1H-benzo[d]imidazole-6-carboxylate (92)

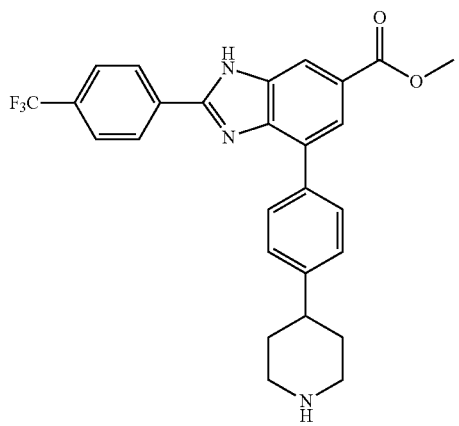

Chemical Formula: $C_{27}H_{24}F_3N_3O_2$
Exact Mass: 479.18
Molecular Weight: 479.50

Method B: Yield 82%; $^1$H NMR (400 MHz, CD$_3$OD) δ 8.36 (d, J=8.00 Hz, 2H), 8.28 (s, 1H), 8.06 (s, 1H), 7.97 (d, J=8.00 Hz, 2H), 7.88 (d, J=8.40 Hz, 2H), 7.48 (d, J=8.00 Hz, 2H), 3.98 (s, 3H), 3.57 (d, J=13.12 Hz, 2H), 3.25-3.17 (m, 2H), 3.08-2.98 (m, 1H), 2.23-2.15 (m, 2H), 2.06-1.95 (m, 2H); MS (ESI, m/z) 480.2 [M+1]$^+$; ESI-HRMS calcd. m/z for $C_{27}H_{25}N_3O_2F_3$ 480.1899 found 480.1902 [M+1]$^+$.

118 tert-Butyl 4-(4-(3-(ethoxycarbonyl)-6-(4-(trifluoromethyl)phenyl)naphthalen-1-yl)phenyl)piperidine-1-carboxylate-3,4-t$_2$ (93)

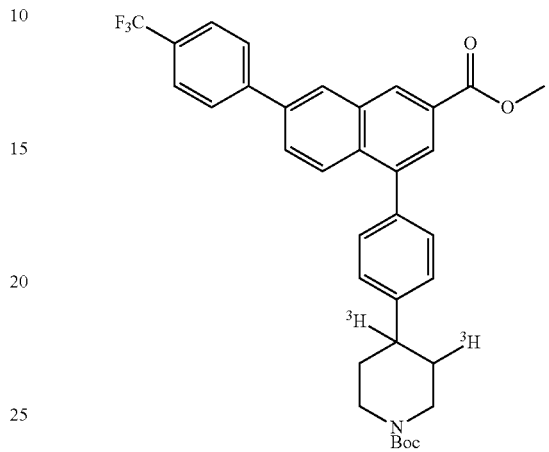

Chemical Formula: $C_{36}H_{34}T_2F_3NO_4$
Exact Mass: 607.28
Molecular Weight: 607.70

Example 2

This example demonstrates the inhibition of hP2Y$_{14}$R antagonist binding, determined using flow cytometry of whole hP2Y$_{14}$R—CHO cells in the presence of a fixed concentration (20 nM) of 3a (mean±SEM, n=3-6), in accordance with an embodiment of the invention. The results for compounds of formula (I) are set forth in Table 1. The results for compounds of formulas (II), (III), (IV), (V), and (VI) are set forth in Table 2.

TABLE 1

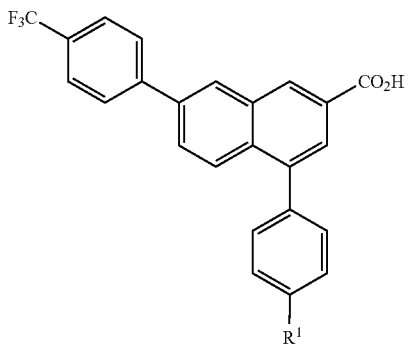

1, 3, 5-14, 17

TABLE 1-continued
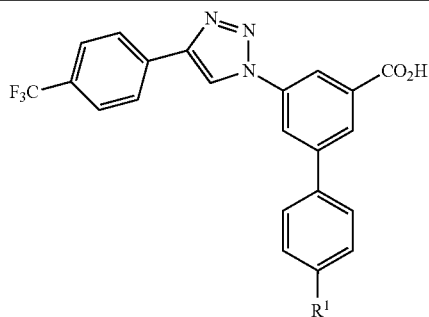
2, 4
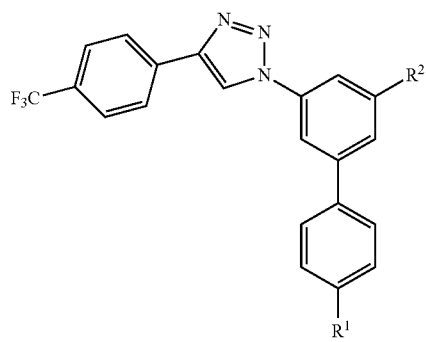
15, 16, 18-21
| Compound | $R^1$ =, other changes | cLogP$^d$ | IC$_{50}$ (μM)$^a$ |
|---|---|---|---|
| 1$^b$ PPTN | 4-piperidinyl (NH) |  | 0.0060 ± 0.0001 |
| 2$^b$ MRS4217 | 4-piperidinyl (NH) |  | 0.0317 ± 0.0080 |
| 3 MRS4537 dehydroPPTN | 1,2,3,6-tetrahydropyridin-4-yl (NH) |  | 0.018 ± 0.002 |
| 4 MRS4544 | piperazinyl (NH) |  | 0.233 ± 0.026 |
| 5 MRS4576 (cf. 4179) | 1-methyl-4-piperidinyl |  | 0.195 ± 0.120 |
| 6 MRS4578 | 1-(CH$_2$C≡CH)-4-piperidinyl |  | 0.139 ± 0.019 |
| 7 MRS4574 | 1-(CH$_2$)$_2$CH$_3$-4-piperidinyl |  | 0.133 ± 0.111 |
| 8 MRS4149 | 1-(CH$_2$)$_4$C≡CH-4-piperidinyl |  | 0.0763 ± 0.0244 |

TABLE 1-continued

| # | ID | Structure | Value |
|---|---|---|---|
| 9 | MRS4577 | piperidine-N—(CH$_2$)$_5$CH$_3$ | 0.131 ± 0.011 |
| 10 | MRS4575 | piperidine-N—COOC(CH$_3$)$_3$ | 2.44 ± 1.54 |
| 11 | MRS4573 | piperidine-N—CO((CH$_2$)$_2$O)$_6$CH$_3$ | 1.41 ± 0.56 |
| 12 | MRS4571 | piperidine-N—CO((CH$_2$)$_2$O)$_6$(CH$_2$)$_2$NH$_2$ | 0.963 ± 0.417 |
| 13 | MRS4572 | piperidine-N—CO((CH$_2$)$_2$O)$_6$(CH$_2$)$_2$NHCOCH$_3$ | 0.979 ± 0.331 |
| 14 | MRS4570 | piperidine-N—CO((CH$_2$)$_2$O)$_6$(CH$_2$)$_2$NHCOOC(CH$_3$)$_3$ | 2.83 ± 1.15 |
| 15 | MRS4533 | piperidine-NH, R$^2$ = CONH$_2$ | c |
| 16 | MRS4534 | piperidine-NH, R$^2$ = CN | 42.1 ± 8.4 |
| 17 | MRS4608 | bicyclic amine | 0.0200 ± 0.0044 |
| 18 | MRS4609 | bicyclic NH (±) | ~0.400 |
| 19 | MRS4610 | difluoro bicyclic NH (±) | |
| 20 | MRS4611 | bicyclic NH | |
| 21 | MRS4612 | bicyclic NH (±) | |

[a] IC$_{50}$ values were determined by flow cytometry of hP2Y$_{14}$R-CHO cells using a fluorescent antagonist tracer and expressed as mean ± SEM (n = 3-5).
[b] IC$_{50}$ values were from Junker et al. and Yu et al.[8,9]
[c] No inhibition by the compound discerned at the highest concentration, therefore IC$_{50}$ > 100 μM.
[d] cLogP calculated using ALOGPS 2.1 program (www.vcclab.org/lab/alogps/).[24]

TABLE 2

| Compound | R³ = | R¹ = | cLogP[d] | IC₅₀ (μM)[a] |
|---|---|---|---|---|
| 22[b] MRS4478 | 4-(trifluoromethyl)phenyl-1,2,3-triazol-1-yl | $CONH_2$ | | 0.269 ± 0.121 |
| 23[b] MRS4458 | 4-(trifluoromethyl)phenyl-1,2,3-triazol-1-yl | $CONH(CH_2)_3NH_2$ | | 0.169 ± 0.042 |
| 24 MRS4527 | 1-(4-(trifluoromethyl)phenyl)-1,2,3-triazol-4-yl | $CONH_2$ | | 1.68 ± 0.38 |
| 25 MRS4525 | 1-(4-(trifluoromethyl)phenyl)-1,2,3-triazol-4-yl | 4-piperidinyl (NH) | | 0.644 ± 0.175 |
| 26 MRS4526 | 1-(4-(trifluoromethyl)phenyl)-1,2,3-triazol-4-yl | $CONH(CH_2)_3NH_2$ | | 2.60 ± 0.56 |
| 27 MRS4530 | 4-(trifluoromethyl)benzamido | $CONH_2$ | | 3.05 ± 0.21 |
| 28 MRS4539 | (hydroxymethyl)cubane-carboxamido | 4-piperidinyl (NH) | | c |
| 29 MRS4535 | 4-(trifluoromethyl)phenyl-NH-C(O)- | $CONH_2$ | | 6.04 ± 0.81 |

TABLE 2-continued

Structures for compounds 22, 24, 25, 27-32; 23, 26; 33; 34; 35 (scaffolds shown with R¹ and R³ substituents).

| Compound | R³ = | R¹ = | cLogP[d] | IC$_{50}$ (μM)[a] |
|---|---|---|---|---|
| 30 MRS4531 | 5-(trifluoromethyl)-1H-indol-2-yl | CONH$_2$ | | 2.44 ± 0.43 |
| 31 MRS4536 | 6-(trifluoromethyl)-1H-indol-2-yl | CONH$_2$ | | 2.03 ± 0.34 |
| 32 MRS4532 | 5-(trifluoromethyl)-1H-benzimidazol-2-yl | CONH$_2$ | | 24.4 ± 3.3 |
| 33 MRS4542 | 4-(4-(trifluoromethyl)phenyl)-1H-1,2,3-triazol-1-yl | 1,2,3,6-tetrahydropyridin-4-yl | | c |
| 34 MRS4538 | 1-(4-(trifluoromethyl)phenyl)-1H-1,2,3-triazol-4-yl | piperidin-4-yl | | 11.1 ± 1.6 |
| 35 MRS4545 | 4-(trifluoromethyl)phenyl | piperidin-4-yl | | c |

[a] IC$_{50}$ values were determined by flow cytometry of hP2Y$_{14}$R-CHO cells using a fluorescent antagonist tracer and expressed as mean ± SEM (n = 3-5).
[b] IC$_{50}$ values were from Junker et al. and Yu et al.[8,9]
[c] No inhibition by the compound discerned at the highest concentration, therefore IC$_{50}$ > 100 μM.
[d] cLogP calculated using ALOGPS 2.1 program (www.vcclab.org/lab/alogps/).[24]

Example 3

This example compares inhibitory potency of antagonists at the mP2Y14R to the hP2Y14R expressed in HEK293 cells, using the fluorescence binding method. The results are set forth in Table 3.

TABLE 3

| Compound | mP2Y$_{14}$R, IC$_{50}$ (µM)$^a$ | hP2Y$_{14}$R, IC$_{50}$ (µM)$^a$ |
| --- | --- | --- |
| 1 PPTN | 0.0216 ± 0.0070 | 0.0060 ± 0.0001 |
| 2 MRS4217 | 0.142 ± 0.058 | 0.0317 ± 0.0080 |
| 4 MRS4544 | 0.499 ± 0.057 | 0.233 ± 0.026 |
| 8 MRS4149 | 0.130 ± 0.030 | 0.0763 ± 0.0244 |
| 12 MRS4571 | 0.487 ± 0.130 | 0.963 ± 0.417 |
| 17 MRS4608 | 0.x ± 0.x | 0.x ± 0.x |
| 22 MRS4478 | 0.902 ± 0.344 | 0.269 ± 0.121 |
| 23 MRS4458 | 0.384 ± 0.088 | 0.169 ± 0.042 |
| 25 MRS4525 | 0.246 ± 0.063 | 0.644 ± 0.175 |

Example 4

This example demonstrates the efficacy of compounds of the invention in a protease-mediated mouse model of asthma, in accordance with an embodiment of the invention.

P2Y$_{14}$R antagonists were tested in vivo in a protease-mediated mouse model of asthma and found to be effective in reducing the presence of eosinophils in the bronchoalveolar lavage fluid. The animals were first sensitized with ovalbumin/*Aspergillus oryzae* extract on days 0 and 7. Antagonists were injected i.p. at a dose of 10 mg/kg, 30 minutes prior to an ovalbumin challenge at day 14. When normalized and compared to vehicle (100±15%), MRS4458 (compound 23, 40.3±11.0%) showed a similar beneficial activity to PPTN (compound 1, 43.9±12.8%). Both P2Y$_{14}$R antagonist effects were statistically significant (P<0.01) compared to vehicle control.

REFERENCES

1. Burnstock, G. *Exp. Physiol.*, 2014, 99, 16-34.
2. Cekic, C.; Linden, J. *Nature Rev. Immunol.* 2016, 16, 177-192.
3. Abbracchio, M. P.; Burnstock, G.; Boeynaems, J. M.; Barnard, E. A.; Boyer, J. L.; Kennedy, C.; Fumagalli, M.; King, B. F.; Gachet, C.; Jacobson, K. A.; Weisman, G. A *Pharmacol. Rev.* 2006, 58, 281-341.
4. Lazarowski, E. R.; Harden, T. K. *Mol. Pharmacol.* 2015, 88, 151-160.
5. Sesma, J. I.; Kreda, S. M.; Steinckwich-Besancon, N.; Dang, H.; Garcia-Mata, R.; Harden, T. K.; Lazarowski, E. R. *Am. J. Physiol.—Cell Physiol.* 2012, 303, C490-C498.
6. Barrett, M. O.; Sesma, J. I.; Ball, C. B.; Jayasekara, P. S.; Jacobson, K. A.; Lazarowski, E. R.; Harden, T. K. *Mol. Pharmacol.* 2013, 84, 41-49.
7. Gao, Z.-G.; Ding, Y.; Jacobson, K. A. *Biochem. Pharmacol.* 2010, 79, 873-879.
8. Azroyan, A.; Cortez-Retamozo, V.; Bouley, R.; Liberman, R.; Ruan, Y. C.; Kiselev, E.; Jacobson, K. A.; Pittet, M. J.; Brown, D.; Breton, S. *PLoS ONE* 2015, 10(3), e0121419. doi:10.1371/journal.pone.0121419.
9. Xu, J.; Morinaga, H.; Oh, D.; Li, P.; Chen, A.; Talukdar, S.; Lazarowski, E.; Olefsky, J. M.; Kim, J. J. GPR105 *J. Immunol.* 2012, 189, 1992-1999.
10. Kinoshita, M.; Nasu-Tada, K.; Fujishita, K.; Sato, K.; Koizumi, S. Cell. *Mol. Neurobiol.* 2013, 33, 47-58.
11. Kobayashi, K.; Yamanaka, H.; Yanamoto, F.; Okubo, M.; Noguchi, K. Glia 2012, 60, 1529-1539.
12. Sesma, J. I.; Weitzer, C. D.; Livraghi-Butrico, A.; Dang, H.; Donaldson, S.; Alexis, N. E.; Jacobson, K. A.; Harden, T. K.; Lazarowski, E. R. Purinergic Signalling 2016, 12, 627-635.
13. Stachon. P.; Geis. S.; Peikert. A.; Heidenreich. A.; Michel. N. A.; nal, F.; Hoppe, N.; Dufner, B.; Schulte, L.; Marchini, T.; Cicko, S.; Ayata, K.; Zech, A.; Wolf, D.; Hilgendorf, I.; Willecke, F.; Reinöhl, J.; von Zur Miihlen, C.; Bode, C.; Idzko, M.; Zirlik A. *Arterioscler. Thromb. Vasc. Biol.* 2016, 36, 1577-1586. doi: 10.1161/ATVBAHA.115.307397. Epub 2016 Jun. 23.
14. Idzko, M.; Ferrari, D.; Eltzschig, H. K. *Nature* 2014, 509, 310-317, doi:10.1038/nature13085

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

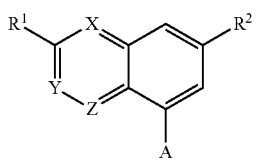

wherein (i) X is N, Y is CH, and Z is CH, (ii) X is CH, Y is N, and Z is CH, (iii) X is CH, Y is CH, and Z is N, or (iv) X, Y, and Z are all CH, R¹ is trifluoromethylphenyl, R² is COOH, CN, CONH₂, or

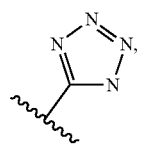 [SMILES: *c1nnn[nH]1]

A is selected from the group consisting of

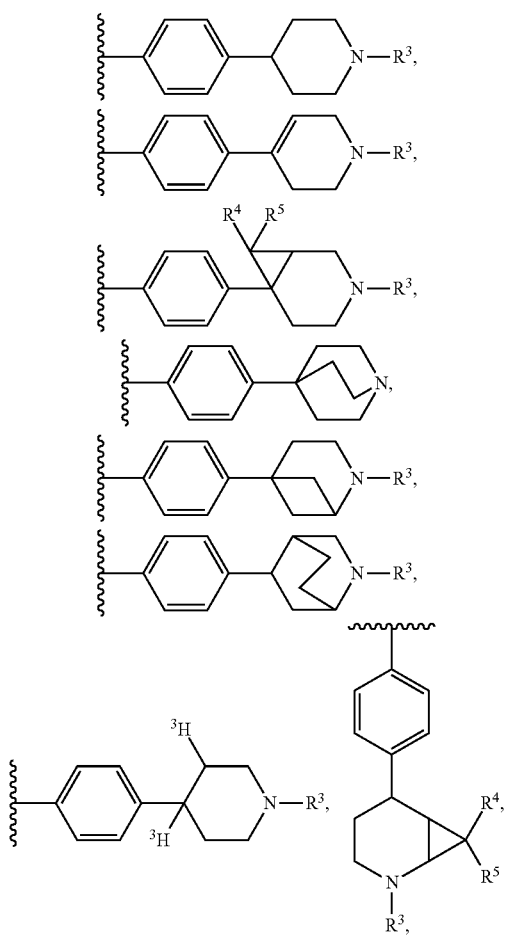

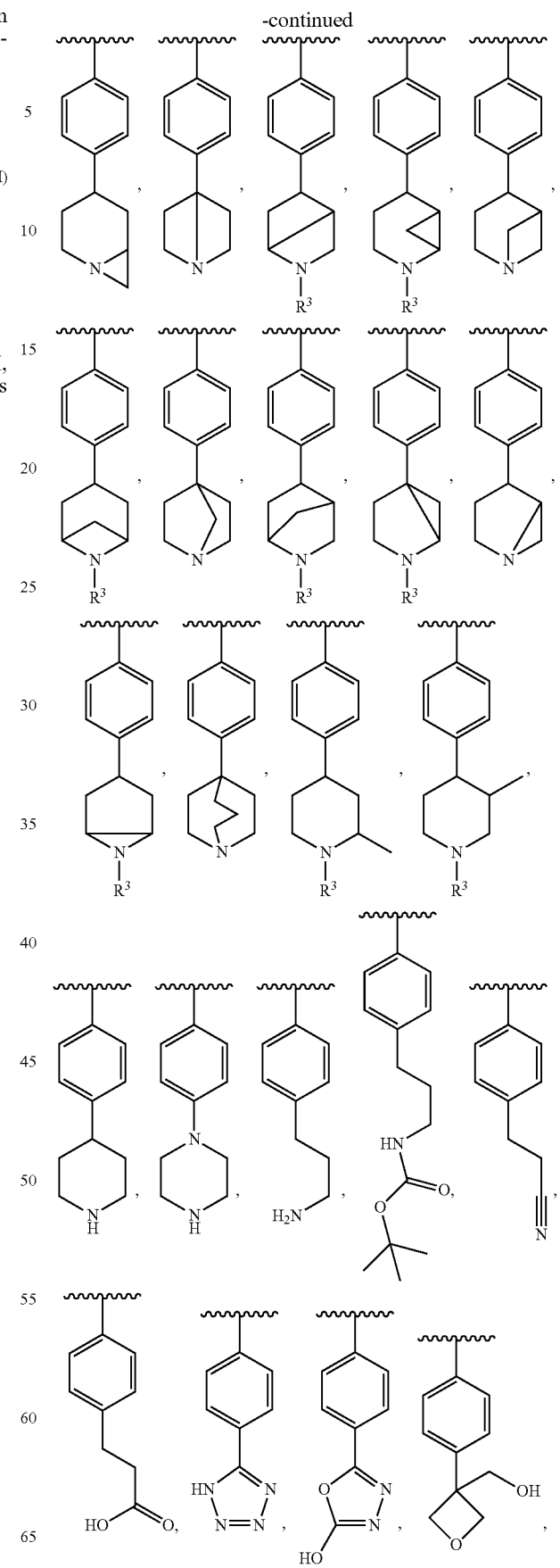

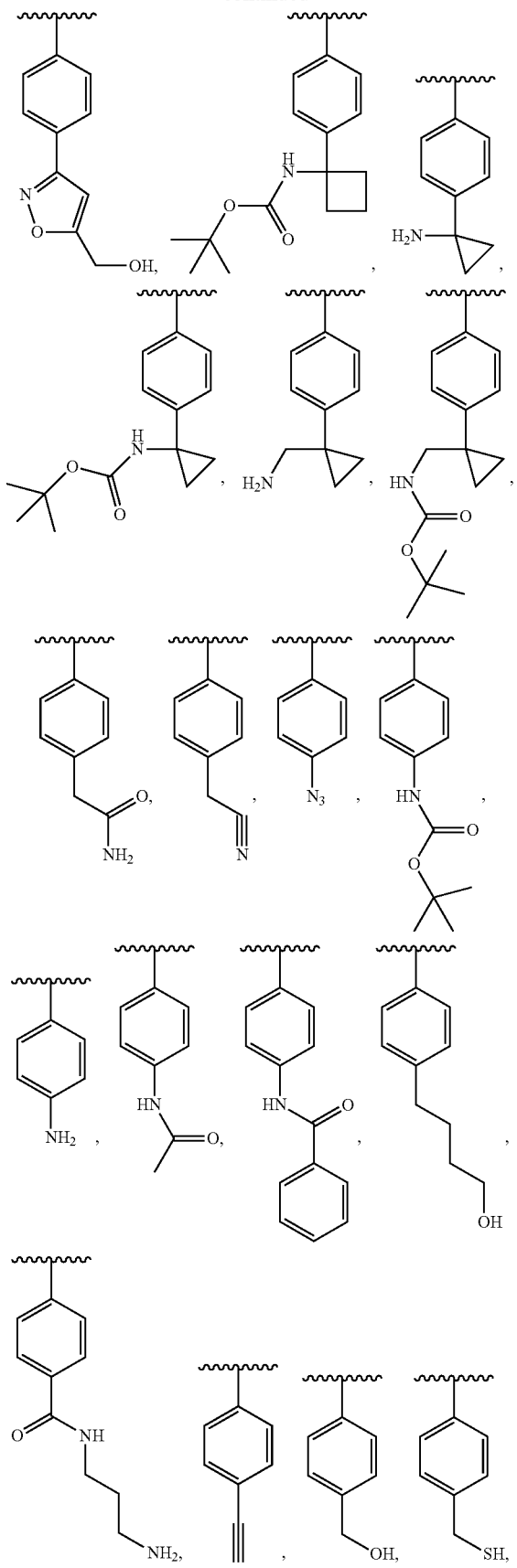
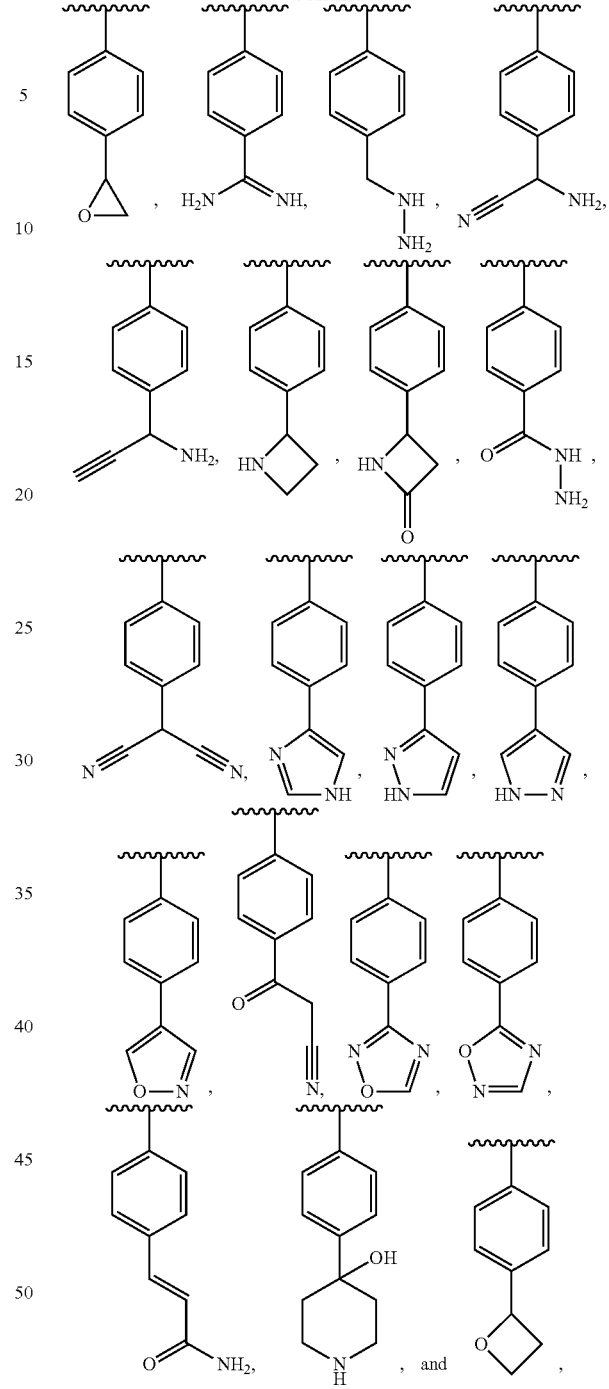

wherein R³ is at each occurrence H, $C_1$-$C_{10}$ alkyl, $C_3$-$C_{10}$ alkynyl, benzyl, $C_1$-$C_6$ alkoxycarbonyl, $CO((CH_2)_2O)_6(CH_2)_2Q$ wherein Q is $NH_2$, $NHCOCH_3$, or $NHCO(CH_3)_3$, or $CO((CH_2)_2O)_6CH_3$, and wherein R⁴ and R⁵ are each H or F, with the proviso that the compound is not 4-[4-(4-piperidinyl)phenyl]-7-[4-(trifluoromethyl)phenyl]-2-naphthalene-carboxylic acid, or a pharmacologically acceptable salt thereof.

2. The compound or salt of claim 1, wherein X, Y, and Z are all CH.

3. The compound or salt of claim 1, wherein A is
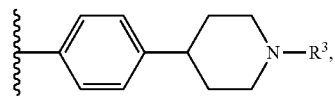
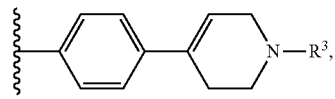
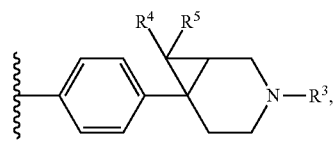
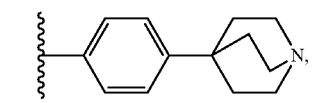
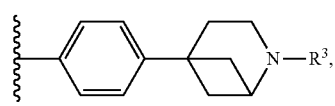
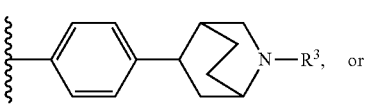 or
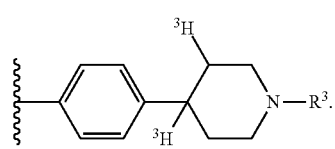
4. The compound or salt of claim 3, wherein the compound is selected from the group consisting of:
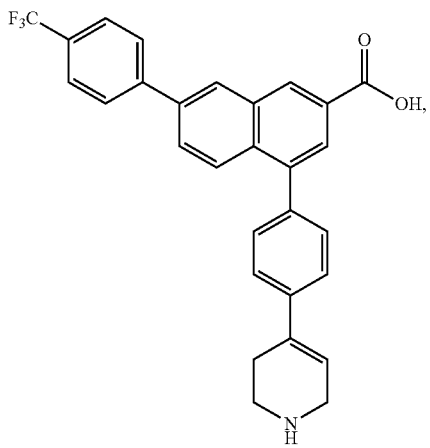
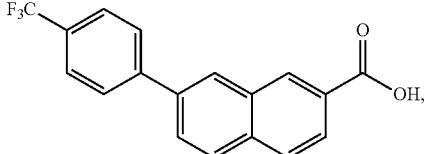
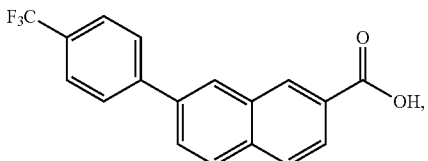
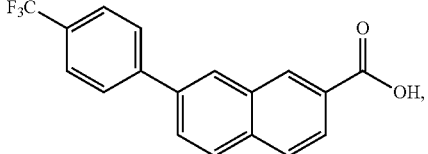

135
-continued
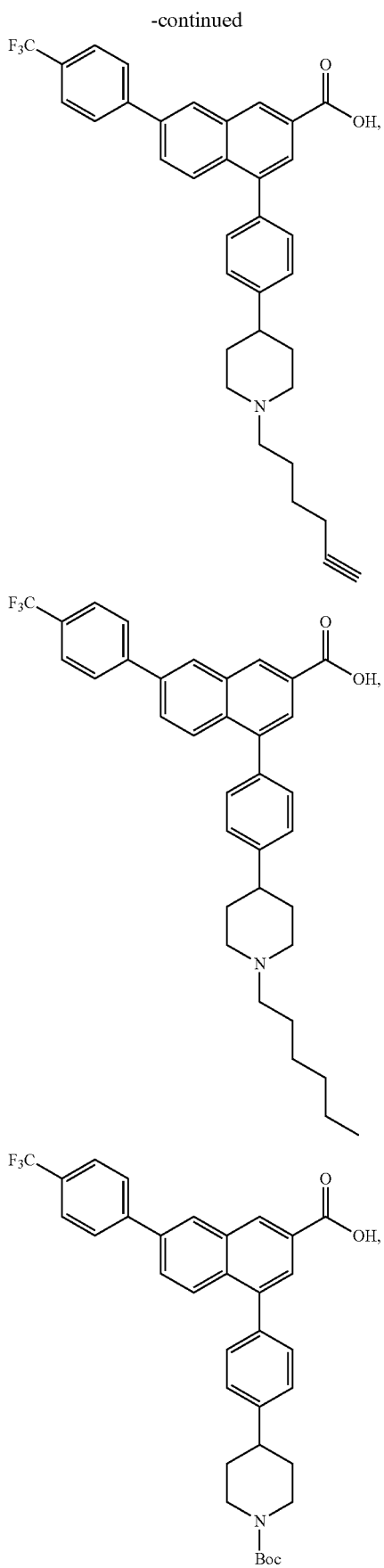
136
-continued
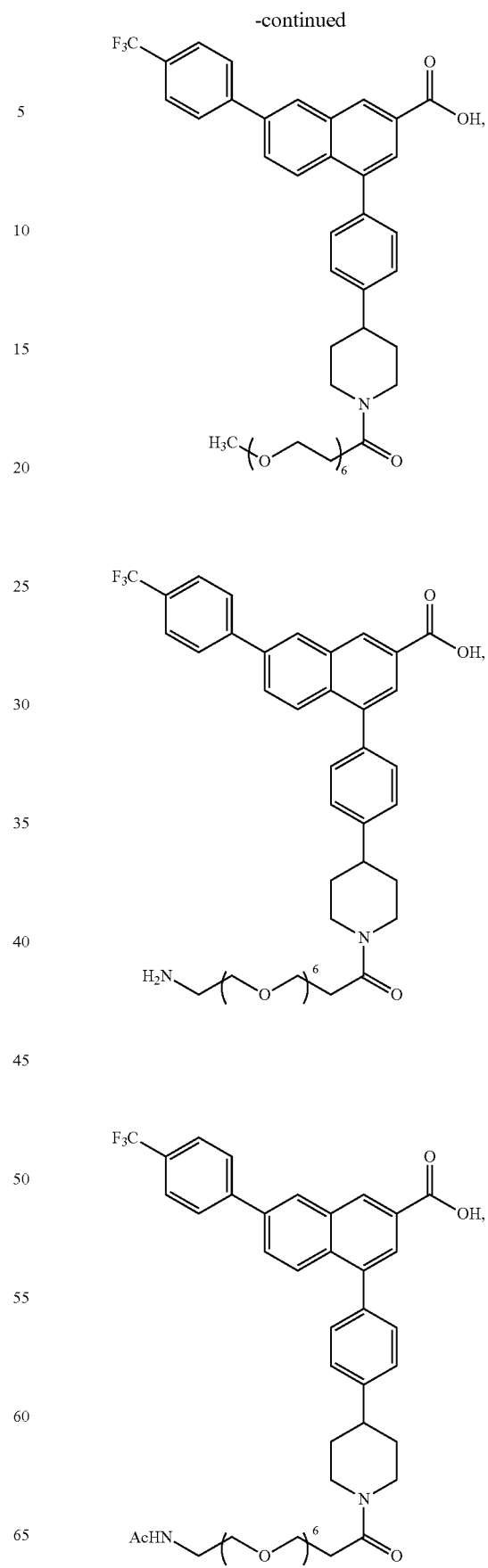

137
-continued
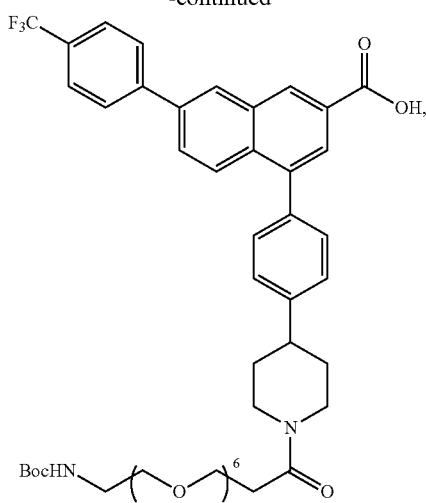
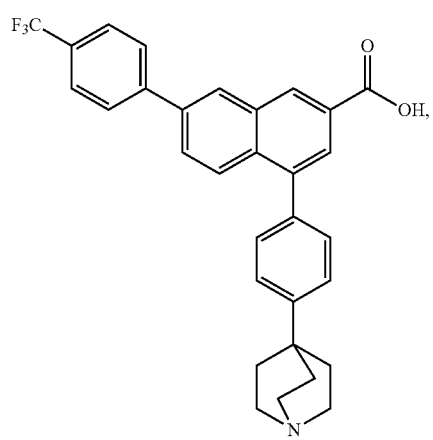
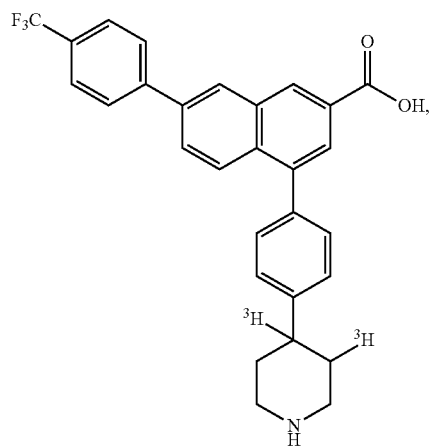
138
-continued
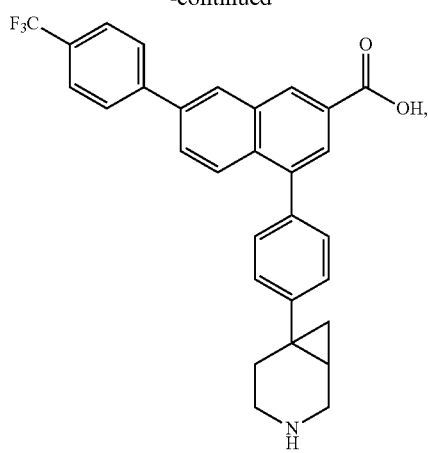
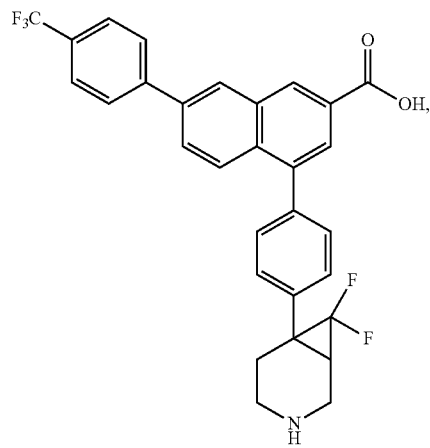
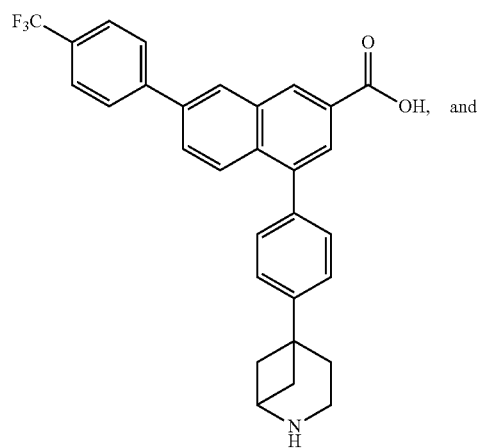

-continued

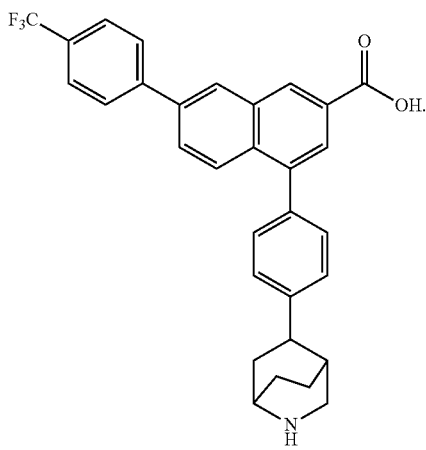

5. A pharmaceutical composition comprising a compound or salt of claim 1 and a pharmaceutically acceptable carrier.

6. A method for antagonizing a $P2Y_{14}R$ receptor in a mammal in need thereof, comprising administering to the mammal an effective amount of a compound or salt of claim 1.

7. A method for treating an inflammatory condition in a mammal in need thereof, comprising administering to the mammal an effective amount of a compound or salt of claim 1.

8. The method of claim 7, wherein the inflammatory condition is selected from the group consisting of asthma, cystic fibrosis, and sterile inflammation of the kidney.

9. A compound of formula (III), (IV), or (V):

(III)

(IV)

-continued (V)

wherein $R^6$ is selected from the group consisting of

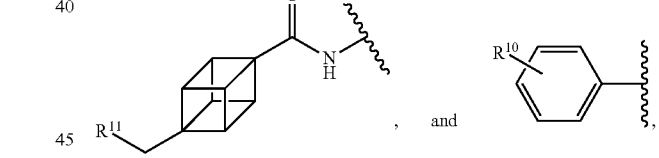

$R^7$ is COOH, $CONH_2$, CN

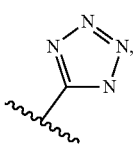 [SMILES: *c1nnn[nH]1]

or $COCH_2NMe_2$, $R^8$ is selected from the group consisting of $C_1$-$C_{10}$ alkyl, $-CONHR_{12}R_{13}$, $-CONH(CH_2)_m-NHR_{14}R_{15}$, 141
-continued
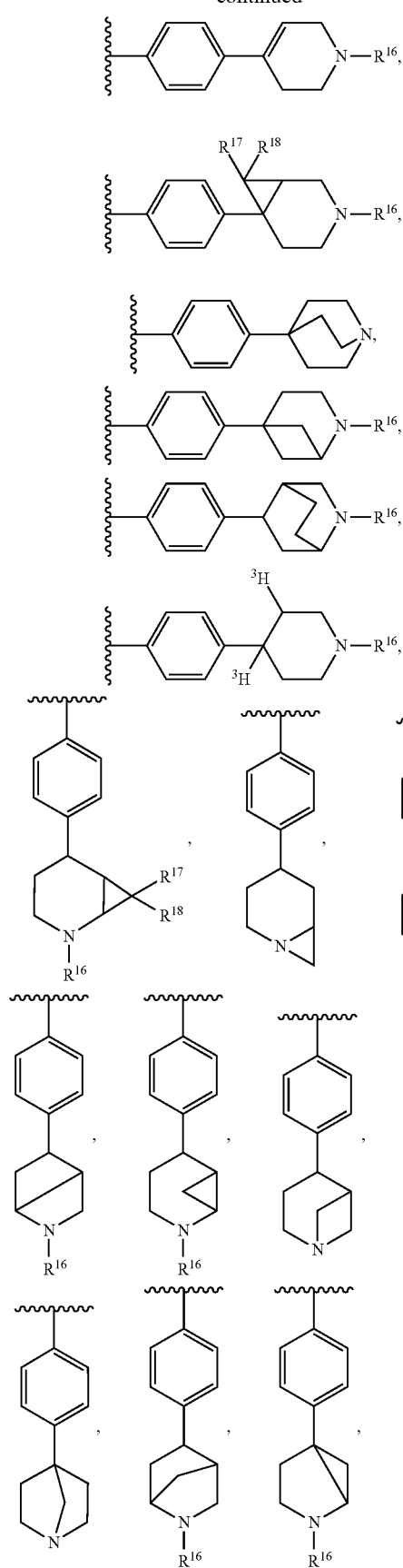
142
-continued
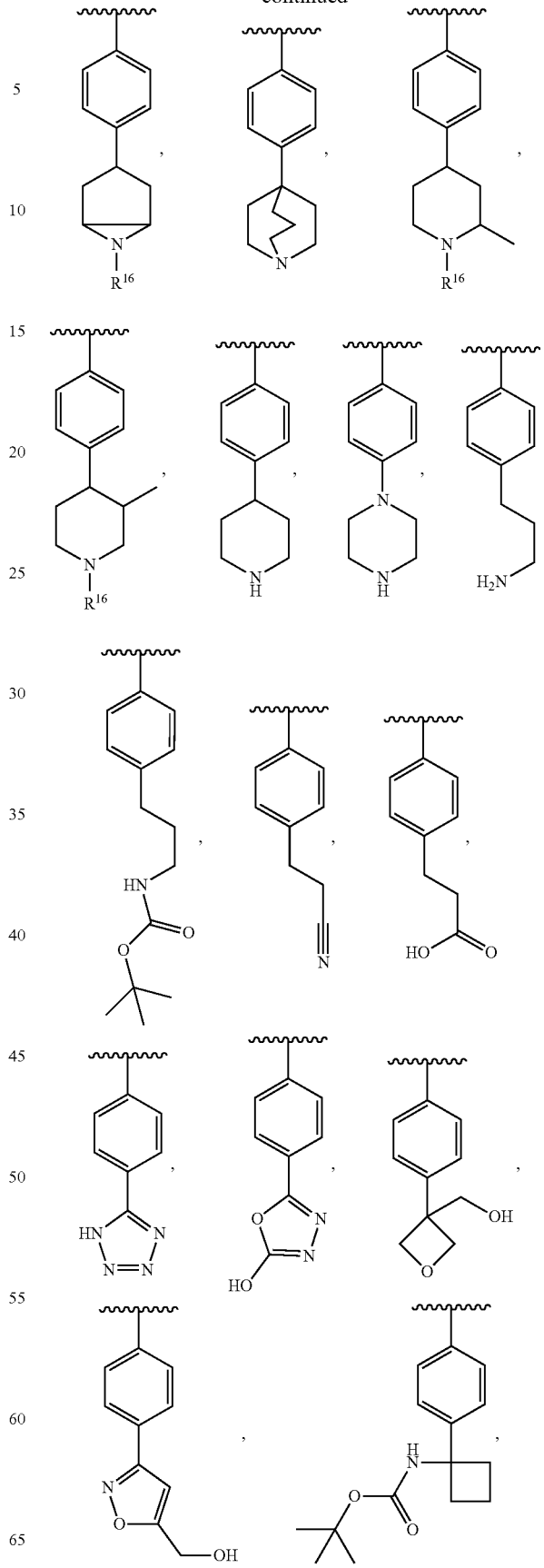

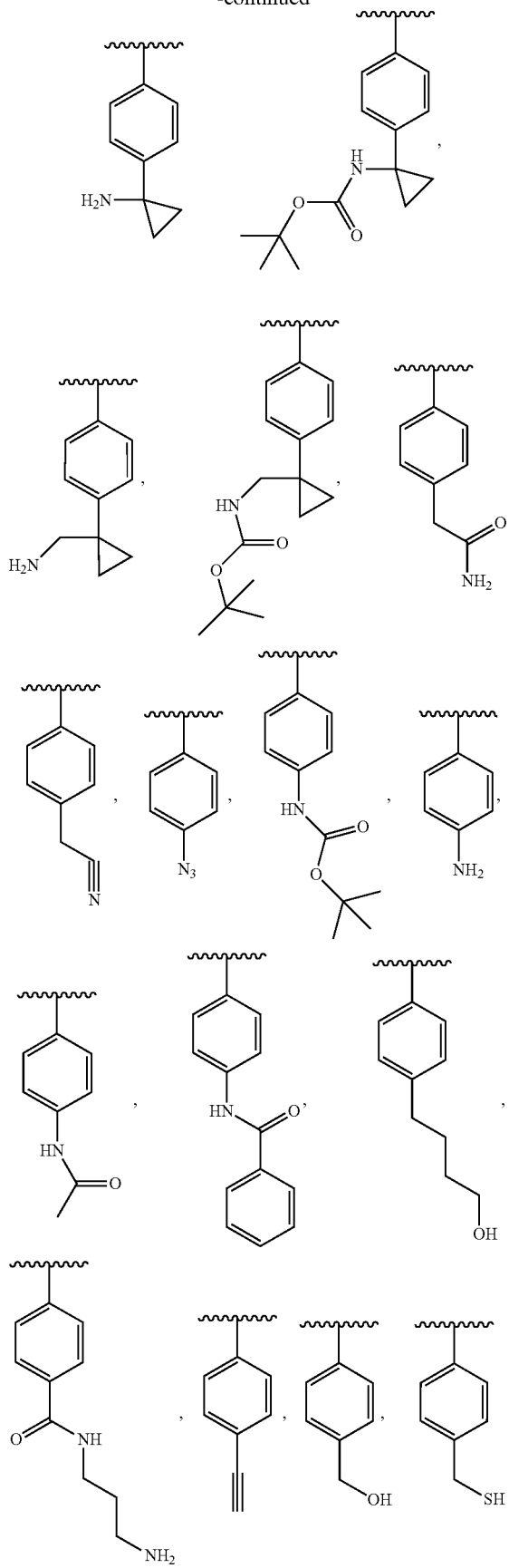
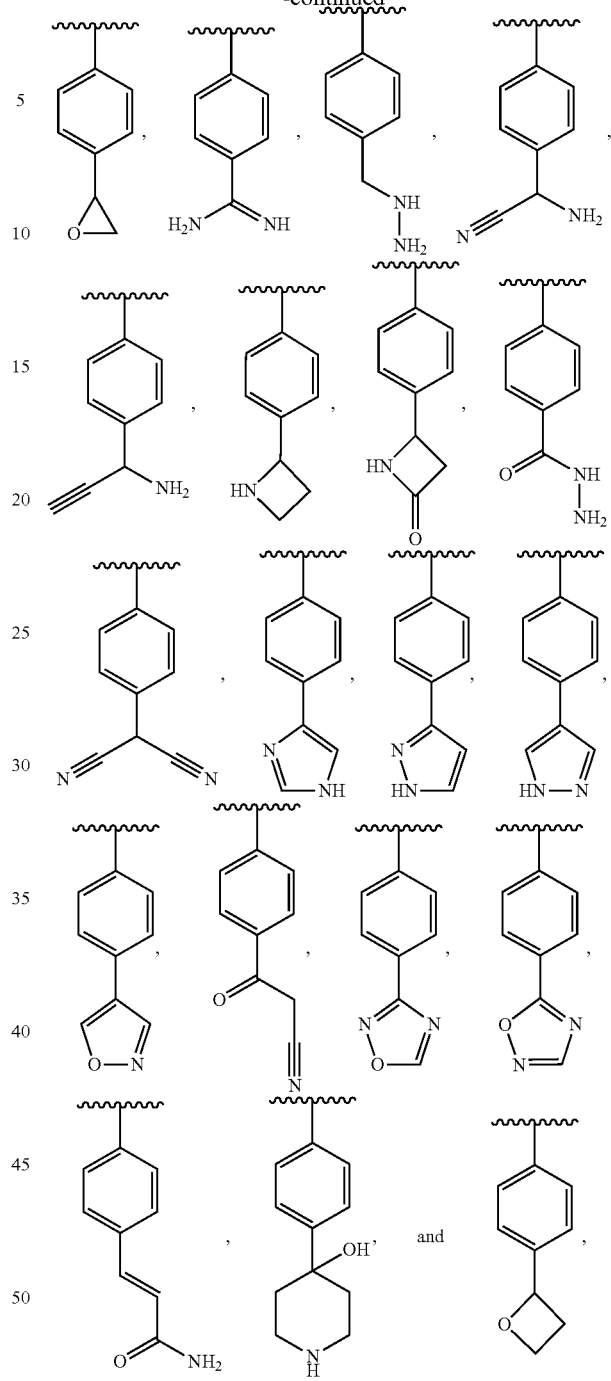

$R^{10}$ is halo or $CF_3$,
$R^{11}$ is halo, OH, or $C_1$-$C_6$ alkoxy,
$R^{12}$ and $R^{13}$ are independently H or $C_1$-$C_6$ alkyl,
$R^{14}$ and $R^{15}$ are independently H or $C_1$-$C_6$ alkyl,
$R^{16}$ is H, $C_1$-$C_{10}$ alkyl, or $C_3$-$C_{10}$ alkynyl,
$R^{17}$ and $R^{18}$ are both H or both F, and
m is an integer of from 1 to about 10,
(i) X is N, Y is CH, and Z is CH, (ii) X is CH, Y is N, and Z is CH, (iii) X is CH, Y is CH, and Z is N, or X, Y, and Z are all H,
X' and Y' are C or N, and
Z' is N or $CR^9$ wherein $R^9$ is H or $C_1$-$C_6$ alkyl, or a pharmaceutically acceptable salt thereof;
with the proviso that, in the compound of formula (III), when X=N and Y and Z are CH, $R^7$ is CN, and $R^6$ is
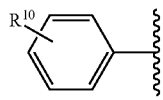
wherein $R^{10}$ is $CF_3$, then $R^8$ is not $C_6$ alkyl.
10. The compound or salt of claim 9, wherein $R^7$ is COOH.
11. The compound or salt of claim 9, wherein the compound is
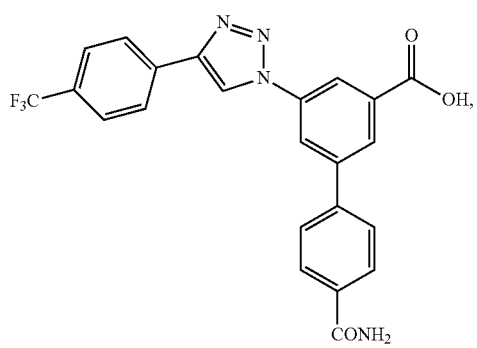
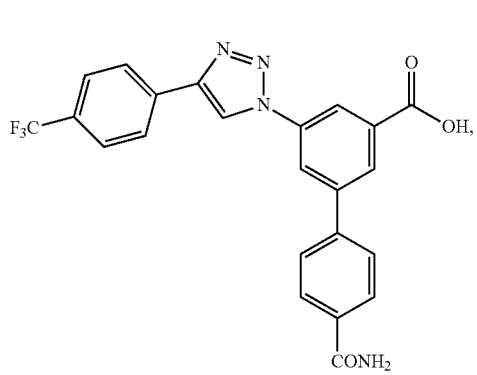
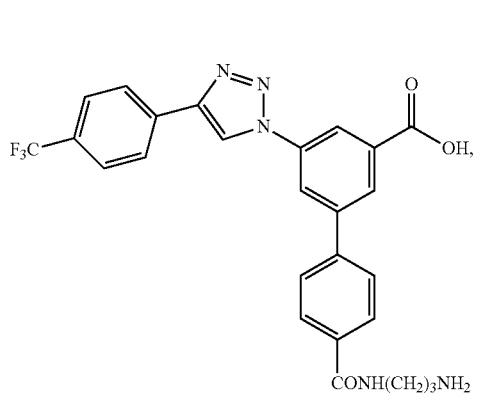
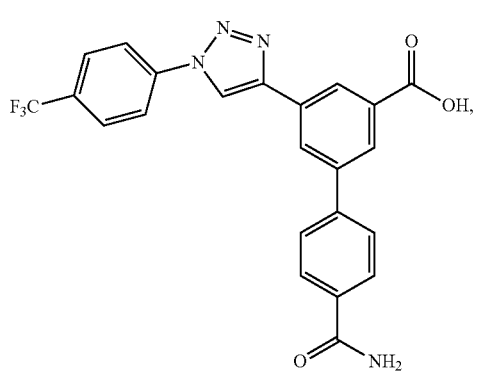
-continued
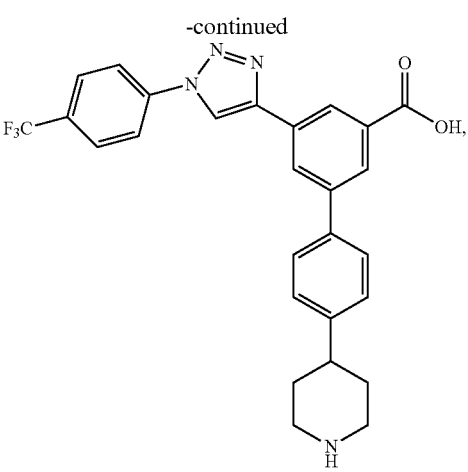
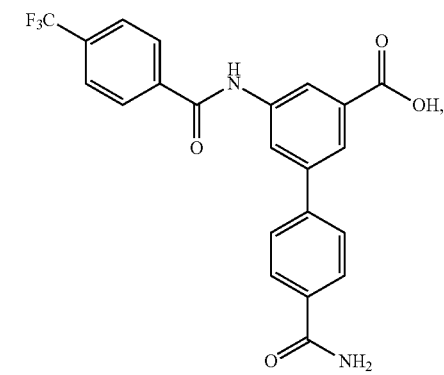
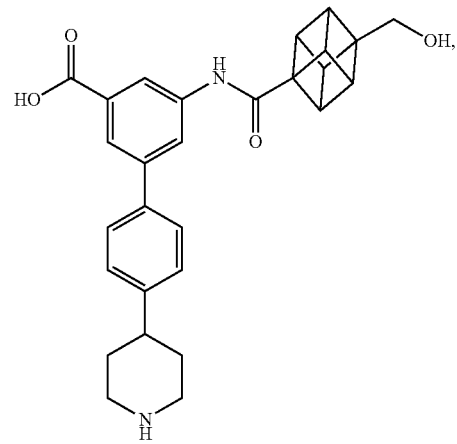
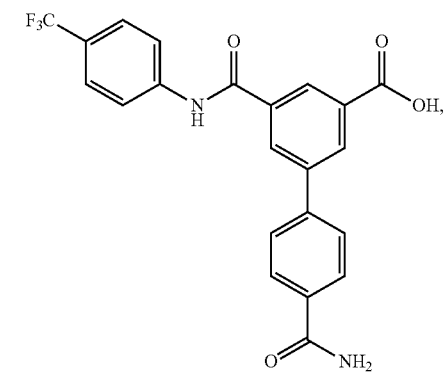

-continued

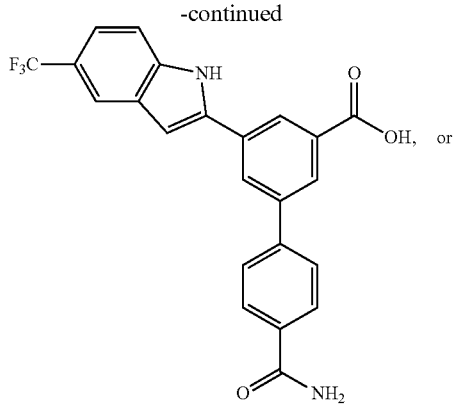

, or

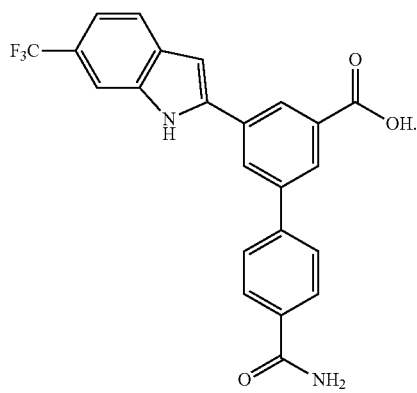 [SMILES: NC(=O)c1ccc(-c2cc(C(=O)O)cc(-c3cc4ccc(C(F)(F)F)cc4[nH]3)c2)cc1]

12. The compound or salt of claim 9, wherein the compound is

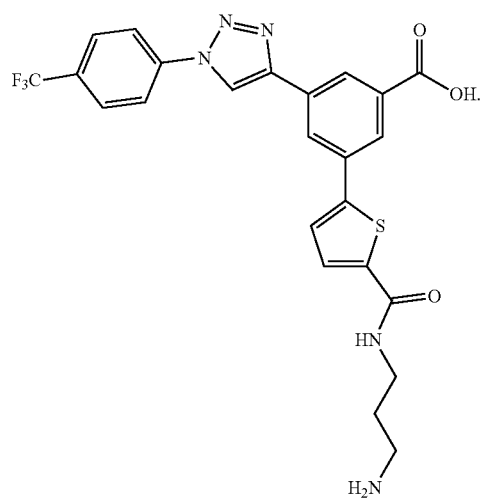 [SMILES: NCCCNC(=O)c1ccc(-c2cc(C(=O)O)cc(-c3cn(-c4ccc(C(F)(F)F)cc4)nn3)c2)s1]

13. The compound or salt of claim 9, wherein the compound is

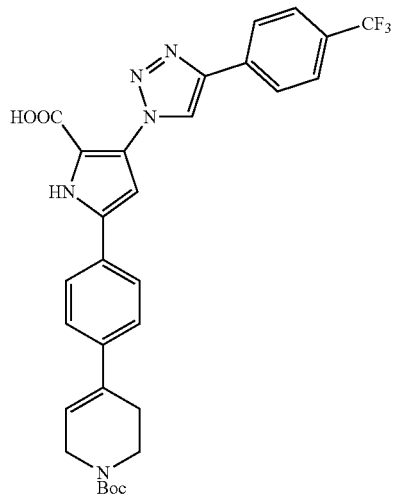 [SMILES: CC(C)(C)OC(=O)N1CC=C(c2ccc(-c3cc(-n4cc(-c5ccc(C(F)(F)F)cc5)nn4)c(C(=O)O)[nH]3)cc2)CC1]

or

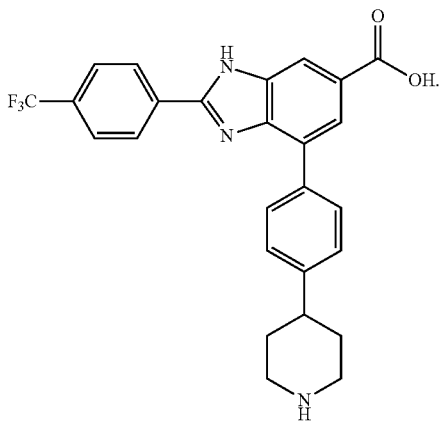 [SMILES: O=C(O)c1cc(-c2ccc(C3CCNCC3)cc2)c2nc(-c3ccc(C(F)(F)F)cc3)[nH]c2c1]

14. A pharmaceutical composition comprising a compound or salt of claim 9 and a pharmaceutically acceptable carrier.

15. A method for antagonizing a P2Y$_{14}$R receptor in a mammal in need thereof, comprising administering to the mammal an effective amount of a compound or salt of claim 9.

16. A method for treating an inflammatory condition in a mammal in need thereof, comprising administering to the mammal an effective amount of a compound or salt of claim 9.

17. The method of claim 16, wherein the inflammatory condition is selected from the group consisting of asthma, cystic fibrosis, and sterile inflammation of the kidney.

18. A compound of formula (II):
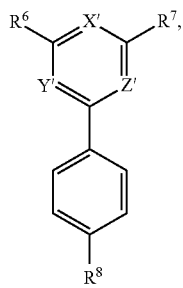
(II)
wherein $R^6$ is selected from the group consisting of
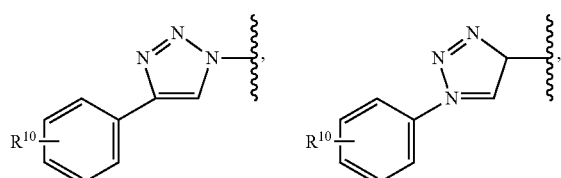
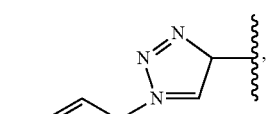
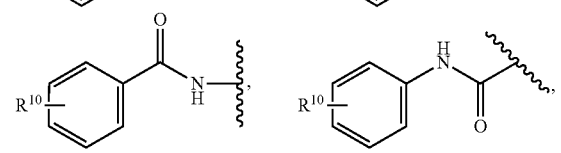
and
$R^7$ is COOH, CONH$_2$, CN
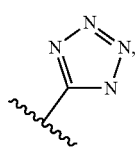 [SMILES: *c1nnn[nH]1]
or COCH$_2$NMe$_2$,
$R^8$ is selected from the group consisting of C$_2$-C$_{10}$ alkyl, —CONHR$_{12}$R$_{13}$, —CONH(CH$_2$)$_m$—NHR$_{14}$R$_{15}$,
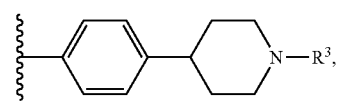
-continued
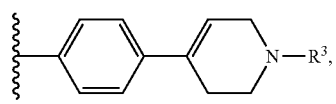
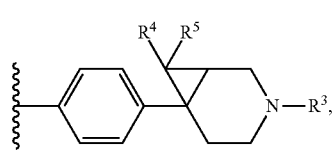
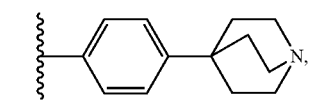
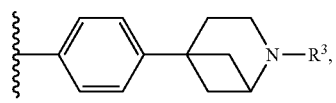
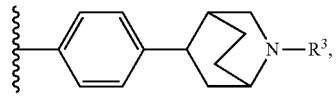
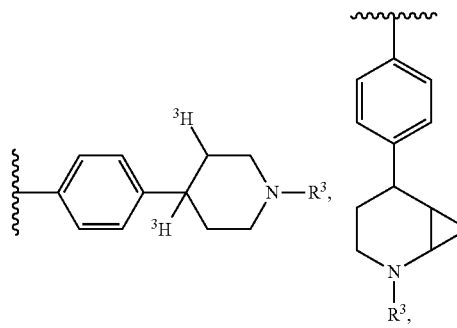
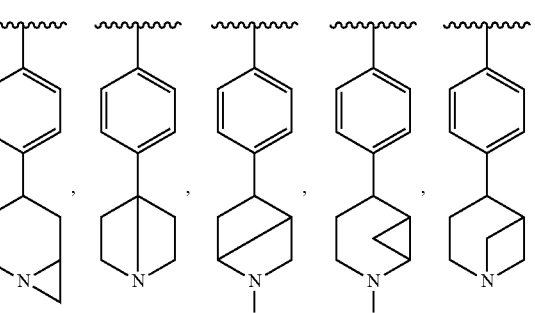
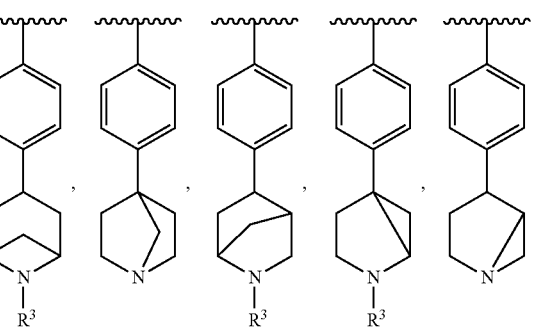

151
-continued
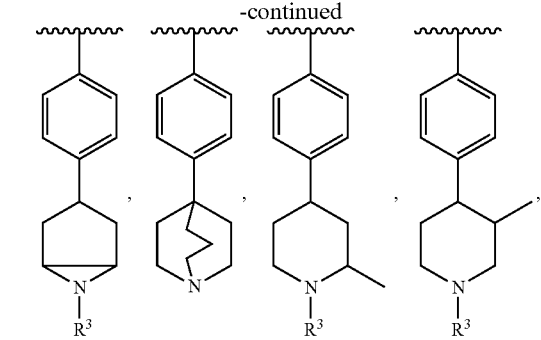
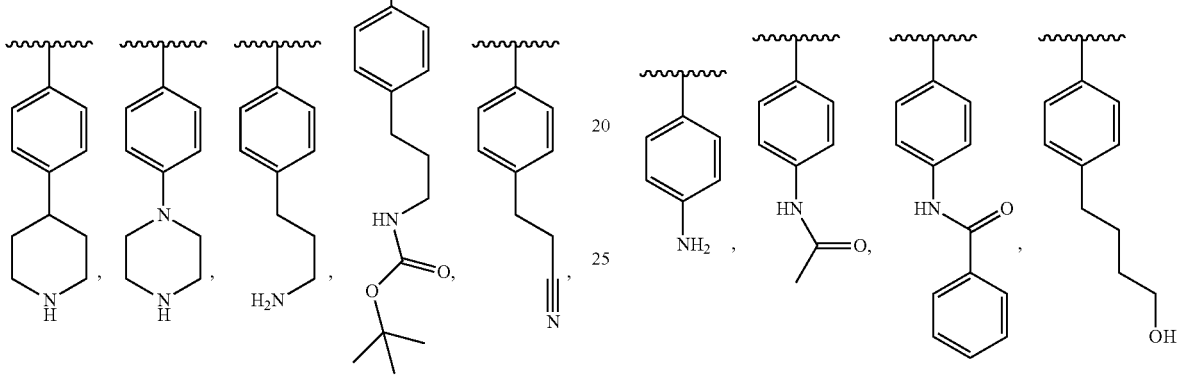
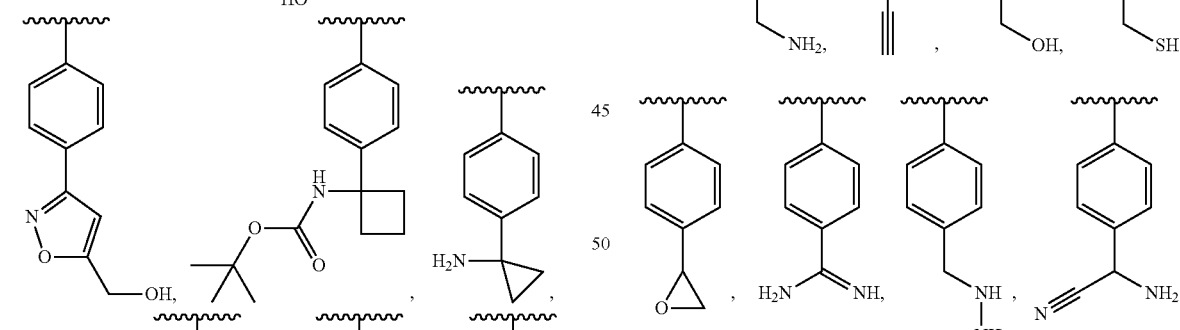
152
-continued
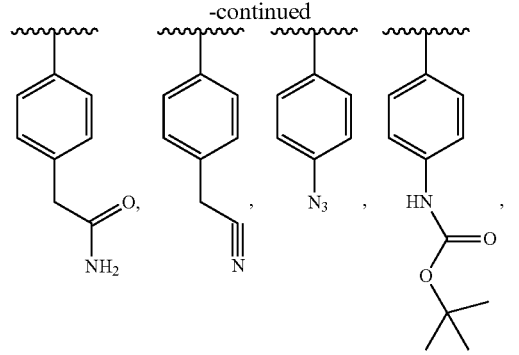
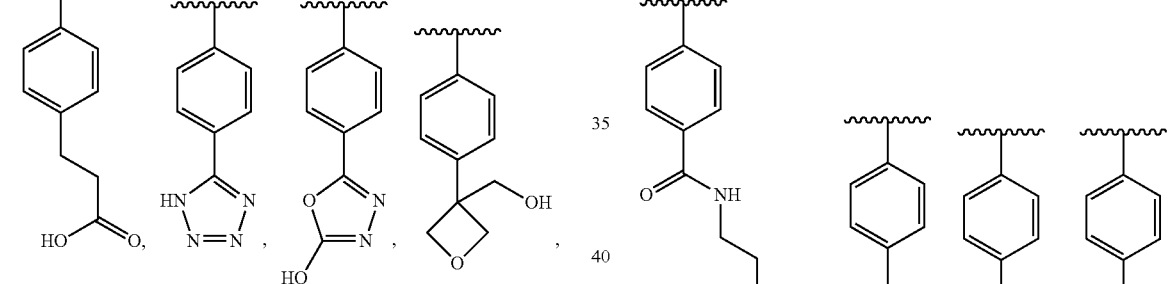
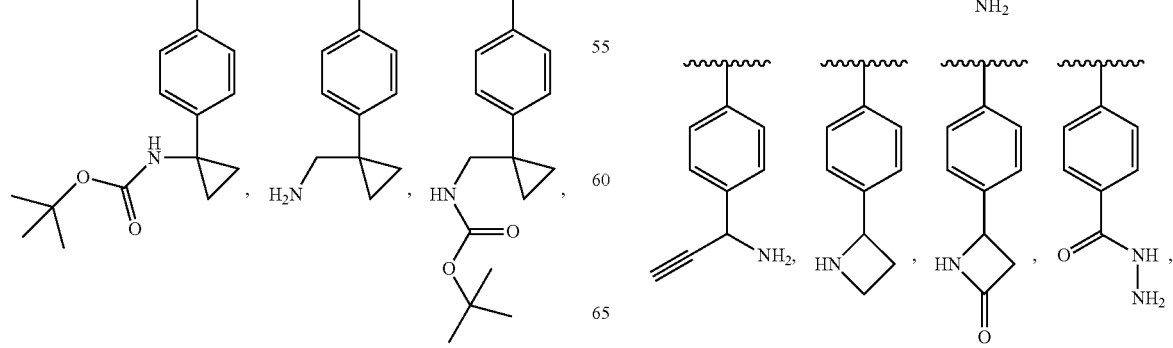

-continued

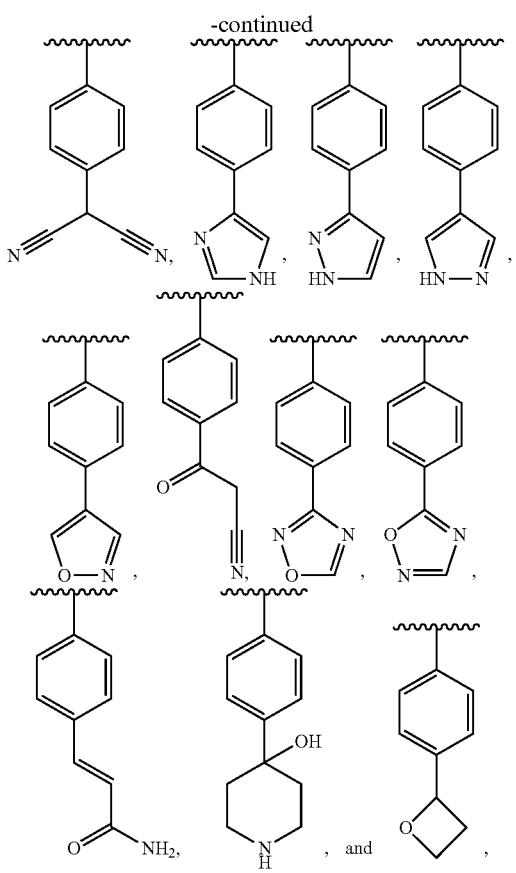

wherein:
$R^{10}$ is halo or $CF_3$,
$R^{11}$ is halo, OH, or $C_1$-$C_6$ alkoxy,
$R^{12}$ and $R^{13}$ are independently H or $C_1$-$C_6$ alkyl,
$R^{14}$ and $R^{15}$ are independently H or $C_1$-$C_6$ alkyl,
$R^{16}$ is H, $C_1$-$C_{10}$ alkyl, or $C_3$-$C_{10}$ alkynyl,
$R^{17}$ and $R^{18}$ are both H or both F, m is an integer of from 1 to about 10,
X' and Y' are C or N, and
Z' is N or $CR^9$ wherein $R^9$ is H or $C_1$-$C_6$ alkyl,
with the proviso that when $R^6$ is 4-chlorophenyl, $R^7$ is COOH, and $R^9$ is CH, then $R^8$ is not alkyl;
or a pharmaceutically acceptable salt thereof.

19. A pharmaceutical composition comprising a compound or salt of claim 18 and a pharmaceutically acceptable carrier.

20. A method for antagonizing a $P2Y_{14}R$ receptor in a mammal in need thereof, comprising administering to the mammal an effective amount of a compound or salt of claim 18.

21. The compound or salt of claim 9, wherein the compound is a compound of formula (III) and wherein $R^7$ is COOH, $CONH_2$

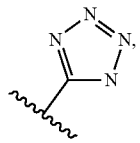

or $COCH_2NMe_2$.

22. A pharmaceutical composition comprising a compound or salt of claim 21 and a pharmaceutically acceptable carrier.

23. A method for antagonizing a $P2Y_{14}R$ receptor in a mammal in need thereof, comprising administering to the mammal an effective amount of a compound or salt of claim 21.

24. A method for treating an inflammatory condition in a mammal in need thereof, comprising administering to the mammal an effective amount of a compound or salt of claim 21.

25. The method of claim 24, wherein the inflammatory condition is selected from the group consisting of asthma, cystic fibrosis, and sterile inflammation of the kidney.

* * * * *

UNITED STATES PATENT AND TRADEMARK OFFICE
CERTIFICATE OF CORRECTION

PATENT NO. : 11,584,736 B2
APPLICATION NO. : 16/967177
DATED : February 21, 2023
INVENTOR(S) : Jacobson et al.

Page 1 of 2

It is certified that error appears in the above-identified patent and that said Letters Patent is hereby corrected as shown below:

In the Claims

At Column 136, Lines 25-42, Claim 4:

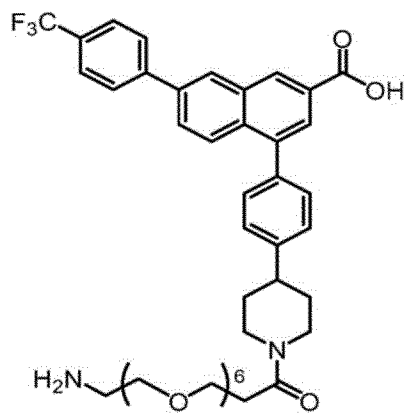 should be replaced with: 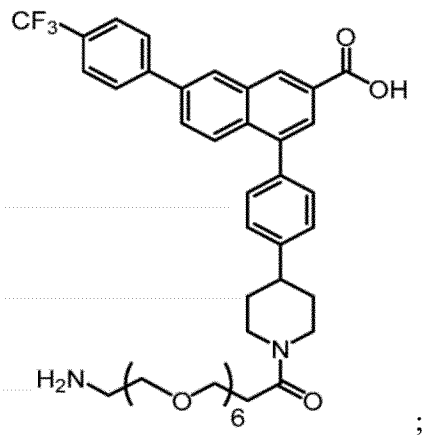 ;

At Column 136, Lines 48-65, Claim 4:

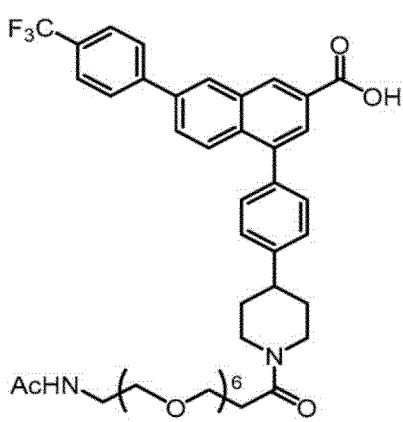 should be replaced with: 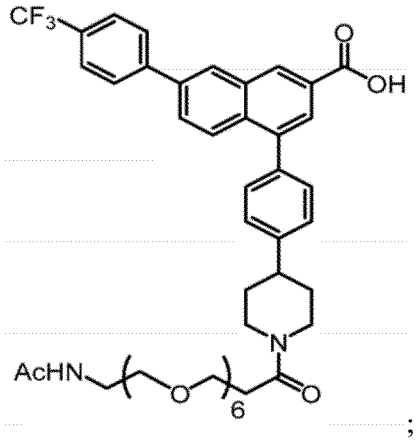 ;

Signed and Sealed this
Sixth Day of June, 2023

Katherine Kelly Vidal
*Director of the United States Patent and Trademark Office*

CERTIFICATE OF CORRECTION (continued)
U.S. Pat. No. 11,584,736 B2

And at Column 137, Lines 1-20, Claim 4:

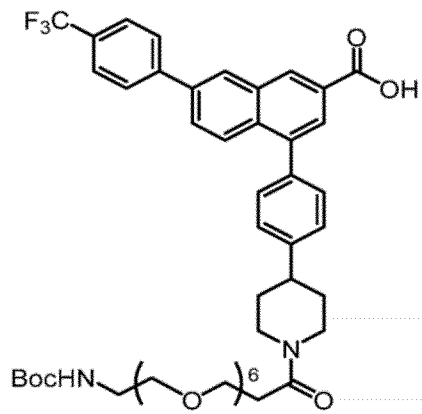 should be replaced with: 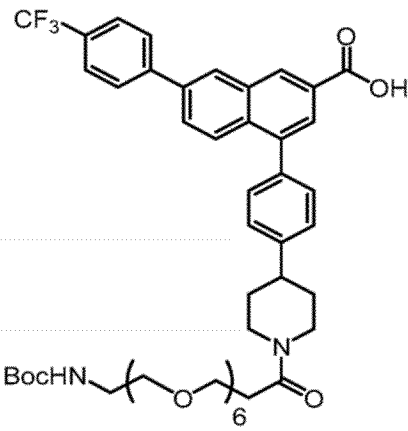 .